US009222121B2

(12) United States Patent
Beech et al.

(10) Patent No.: US 9,222,121 B2
(45) Date of Patent: Dec. 29, 2015

(54) METHODS AND COMPOSITIONS FOR DIAGNOSING DISEASE

(71) Applicant: Intrexon Corporation, Blacksburg, VA (US)

(72) Inventors: Robert P. Beech, Cincinnati, OH (US); Thomas D. Reed, Arlington, VA (US); Robert Patzig, Blacksburg, VA (US)

(73) Assignee: Intrexon Corporation, Blacksburg, VA (US)

( * ) Notice: Subject to any disclaimer, the term of this patent is extended or adjusted under 35 U.S.C. 154(b) by 0 days.

(21) Appl. No.: 14/459,480

(22) Filed: Aug. 14, 2014

(65) Prior Publication Data
US 2015/0056631 A1 Feb. 26, 2015

Related U.S. Application Data

(63) Continuation of application No. 13/717,483, filed on Dec. 17, 2012, now abandoned, which is a continuation of application No. 12/197,559, filed on Aug. 25, 2008, now abandoned.

(60) Provisional application No. 61/047,940, filed on Apr. 25, 2008, provisional application No. 61/014,654, filed on Dec. 18, 2007, provisional application No. 60/957,474, filed on Aug. 23, 2007.

(51) Int. Cl.
*A61K 49/00* (2006.01)
*C12Q 1/00* (2006.01)
*C12Q 1/68* (2006.01)
*C12Q 1/66* (2006.01)
*C12N 15/63* (2006.01)

(52) U.S. Cl.
CPC *C12Q 1/66* (2013.01); *C12N 15/63* (2013.01); *C12Q 1/6897* (2013.01); *C12Q 1/6883* (2013.01); *G01N 2800/245* (2013.01)

(58) Field of Classification Search
CPC ......... C12Q 1/6897; C12Q 1/66; C12N 15/63
USPC ........................................................ 424/9.2
See application file for complete search history.

(56) References Cited

U.S. PATENT DOCUMENTS

| | | |
|---|---|---|
| 4,352,883 A | 10/1982 | Lim |
| 4,409,331 A | 10/1983 | Lim |
| 4,673,566 A | 6/1987 | Goosen et al. |
| 4,680,174 A | 7/1987 | Jarvis, Jr. et al. |
| 4,689,293 A | 8/1987 | Goosen et al. |
| 4,806,355 A | 2/1989 | Goosen et al. |
| 4,981,784 A | 1/1991 | Evans et al. |
| 4,985,461 A | 1/1991 | Hsu et al. |
| 5,117,057 A | 5/1992 | Hsu et al. |
| 5,225,443 A | 7/1993 | Murphy et al. |
| 5,354,844 A | 10/1994 | Beug et al. |
| 5,378,726 A | 1/1995 | Yanagi et al. |
| 5,459,127 A | 10/1995 | Felgner et al. |
| 5,530,028 A | 6/1996 | Lidert et al. |
| 5,550,178 A | 8/1996 | Desai et al. |
| 5,580,859 A | 12/1996 | Felgner et al. |
| 5,589,466 A | 12/1996 | Felgner et al. |
| 5,648,099 A | 7/1997 | Batich et al. |
| 5,653,975 A | 8/1997 | Baetge et al. |
| 5,656,481 A | 8/1997 | Baetge et al. |
| 5,693,622 A | 12/1997 | Wolff et al. |
| 5,700,848 A | 12/1997 | Soon-Shiong et al. |
| 5,759,578 A | 6/1998 | Soon-Shiong et al. |
| 5,773,286 A | 6/1998 | Dionne et al. |
| 5,786,216 A | 7/1998 | Dionne et al. |
| 5,788,988 A | 8/1998 | Soon-Shiong et al. |
| 5,798,113 A | 8/1998 | Dionne et al. |
| 5,800,828 A | 9/1998 | Dionne et al. |
| 5,800,829 A | 9/1998 | Dionne et al. |
| 5,801,033 A | 9/1998 | Hubbell et al. |
| 5,834,001 A | 11/1998 | Dionne et al. |
| 5,834,274 A | 11/1998 | Hubbell et al. |
| 5,837,234 A | 11/1998 | Gentile et al. |
| 5,837,747 A | 11/1998 | Soon-Shiong et al. |
| 5,843,743 A | 12/1998 | Hubbell et al. |
| 5,846,530 A | 12/1998 | Soon-Shiong et al. |
| 5,846,947 A | 12/1998 | Behr et al. |
| 5,856,435 A | 1/1999 | Bazile et al. |

(Continued)

FOREIGN PATENT DOCUMENTS

| | | |
|---|---|---|
| WO | WO 01/70816 | 9/2001 |
| WO | WO 02/29075 | 4/2002 |

(Continued)

OTHER PUBLICATIONS

Abruzzese, R. V., et al., "Ligand-Dependent Regulation of Plasmid-Based Transgene Expression in Vivo," *Human Gene Therapy* 10:1499-1507, Mary Ann Liebert, Inc., United States (1999).

Altschul, S.F., et al., "Basic Local Alignment Search Tool," *The Journal of Molecular Biology* 215:403-410, Academic Press Limited, United States (1993).

Antoniewski, C., et al., "The Ecdysone Response Enhancer of the *Fbp1* Gene of *Drosophilia melanogaster* Is a Direct Target for the EcR/USP Nuclear Receptor," *Molecular and Cellular Biology* 14:4465-4474, American Society for Microbiology, United States (1994).

Benoist, C. and Chambon, P., "In vivo sequence requirements of the SV40 early promoter region," *Nature* 290:304-310, Nature Publishing Group, England (1981).

(Continued)

*Primary Examiner* — Scott Long
*Assistant Examiner* — Kelaginamane T Hiriyanna
(74) *Attorney, Agent, or Firm* — Sterne, Kessler, Goldstein & Fox P.L.L.C.

(57) ABSTRACT

The present invention relates to methods and compositions for diagnosing a disease or disorder in a subject by introducing into cells of the subject a diagnostic gene switch construct and monitoring expression of a reporter gene. The invention further relates to methods and compositions for monitoring the progression of a disease or disorder or the effectiveness of a treatment for a disease or disorder.

8 Claims, 10 Drawing Sheets

(56) References Cited

U.S. PATENT DOCUMENTS

| | | | |
|---|---|---|---|
| 5,858,746 | A | 1/1999 | Hubbell et al. |
| 5,902,745 | A | 5/1999 | Butler et al. |
| 5,908,623 | A | 6/1999 | Baetge et al. |
| 5,912,005 | A | 6/1999 | Lanza et al. |
| 5,916,790 | A | 6/1999 | Enevold |
| 5,945,400 | A | 8/1999 | Scherman et al. |
| 6,013,836 | A | 1/2000 | Hsu et al. |
| 6,020,200 | A | 2/2000 | Enevold |
| 6,083,523 | A | 7/2000 | Dionne et al. |
| 6,107,286 | A | 8/2000 | Byk et al. |
| 6,123,700 | A | 9/2000 | Mills et al. |
| 6,126,936 | A | 10/2000 | Lanza et al. |
| 6,180,007 | B1 | 1/2001 | Gentile et al. |
| 6,258,603 | B1 | 7/2001 | Carlson et al. |
| 6,258,870 | B1 | 7/2001 | Hubbell et al. |
| 6,264,941 | B1 | 7/2001 | Baetge et al. |
| 6,281,015 | B1 | 8/2001 | Mooney et al. |
| 6,287,558 | B1 | 9/2001 | Lanza et al. |
| 6,303,355 | B1 | 10/2001 | Opara |
| 6,306,454 | B1 | 10/2001 | Ung-Chhun et al. |
| 6,337,008 | B1 | 1/2002 | Christensen et al. |
| 6,342,896 | B1 | 1/2002 | Shetter et al. |
| 6,365,385 | B1 | 4/2002 | Opara |
| 6,368,612 | B1 | 4/2002 | Lanza et al. |
| 6,495,161 | B1 | 12/2002 | Soon-Shiong et al. |
| RE38,027 | E | 3/2003 | Jain et al. |
| 6,558,665 | B1 | 5/2003 | Cohen et al. |
| 6,610,668 | B2 | 8/2003 | Vournakis et al. |
| 6,706,470 | B2 | 3/2004 | Choo et al. |
| 6,727,322 | B2 | 4/2004 | Kennedy et al. |
| 6,762,959 | B2 | 7/2004 | Kim |
| 6,783,964 | B2 | 8/2004 | Opara |
| 6,808,705 | B2 | 10/2004 | Asina et al. |
| 6,818,018 | B1 | 11/2004 | Sawhney |
| 6,911,227 | B2 | 6/2005 | Hubbell et al. |
| 6,916,640 | B2 | 7/2005 | Yu et al. |
| 6,960,351 | B2 | 11/2005 | Dionne et al. |
| 7,045,315 | B2 | 5/2006 | Evans et al. |
| 7,091,038 | B2 | 8/2006 | Palli et al. |
| RE39,542 | E | 4/2007 | Jain et al. |
| 7,226,978 | B2 | 6/2007 | Tapsak et al. |
| 7,456,315 | B2 | 11/2008 | Hormann et al. |
| 2002/0110861 | A1 | 8/2002 | Dhadialla et al. |
| 2003/0008349 | A1 | 1/2003 | Voellmy |
| 2004/0005302 | A1 | 1/2004 | Hortelano |
| 2004/0033600 | A1 | 2/2004 | Palli et al. |
| 2004/0049037 | A1 | 3/2004 | Tice et al. |
| 2004/0096942 | A1 | 5/2004 | Kapitskaya et al. |
| 2004/0171651 | A1 | 9/2004 | Hormann et al. |
| 2004/0185556 | A1 | 9/2004 | Reed |
| 2004/0235097 | A1 | 11/2004 | Zhang et al. |
| 2005/0209283 | A1 | 9/2005 | Hormann et al. |
| 2005/0266457 | A1 | 12/2005 | Palli et al. |
| 2006/0014711 | A1 | 1/2006 | Evans et al. |
| 2006/0020146 | A1 | 1/2006 | Hormann et al. |
| 2006/0100416 | A1 | 5/2006 | Palli et al. |
| 2006/0228776 | A1 | 10/2006 | Kaplitt et al. |
| 2006/0263405 | A1 | 11/2006 | Bruce et al. |
| 2007/0117766 | A1 | 5/2007 | Phillips et al. |
| 2007/0161086 | A1 | 7/2007 | Palli et al. |
| 2008/0050808 | A1 | 2/2008 | Reed et al. |

FOREIGN PATENT DOCUMENTS

| | | |
|---|---|---|
| WO | WO 02/066612 | 8/2002 |
| WO | WO 02/066613 | 8/2002 |
| WO | WO 02/066614 | 8/2002 |
| WO | WO 02/066615 | 8/2002 |
| WO | WO 2005/040336 | 5/2005 |
| WO | WO 2005/108617 | 11/2005 |
| WO | WO 2005/116231 | 12/2005 |
| WO | WO 2006/083253 | 8/2006 |
| WO | WO 2007/038276 | 4/2007 |
| WO | WO 2007/046719 | 4/2007 |

OTHER PUBLICATIONS

Brent, R., and Ptashne, M., "A Eukaryotic Transcriptional Activator Bearing the DNA Specificity of a Prokaryotic Repressor," *Cell* 43:729-736, Cell Press, United States (1985).

Cherbas, L., et al., "Identification of ecdysone response elements by analysis of the *Drosophila Eip28/29* gene," *Genes & Development* 5:120-131, Cold Springs Laboratory Press, United States (1991).

Ciavatta, D., et al., "A DNA insulator prevents repression of a targeted X-linked transgene but not its random or imprinted X inactivation," *Proceedings for the National Academy of Science* 103:9958-9963, The National Academy of Sciences, United States (2006).

Curiel, D.T., et al., "High-Efficiency Gene Transfer Mediated by Adenovirus Coupled to DNA-Polylsine Complexes," *Human Gene Therapy* 3:147-154, Mary Ann Liebert, Inc., United States (1992).

D'Avino, P.O., et al., "The moulting hormone ecdysone is able to recognize target elements composed of direct repeats," *Molecular and Cellular Endocrinology* 113:1-9, Elsevier Ireland, Ltd., Ireland (1995).

Ding, W., et al., "Genomic structure and promoter characterization of the human *Sprouty4* gene, a novel regulator of lung morphogenesis," *The American Journal of Physiology Lung Cellular and Molecular Physiology* 287:L52-L29, The American Physiological Society, United States (2004).

Evans, R.M., "The Steroid and Thyroid Hormone Receptor Superfamily," *Science* 240:889-895, American Association for the Advancement of Science, United States (1988).

Felgner, P.L., and Ringold, G.M., "Cationic liposome-mediated transfection," *Nature* 337:387:388, Macmillan Magazines, Ltd., England (1989).

Felgner, P.L., et al., "Lipofection: A highly efficient, lipid-mediated DNA-transfection procedure," *Proceedings of the National Academy of Science* 84:7413-7417, The National Academy of Sciences, United States (1987).

Glass, C.K., et al., "Nuclear receptor coactivators," *Current Opinion in Cell Biology* 9:222-232, Current Biology Limited, United States (1997).

Hamer, D.H. and Walling, MJ., "Regulation In Vivo of a Cloned Mammalian Gene: Cadium Induces the Transcript of a Mouse Metallothionein Gene in SV40 Vectors," *Journal of Molecular and Applied Genetics* 1:273-288, Raven Press, United States (1982).

Higucho R. "Using PCT to Engineer DNA," in *PCR Technology: Principles and Applications for DNA Amplification*, Chapter 6, pp. 61-70, Stockton Press, United States (1989).

Horwitz, K.B., ete al., "Nuclear Receptor Coactivators and Corepressors," *Molecular Endocrinology* 10:1167-1177, The Endocrine Society, United States (1996).

Hutchinson, C.A., et al., "Mutagenesis at a Specific Position in a DNA Sequence," *The Journal of Biological Chemistry* 253:6551-6560, The American Society for Biochemistry and Molecualr Biology, United States (1978).

Hutchinson, C.A., et al., "A complete library of point substitution mutations in the glucocorticoid response element of mouse mammary tumor virus," *Proceedings of the National Academy of Science* 83:710-714, The National Academy of Sciences, United States (1986).

Karzenowski, D., et al., "Inducible control of transgene expression with ecdysone receptor: gene switches with high sensitivity, robust expression, and reduced size," *BioTechniques* 39:191-199, Informa Healthcare USA, Inc. England (2005).

Keown, W.A., et al., "Methods for Introducing DNA into Mammalian Cells," *Methods in Enzymology* 185:527-537, Academic Press, United States (1990).

Kim, J.-S., et al., "Design of TATA box-binding protein/zinc finger fusions for targeted regulation of gene expression," *Proceedings of the National Academy of Sciences* 94:3616-3620, The National Academy of Sciences, United States (1997).

Machy, P., et al., "Gene transfer from targeted liposomes to specific lymphoid cells by electropration," *Proceedings for the National Academy of Sciences* 85:8027-8031, The National Academy of Sciences, United States (1988).

(56) References Cited

OTHER PUBLICATIONS

McKnight, S.L., "Functional Relationships between Transcriptional Control Signals of the Thymidine Kinase Gene of Herpes Simplex Virus," *Cell* 31:355-365, Cell Press, United States (1982).

Oliphant, A.R., et al., "Cloning of random-sequence oligodeoxynucleotides," *Gene* 44:177-183, Elsevier Science Publishers, B.V., Netherlands (1986).

Palli, S.R., et al., "Improved ecdyson receptor-based inducible gene regulation system," *European Journal of Biochemistry* 270:1308-1315, FEBS, Netherlands (2003).

Reeck, G.R., et al., "'Homology' in Proteins and Nucleic Acids: A Terminology Muddle and a Way out of it," *Cell* 50: 667, Cell Press, United States (1987).

Sadowski, I., et al.,"GAL4-VP16 is an unusually potent transcriptional activator," *Nature* 335:563-564, Nature Publishing Group, England, (1988).

Thyagarajan, B., et al., "Site-Specific Genomic Integration in Mammalian Cells Mediated by Phage ΦC31 Integrase," *Molecular and Cellular Biology* 21:3926-3934, American Society for Microbiology, United States (2001).

Ulmer, J.B., et al., "Heterologous Protection Protein Against Influenza by Injection of DNA Encoding a Viral Protein," *Science* 259:1745-1749, American Association for the Advancement of Science, United States (1993).

Wu, G.Y. and Wu, C.H., "Receptor-mediated in Vitro Gene Transformation by a soluble DNA Carrier System," *Journal of Biological Chemistry* 262:4429-4432, The American Society of Biological Chemists, Inc., United States (1987).

Wilson, J.M., et al. "Hepatocyte-directed Gene Transfer in Vivo Leads to Transient Improvement of Hypercholesterolemia in Low Density Lipoprotein Receptor-deficient Rabbits," *The Journal of Biological Chemistry* 267:963-967, The American Society for Biochemistry and Molecular Biology, Inc., United States (1992).

Yao, T.-P., et al., "*Drosophila* ultraspiracle Modulates Ecdyson Receptor Function via Heterodimer Formation," *Cell* 71:63-72, Cell Press, United States(1992).

Yao, T.-P., et al., "Functional ecdysone receptor is the product of *EcR* and *Ultraspiracle* genes," *Nature* 366:476-479, Nature Publishing Group, England (1993).

Zoller, M.J. and Smith, M., "Oligonucleotide-Directed Mutagensis: A Simple Method Usng Two Oligonucleotide Primers and Single-Stranded DNA Template," *DNA* 3:479-488, Cold Spring Harbor Laboratory, United States (1984).

US 9,222,121 B2

METHODS AND COMPOSITIONS FOR DIAGNOSING DISEASE

REFERENCE TO SEQUENCE LISTING SUBMITTED ELECTRONICALLY

The content of the sequence listing text file (File Name: Sequence Listing.ST25.txt; Size: 107 KB bytes; and Date of Creation: Aug. 22, 2008) filed herewith with the application is incorporated herein by reference in its entirety.

BACKGROUND OF THE INVENTION

1. Field of the Invention

The present invention relates to methods and compositions for diagnosing a disease or disorder in a subject by introducing into cells of the subject a diagnostic gene switch construct and monitoring expression of a reporter gene. The invention further relates to methods and compositions for monitoring the progression of a disease or disorder or monitoring the effectiveness or toxicity of a treatment for a disease or disorder.

2. Background Art

Diagnostic tests for the presence of a disease in a subject have long been in existence, but researchers are constantly searching for improved tests exhibiting increased sensitivity (allowing earlier detection) and specificity (eliminating false positives and false negatives). Other desired characteristics for diagnostic tests include ease of use, rapid results, and the ability to constantly monitor progression of a disease or the effectiveness of ongoing treatment.

Thus, there is a need in the art for new diagnostic methods and compositions that provide these desired characteristics.

SUMMARY OF THE INVENTION

The present invention is based on a combination of the specificity and sensitivity provided by the use of disease specific promoters to detect a disease coupled with the regulatory control of a ligand-dependent gene switch system to provide diagnostic and monitoring methods. The present invention relates to methods and compositions for diagnosing a disease or disorder in a subject. The invention further relates to methods and compositions for monitoring the progression of a disease or disorder in a subject or monitoring the effectiveness or toxicity of an administered treatment for a disease or disorder in a subject.

One embodiment of the invention comprises methods of diagnosing a disease or disorder in a subject, comprising:
(a) introducing into cells of said subject (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor, to produce modified cells;
(2) administering ligand to said modified cells; and
(3) detecting reporter gene expression;
wherein expression of the reporter gene indicates that said subject has said disease or disorder.

In one embodiment, the diagnostic methods are carried out ex vivo in cells that have been isolated from said subject.

In one embodiment, the diagnostic methods are carried out by introducing the compositions of the invention into cells that have been isolated from said subject to produce modified cells, and the modified cells are re-introduced into said subject.

In one embodiment, the diagnostic methods are carried out in vivo.

In a further embodiment, the diagnostic methods are carried out using non-autologous cells, e.g., cells that are allogeneic or xenogeneic to the subject, and the modified non-autologous cells are introduced into the subject. In one embodiment, the non-autologous cells are surrounded by a barrier (e.g., encapsulated) prior to being introduced into the subject.

In one aspect of the invention, the gene switch is an ecdysone receptor (EcR)-based gene switch.

In one embodiment, the gene switch comprises a first transcription factor sequence under the control of a first diagnostic switch promoter and a second transcription factor sequence under the control of a second diagnostic switch promoter, wherein the proteins encoded by said first transcription factor sequence and said second transcription factor sequence interact to form a protein complex which functions as a ligand-dependent transcription factor.

In another aspect of the invention, said first transcription factor sequence encodes a protein comprising a heterodimer partner and a transactivation domain and said second transcription factor sequence encodes a protein comprising a DNA binding domain and a ligand-binding domain.

An additional embodiment of the invention relates to methods of monitoring the progression of a disease or disorder in a subject, comprising:
(a) introducing into cells of said subject (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor, to produce modified cells;
(b) administering ligand to said modified cells; and
(c) detecting reporter gene expression at least twice;
wherein a change in the level of expression of said reporter gene indicates progression of said disease or disorder in said subject.

A further embodiment of the invention relates to methods of monitoring the effectiveness of a treatment for a disease or disorder in a subject, comprising:
(a) administering said treatment to said subject;
(b) introducing into cells of said subject (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor, to produce modified cells;
(c) administering ligand to said modified cells; and
(d) detecting reporter gene expression at least twice;
wherein a change in the level of expression of said reporter gene indicates the effectiveness of said treatment.

Another embodiment of the invention relates to methods of monitoring the potential toxicity of an administered treatment for a disease or disorder in a subject, comprising:
(a) administering said treatment to said subject;

(b) introducing into cells of said subject (1) a polynucleotide encoding a gene switch, said gene switch comprising at least one transcription factor sequence, wherein said at least one transcription factor sequence encodes a ligand-dependent transcription factor, linked to a diagnostic switch promoter, wherein the activity of the promoter is modulated by factors found in cells that are being exposed to toxic conditions, and (2) a polynucleotide encoding a reporter gene linked to a promoter which is activated by said ligand-dependent transcription factor, to produce modified cells;
(c) administering ligand to said modified cells; and
(d) detecting reporter gene expression at least twice;
wherein a change in the level of expression of said reporter gene indicates the toxicity of said treatment.

Another embodiment of the invention relates to methods of monitoring the level of a factor that is being administered to a subject for treatment for a disease or disorder, comprising:
(a) administering said treatment to said subject;
(b) introducing into cells of said subject (1) a polynucleotide encoding a gene switch, said gene switch comprising at least one transcription factor sequence, wherein said at least one transcription factor sequence encodes a ligand-dependent transcription factor, linked to a diagnostic switch promoter, wherein the activity of the promoter is modulated by said factor that is being administered for treatment, and (2) a polynucleotide encoding a reporter gene linked to a promoter which is activated by said ligand-dependent transcription factor, to produce modified cells;
(c) administering ligand to said modified cells; and
(d) detecting reporter gene expression;
wherein the level of expression of said reporter gene indicates the level of the factor being administered for treatment.

In a further embodiment, each of the methods may be carried out using non-autologous cells, e.g., cells that are allogeneic or xenogeneic to the subject, and the modified non-autologous cells are administered to the subject. In one embodiment, the modified non-autologous cells are surrounded by a barrier (e.g., encapsulated) prior to being introduced into the subject.

One embodiment of the invention comprises methods of detecting transplant rejection in a subject that has received an organ or tissue transplant, comprising:
(a) introducing into cells of said organ or tissue transplant (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during transplant rejection, and (2) a polynucleotide encoding a reporter gene linked to a promoter which is activated by said ligand-dependent transcription factor, to produce modified cells;
(b) administering ligand to said modified cells; and
(c) detecting reporter gene expression;
wherein expression of the reporter gene indicates that transplant rejection has been detected.

An additional embodiment of the invention relates to methods of monitoring the progression of transplant rejection in a subject that has received an organ or tissue transplant, comprising:
(a) introducing into cells of said organ or tissue transplant (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during transplant rejection, and (2) a polynucleotide encoding a reporter gene linked to a promoter which is activated by said ligand-dependent transcription factor, to produce modified cells;
(b) administering ligand to said modified cells; and
(c) detecting reporter gene expression at least twice;
wherein a change in the level of expression of said reporter gene indicates progression of said transplant rejection in said subject.

In a further embodiment, the methods of detecting or monitoring transplant rejection may be carried out by introducing the polynucleotides of the invention into non-autologous cells, e.g., cells that are allogeneic or xenogeneic to the organ or tissue being transplanted, and the modified non-autologous cells are introduced to the organ or tissue prior to transplantation. In one embodiment, the modified non-autologous cells are surrounded by a barrier (e.g., encapsulated) prior to being introduced into the organ or tissue.

In the methods described above, in one embodiment, the polynucleotide encoding the gene switch and the polynucleotide encoding the reporter gene linked to a promoter are part of one larger polynucleotide, e.g., a vector. In another embodiment, the polynucleotide encoding the gene switch and the polynucleotide encoding the reporter gene linked to a promoter are separate polynucleotides.

The invention further relates to diagnostic gene switch constructs that are useful in the disclosed methods.

The invention additionally relates to vectors comprising the diagnostic gene switch constructs of the invention.

The invention also relates to kits for carrying out the methods of the invention, comprising, e.g., gene switch constructs, vectors, ligands, etc. In one embodiment, the kits may comprise cells (e.g., autologous or non-autologous cells) that may comprise the polynucleotides of the invention. The non-autologous cells may be surrounded by a barrier (e.g., encapsulated).

BRIEF DESCRIPTION OF THE DRAWINGS/FIGURES

FIG. 1 shows an embodiment of the diagnostic gene switch of the invention in which two transcription factor sequences encoding two separate portions of a ligand-dependent transcription factor are under the control of different promoters. "Dx-Switch Components" represents a gene switch; "AD" represents a transactivation domain; "DBD" represents a DNA binding domain; "LBD" represents a ligand binding domain; "StandardDx-Reporter" represents a reporter gene; and "P1" and "P2" represent two different disease- or disorder-responsive promoters. In an alternative embodiment of FIG. 1, "P1" is a constitutive promoter, and "P2" and "P3" are different disease- or disorder-responsive promoters.

FIG. 2 shows an embodiment of the diagnostic gene switch of the invention in which two transcription factor sequences encoding two separate portions of a ligand-dependent transcription factor are under the control of different promoters. "Dx-Switch Components" represents a gene switch; "AD" represents a transactivation domain; "DBD-A" represents a first DNA binding domain; "DBD-B" represents a second DNA binding domain; "LBD" represents a ligand binding domain; "StandardDx-Reporter-A" represents a first reporter gene; "StandardDx-Reporter-B" represents a second reporter gene; and "P1," "P2," and "P3" represent three different disease- or disorder-responsive promoters. In an alternative embodiment of FIG. 2, "P1" is a constitutive promoter; and "P2" and "P3" are different disease- or disorder-responsive promoters.

FIG. 3 shows an embodiment of the diagnostic gene switch of the invention in which two transcription factor sequences encoding two separate portions of a ligand-dependent transcription factor are under the control of different diagnostic switch promoters. "Dx-Switch Components" represents a gene switch; "AD" represents a transactivation domain; "DBD" represents a DNA binding domain; "LBD" represents a ligand binding domain; "StandardDx-Reporter" represents a reporter gene; and "P1," "P2," "P3," and "P4" represent four different disease- or disorder-responsive promoters.

FIG. 4 shows an embodiment of the diagnostic gene switch of the invention in which two transcription factor sequences encoding two separate portions of a ligand-dependent transcription factor are under the control of different promoters and a control reporter gene is present. "Dx-Switch Components" represents a gene switch; "AD" represents a transactivation domain; "DBD-A" represents a first DNA binding domain; "DBD-B" represents a second DNA binding domain; "LBD" represents a ligand binding domain; "StandardDx-Reporter-A" represents a first reporter gene; "Control-Reporter-B" represents a second reporter gene; and "P1" and "P2" represent two different disease- or disorder-responsive promoters; and "P3" and "P4" represent two different control promoters. In an alternative embodiment of FIG. 4, "P3" and "P4" are constitutive promoters.

Figure 10:
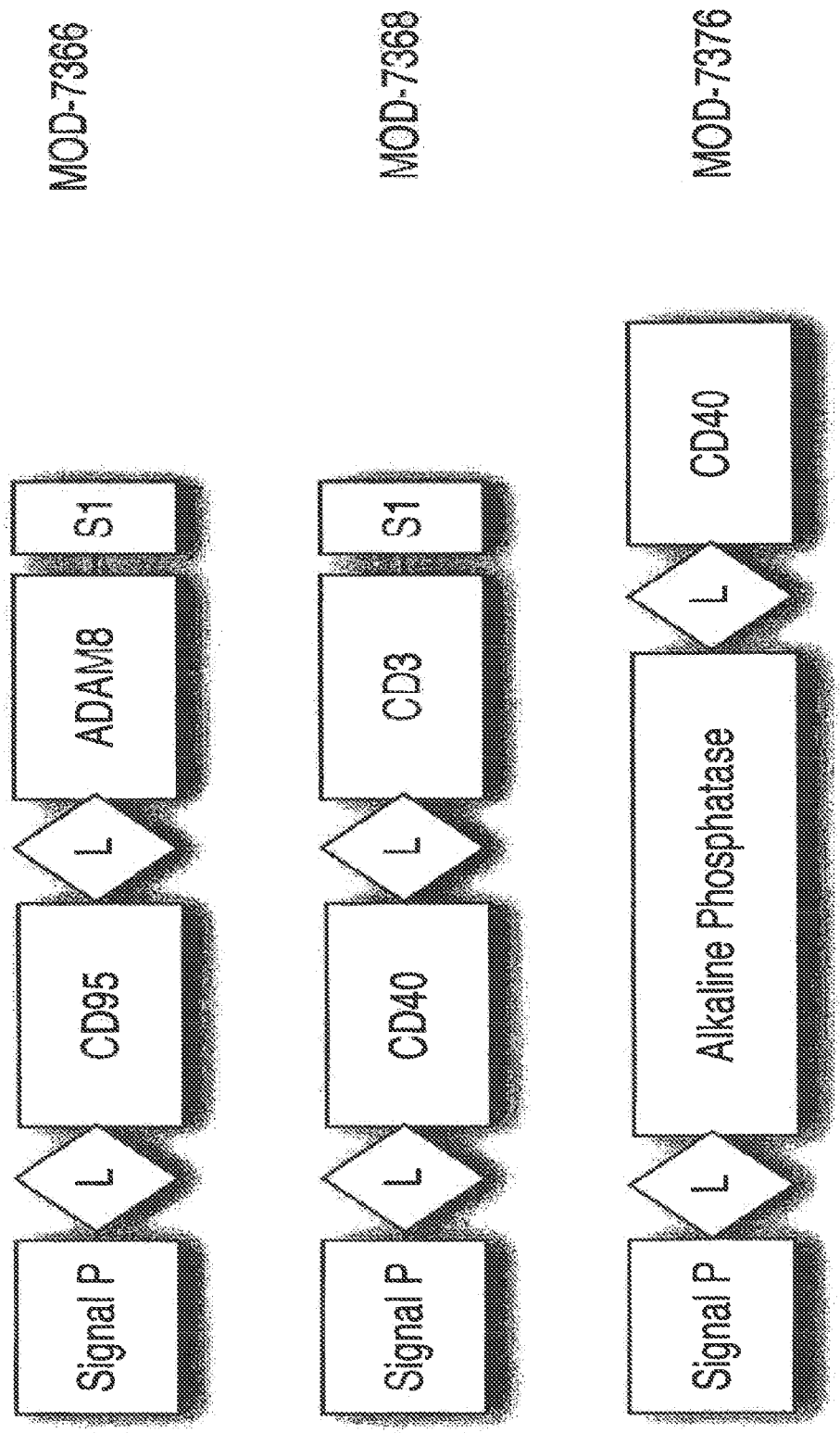

FIG. 10 shows embodiments of the serum-based reporters that are designed to exhibit no immunogenic profile when expressed within the human body. These reporters are made up of human based amino acid sequences that are present either on the cell surface or within the serum naturally. Hence, these reporters are not immunogenic nor are they subject to immune attack when expressed in the human body. In one embodiment, serum-based reporters are dual epitope reporter, for e.g., CD95-ADAM8 reporter (SEQ ID NOs.: 10-11), CD40-CD3 reporter (SEQ ID NOs.: 12-13), CD28-CD3 reporter (SEQ ID. NOs.: 16-17) and CD28-CD40 reporter (SEQ ID NOs.: 18-19) that allows ELISA based capture and detection. The designs utilize a signal peptide (Signal P) for transport into the secretory pathway, followed by epitopes from cell surface antigens with linkers (L). In alternative embodiments, different combinations of linkers and epitopes are used for each design. In another embodiment, the serum-based reporter is an alkaline phosphatase reporter, for e.g., alkaline phosphatase—c terminal CD40 reporter (SEQ ID NOs.: 14-15), that allows immunocapture followed by enzymatic detection of reporter activity. Alkaline phosphatase reporters utilize the tissue non-specific alkaline phosphatase for an enzymatic reporter that can be secreted. An epitope from a cell surface antigen is included at the carboxy terminus for immunocapture prior to measurement of alkaline phosphatase activity. In additional embodiments of FIG. 10, additional alkaline phosphatase reporters are: alkaline phosphatase—amiono terminal CD40 reporter (SEQ ID NOs.: 20-21) and alkaline phosphatase—c terminal CD28 reporter (SEQ ID. NOs.: 22-23).

DETAILED DESCRIPTION OF THE INVENTION

The invention relates to methods and compositions for using a gene switch for the diagnosis of diseases or disorders in a subject. The invention further relates to methods and compositions for monitoring the progression of diseases or disorders or the treatment thereof in a subject. The methods of the invention can be carried out either ex vive (by introducing the gene switch into isolated cells of a subject) or in vive (by introducing the gene switch into isolated cells of a subject and reintroducing the cells to the subject or by introducing the gene switch directly into cells of the subject). In another embodiment, the cells harboring the gene switch may be non-autologous cells (e.g., allogeneic or xenogeneic cells). The non-autologous cells may be surrounded by a barrier that prevents the non-autologous cells from raising an immune response after introduction and/or prevents the non-autologous cells from escaping from the site of introduction. The methods of the invention involve the use of a gene switch in which expression of a ligand-dependent transcription factor is under the control of one or more diagnostic switch promoters. The methods and compositions described herein provide a highly sensitive and highly specific diagnostic technique in which the timing of the diagnostic step is controlled by administration of ligand to cells comprising the gene switch, permitting optimal detection of the presence of a disease or disorder as well as continuous or intermittent monitoring of the progression of a disease or disorder or the effectiveness or toxicity of a treatment.

The following definitions are provided and should be helpful in understanding the scope and practice of the present invention.

The term "isolated" for the purposes of the present invention designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

The term "purified," as applied to biological materials does not require the material to be present in a form exhibiting absolute purity, exclusive of the presence of other compounds. It is rather a relative definition.

"Nucleic acid," "nucleic acid molecule," "oligonucleotide," and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA.

The term "fragment," as applied to polynucleotide sequences, refers to a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of; oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000, 1500, 2000, 3000, 4000, 5000, or more consecutive nucleotides of a nucleic acid according to the invention.

As used herein, an "isolated nucleic acid fragment" refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to a polynucleotide comprising nucleotides that encode a functional molecule, including functional molecules produced by transcription only (e.g., a bioactive RNA species) or by transcription and translation (e.g., a polypeptide). The term "gene" encompasses cDNA and genomic DNA nucleic acids. "Gene" also refers to a nucleic acid fragment that expresses a specific RNA, protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous DNA" refers to DNA not naturally located in the cell, or in a chromosomal site of the cell. The heterologous DNA may include a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook et al. in *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the present invention also includes isolated nucleic acid fragments that are complementary to the complete sequences as disclosed or used herein as well as those substantially similar nucleic acid sequences.

In one embodiment of the invention, polynucleotides are detected by employing hybridization conditions comprising a hybridization step at $T_m$ of 55° C., and utilizing conditions as set forth above. In other embodiments, the $T_m$ is 60° C., 63° C., or 65° C.

Post-hybridization washes also determine stringency conditions. One set of conditions uses a series of washes starting with 6×SSC, 0.5% SDS at room temperature for 15 minutes (min), then repeated with 2×SSC, 0.5% SDS at 45° C. for 30 min, and then repeated twice with 0.2×SSC, 0.5% SDS at 50° C. for 30 min. A preferred set of stringent conditions uses higher temperatures in which the washes are identical to those above except for the temperature of the final two 30 min washes in 0.2×SSC, 0.5% SDS is increased to 60° C. Another preferred set of highly stringent conditions uses two final washes in 0.1×SSC, 0.1% SDS at 65° C.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In one embodiment of the invention, polynucleotides are detected by employing hybridization conditions comprising a hybridization step in less than 500 mM salt and at least 37° C., and a washing step in 2×SSPE at a temperature of at least 63° C. In another embodiment, the hybridization conditions comprise less than 200 mM salt and at least 37° C. for the hybridization step. In a further embodiment, the hybridization conditions comprise 2×SSPE and 63° C. for both the hybridization and washing steps.

In another embodiment, the length for a hybridizable nucleic acid is at least about 10 nucleotides. Preferably a minimum length for a hybridizable nucleic acid is at least about 15 nucleotides; e.g., at least about 20 nucleotides; e.g., at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a short nucleic acid that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, for DNA sequencing, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" refers to an oligonucleotide that hybridizes to a target nucleic acid sequence to create a double stranded nucleic acid region that can serve as an initiation point for DNA synthesis under suitable conditions. Such primers may be used in a polymerase chain reaction or for DNA sequencing.

"Polymerase chain reaction" is abbreviated PCR and refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and refers to an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" refers to a double-stranded DNA sequence that encodes a polypeptide and can be transcribed and translated into a polypeptide in a cell in vitro or in vive when placed under the control of suitable regulatory sequences. "Suitable regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and refers to a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (← →) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→ ←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→ →) or (5'→3'5'→3').

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to a reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" are used interchangeably and refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes both viral and nonviral vehicles for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. Another example of vectors that are useful in the present invention is the UltraVector™ Production System (Intrexon Corp., Blacksburg, Va.) as described in WO 2007/038276, incorporated herein by reference. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include, but are not limited to, retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" refers to a "replicon," which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector"). Cloning vectors may comprise one or more sequences that can be used for selection of cells comprising the vector and/or one or more multiple cloning sites for insertion of sequences of interest.

The term "expression vector" refers to a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving expression of these genes can be used in an expression vector, including but not limited to, viral promoters, bacterial promoters, animal promoters, mammalian promoters, synthetic promoters, constitutive promoters, tissue specific promoters, pathogenesis or disease related promoters, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art including, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Feigner et al., *Proc. Natl. Acad. Sci. USA.* 84:7413 (1987); Mackey et al., *Proc. Natl. Acad. Sci. USA* 85:8027 (1988); and Ulmer et al., *Science* 259:1745 (1993)). The use of cationic lipids may promote encapsulation of negatively charged nucleic acids, and also promote fusion with negatively charged cell membranes (Feigner et al., *Science* 337:387 (1989)). Particularly useful lipid compounds and compositions for transfer of nucleic acids are described in WO95/18863, WO096/17823 and U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey et al. 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., *Hum. Gene Ther.* 3:147 (1992); and Wu et al., *J. Biol. Chem.* 262:4429 (1987)).

The term "transfection" refers to the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

In addition, the recombinant vector comprising a polynucleotide according to the invention may include one or more origins for replication in the cellular hosts in which their amplification or their expression is sought, markers or selectable markers.

The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter and "promoter sequence" are used interchangeably and refer to a DNA sequence capable of controlling the transcription of a nucleic acid. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths may have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of transcription factors that recruit RNA polymerase-mediated transcription.

"Diagnostic switch promoter" refers to a promoter the activity of which is modulated by a factor in a manner that can be used as a diagnostic in the present invention. The term encompasses promoters that increase or decrease expression of a coding sequence during a disease or disorder as a change in promoter activity in either direction will be diagnostic. The term includes, without limitation, disease-specific promoters, promoters responsive to particular physiological or pathological conditions, and promoters responsive to specific biological molecules. Diagnostic switch promoters can comprise the sequence of naturally occurring promoters, modified sequences derived from naturally occurring promoters, or synthetic sequences (e.g., insertion of a response element into a promoter sequence to alter the responsiveness of the promoter).

A "coding sequence" is a DNA sequence that encodes a polypeptide or a RNA (e.g., a functional RNA).

A coding sequence is "under the control" of transcriptional and translational control sequences in a cell when RNA polymerase transcribes the coding sequence into RNA. If the coding sequence is a protein coding sequence, the primary RNA transcript is then further processed (e.g., trans-RNA spliced (if the coding sequence contains introns) and polyadenylated), exported to the cytoplasm, and translated into the protein encoded by the coding sequence. Non-protein-coding bioactive RNA species (including, but not limited to RNAi or microRNAs) can be functional in the nucleus as a primary transcript, a spliced transcript (with or without polyadenylation), and/or an excised intron; or can exert bioactivity in extra-nuclear cellular regions as any RNA form that is exported from the nucleus.

"Transcriptional and translational control sequences" refer to DNA regulatory sequences, such as promoters, enhancers, terminators, and the like, that provide for the expression of a coding sequence in a host cell. In eukaryotic cells, polyadenylation signals are control sequences.

The term "response element" refers to one or more cis-acting DNA elements which confer responsiveness on a promoter mediated through interaction with the DNA-binding domains of a transcription factor. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the transcription factor binds, in the presence or absence of a ligand, to the DNA sequence of a response element to initiate or suppress transcription of downstream gene(s) under the regulation of this response element. Examples of DNA sequences for response elements of the natural ocdysone receptor include: RRGG/TTCANTGAC/ACYY (SEQ ID NO: 1) (see Cherbas et. al., *Genes Dev.* 5:120 (1991)); AGGTCAN$_{(n)}$ AGGTCA, where N$_{(n)}$ can be one or more spacer nucleotides (SEQ ID NO: 2) (see D'Avino et al., *Mol. Cell. Endocrinol.* 113:1 (1995)); and GGGTTGAATGAATTT (SEQ ID NO: 3) (see Antoniewski et al., *Mol. Cell Biol.* 14:4465 (1994)).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein refers to the production of RNA (e.g., sense RNA, antisense RNA, microRNA, messenger RNA, heterologous nuclear RNA, ribosomal RNA, small interfering RNA, ribozymes, etc.) by transcription of a nucleic acid or polynucleotide. Expression may also include translation of mRNA into a protein or polypeptide.

The terms "cassette," "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and a ligand-dependent transcription factor-based system which, in the presence of one or more ligands, modulates the expression of a gene into which the response element and promoter are incorporated.

The term "ecdysone-based," with respect to a gene switch, refers to a gene switch comprising at least a functional part of a naturally occurring or synthetic ecdysone receptor ligand binding domain and which regulates gene expression in response to a ligand that binds to the ecdysone receptor ligand binding domain.

The terms "modulate" and "modulates" mean to induce, reduce or inhibit nucleic acid or gene expression, resulting in the respective induction, reduction or inhibition of protein or polypeptide production.

The polynucleotides or vectors according to the invention may further comprise at least one promoter suitable for driving expression of a gene in a host cell.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In a one embodiment of the invention, the termination control region may be comprised or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" refers to a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" refers to a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

"Polypeptide," "peptide" and "protein" are used interchangeably and refer to a polymeric compound comprised of covalently linked amino acid residues.

An "isolated polypeptide," "isolated peptide" or "isolated protein" refer to a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one wild-type or naturally occurring amino acid with a different amino acid relative to the wild-type or naturally occurring polypeptide. A substitution mutant polypeptide may comprise only one wild-type or naturally occurring amino acid substitution and may be referred to as a "point mutant" or a "single point mutant" polypeptide. Alternatively, a substitution mutant polypeptide may comprise a substitution of two or more wild-type or naturally occurring amino acids with two or more amino acids relative to the wild-type or naturally occurring polypeptide. According to the invention, a Group H nuclear receptor ligand binding domain polypeptide comprising a substitution mutation comprises a substitution of at least one wild-type or naturally occurring amino acid with a different amino acid relative to the wild-type or naturally occurring Group H nuclear receptor ligand binding domain polypeptide.

When the substitution mutant polypeptide comprises a substitution of two or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wild-type amino acids (a substitution+insertion mutation).

Substitution mutants may be described using an abbreviated nomenclature system to indicate the amino acid residue and number replaced within the reference polypeptide sequence and the new substituted amino acid residue. For example, a substitution mutant in which the twentieth ($20^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson et al., *J. Biol. Chem.* 253:6551 (1978); Zoller et al., *DNA* 3:479 (1984); Oliphant et al, *Gene* 44:177 (1986); Hutchinson et al., *Proc. Natl. Acad. Sci. USA* 83:710 (1986)), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Prin-*

*ciples and Applications for DNA Amplification*, H. Erlich, ed., Stockton Press, Chapter 6, pp. 61-70).

The term "fragment," as applied to a polypeptide, refers to a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 or more amino acids.

A "variant" of a polypeptide or protein refers to any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. In one embodiment, a variant polypeptide comprises at least about 14 amino acids.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., *Cell* 50:667 (1987)). Such proteins (and their encoding genes) have sequence homology, as reflected by their high degree of sequence similarity. However, in common usage and in the present application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al, *Cell* 50:667 (1987)). In one embodiment, two DNA sequences are "substantially homologous" or "substantially similar" when at least about 50% (e.g., at least about 75%, 90%, or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see e.g., Sambrook et al., 1989, supra).

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the present invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the present invention are those nucleic acid fragments whose DNA sequences are at least about 70%, 80%, 90% or 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, *Version* 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403 (1993)); available at ncbi.nlm.nih.gov/BLAST/). In general, a sequence often or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); Sequence Analysis in Molecular Biology (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using sequence analysis software such as the Megalign program of the LASERGENE bioinformatics computing suite (DNASTAR Inc., Madison, Wis.). Multiple alignment of the sequences may be performed using the Clustal method of alignment (Higgins et al., *CABIOS.* 5:151 (1989)) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software includes, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403 (1990)), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentially of the actual modulation. Preferably, modulation of each individually operable gene regulation system effects a change in gene expression at least 2-fold greater than all other operable systems in the cell, tissue, or organism, e.g., at least 5-fold, 10-fold, 100-fold, or 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal." The present invention is useful to search for orthogonal ligands and orthogonal receptor-based gene expression systems such as those described in US 2002/0110861 A1, which is incorporated herein by reference in its entirety.

The term "exogenous gene" means a gene foreign to the subject, that is, a gene which is introduced into the subject through a transformation process, an unmutated version of an endogenous mutated gene or a mutated version of an endogenous unmutated gene. The method of transformation is not critical to this invention and may be any method suitable for the subject known to those in the art. Exogenous genes can be either natural or synthetic genes and therapeutic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells into the subject. The term "therapeutic gene" means a gene which imparts a beneficial function to the host cell in which such gene is expressed.

The term "ecdysone receptor complex" generally refers to a heterodimeric protein complex having at least two members of the nuclear receptor family, ecdysone receptor ("EcR") and ultraspiracle ("USP") proteins (see Yao et al., *Nature* 366:476 (1993)); Yao et al., *Cell* 71:63 (1992)). The functional EcR complex may also include additional protein(s) such as immunophilins. Additional members of the nuclear receptor family of proteins, known as transcriptional factors (such as DHR38, betaFZ-1 or other insect homologs), may also be ligand dependent or independent partners for EcR and/or USP. The EcR complex can also be a heterodimer of EcR protein and the vertebrate homolog of ultraspiracle protein, retinoic acid-X-receptor ("RXR") protein. The term EcR complex also encompasses homodimer complexes of the EcR protein or USP.

An EcR complex can be activated by an active ecdysteroid or non-steroidal ligand bound to one of the proteins of the complex, inclusive of EcR, but not excluding other proteins of the complex. As used herein, the term "ligand," as applied to EcR-based gene switches, describes small and soluble molecules having the capability of activating a gene switch to stimulate expression of a polypeptide encoded therein. Examples of ligands include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol -3-sulfate (ECHS), 7-ketocholesterol-3-sulfate, farnesol, bile acids, 1,1-biphosphonate esters, juvenile hormone III, and the like. Examples of diacylhydrazine ligands useful in the present invention include RG-115819 (3,5-Dimethyl-benzoic acid N-(1-ethyl-2,2-dimethyl-propyl)-N'-(2-methyl-3-methoxy-benzoyl)-hydrazide), RG-115830 (3,5-Dimethyl-benzoic acid N-(1-tert-butyl-butyl)-N'-(2-ethyl-3-methoxy-benzoyl)-hydrazide), and RG-115932 ((R)-3,5-Dimethyl-benzoic acid N-(1-tert-butyl-butyl)-N'-(2-ethyl-3-methoxy-benzoyl)-hydrazide). See U.S. application Ser. No. 12/155,111.

The EcR complex includes proteins which are members of the nuclear receptor superfamily wherein all members are characterized by the presence of an amino-terminal transactivation domain ("TA"), a DNA binding domain ("DBD"), and a ligand binding domain ("LBD") separated by a hinge region. Some members of the family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the EcR complex may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the EcR. As a result, they are "substantially insensitive" to the ligands of this invention. Thus, the ligands useful in this invention will have negligible physiological or other effects on transformed cells, or the whole organism. Therefore, cells can grow and express the desired product, substantially unaffected by the presence of the ligand itself.

The term "subject" means an intact insect, plant or animal. It is also anticipated that the ligands will work equally well when the subject is a fungus or yeast. When the subject is an intact animal, preferably the animal is a vertebrate, most preferably a mammal.

EcR ligands, when used with the EcR complex which in turn is bound to the response element linked to an exogenous gene (e.g., a reporter gene), provide the means for external temporal regulation of expression of the exogenous gene. The order in which the various components bind to each other, that is, ligand to receptor complex and receptor complex to response element, is not critical. Typically, modulation of expression of the exogenous gene is in response to the binding of the EcR complex to a specific control, or regulatory, DNA element. The EcR protein, like other members of the nuclear receptor family, possesses at least three domains, a transactivation domain, a DNA binding domain, and a ligand binding domain. This receptor, like a subset of the nuclear receptor family, also possesses less well-defined regions responsible for heterodimerization properties. Binding of the ligand to the ligand binding domain of EcR protein, after heterodimerization with USP or RXR protein, enables the DNA binding domains of the heterodimeric proteins to bind to the response element in an activated form, thus resulting in expression or suppression of the exogenous gene. This mechanism does not exclude the potential for ligand binding to either EcR or USP, and the resulting formation of active homodimer complexes (e.g. EcR+EcR or USP+USP). In one embodiment, one or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988) or LexA protein from *E. coli* (see Brent et al., *Cell* 43:729 (1985)) to accommodate chimeric EcR complexes. Another advantage of chimeric systems is that they allow choice of a promoter used to drive the exogenous gene according to a desired end result. Such double control can be particularly important in areas of gene therapy, especially when cytotoxic proteins are produced, because both the timing of expression as well as the cells wherein expression occurs can be controlled. When exogenous genes, operatively linked to a suitable promoter, are introduced into the cells of the subject, expression of the exogenous genes is controlled by the presence of the ligand of this invention. Promoters may be constitutively or inducibly regulated or may be tissue-specific (that is, expressed only in a particular type of cell) or specific to certain developmental stages of the organism.

Numerous genomic and cDNA nucleic acid sequences coding for a variety of polypeptides, such as transcription factors and reporter genes, are well known in the art. Those skilled in the art have access to nucleic acid sequence information for virtually all known genes and can either obtain the nucleic acid molecule directly from a public depository, the institution that published the sequence, or employ routine methods to prepare the molecule.

For in vivo use, the ligands described herein may be taken up in pharmaceutically acceptable carriers, such as, for example, solutions, suspensions, tablets, capsules, ointments, elixirs, and injectable compositions. Pharmaceutical compositions may contain from 0.01% to 99% by weight of the ligand. Compositions may be either in single or multiple dose forms. The amount of ligand in any particular pharmaceutical composition will depend upon the effective dose, that is, the dose required to elicit the desired gene expression or suppression.

Suitable routes of administering the pharmaceutical preparations include oral, rectal, topical (including dermal, buccal and sublingual), vaginal, parenteral (including subcutaneous, intramuscular, intravenous, intradermal, intrathecal and epidural) and by naso-gastric tube. It will be understood by those skilled in the art that the preferred route of administration will depend upon the condition being diagnosed and may vary with factors such as the condition of the recipient.

One embodiment of the invention comprises methods of diagnosing a disease or disorder in a subject, comprising:
(a) introducing into cells of said subject (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor, to produce modified cells;
(b) administering ligand to said modified cells; and
(c) detecting reporter gene expression;
wherein expression of the reporter gene indicates that said subject has said disease, disorder, or condition.

In one embodiment, the diagnostic methods are carried out ex vivo in cells that have been isolated from said subject.

In one embodiment, the diagnostic methods are carried out by introducing the compositions of the invention into cells that have been isolated from said subject to produce modified cells, and the modified cells are re-introduced into said subject.

In one embodiment, the diagnostic methods are carried out in vivo.

In a different embodiment, the diagnostic methods may be carried out using non-autologous cells, e.g., cells that are allogeneic or xenogeneic to the subject, instead of autologous cells from the subject. The polynucleotides may be introduced into the non-autologous cells ex vivo to produce modified cells and the modified cells may then be introduced into the subject. The non-autologous cells may be any cells that are viable after transplantation into a subject, including, without limitation, stem cells (such as embryonic stem cells or hematopoietic stem cells) and fibroblasts.

One embodiment of the invention relates to methods of diagnosing a disease or disorder in a subject, comprising:
(a) introducing into non-autologous cells (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor, to produce modified cells;
(b) introducing said modified cells into said subject;
(c) administering ligand to said modified cells; and
(d) detecting reporter gene expression;
wherein expression of said reporter gene indicates that said subject has said disease or disorder.

In one aspect of this embodiment, the modified cells are surrounded by a barrier (e.g., encapsulated) prior to being introduced into the subject. The encapsulated cells will function as an implantable biosensor. In one embodiment, encapsulation of cells and methods for making them are provided, which provide improved structural characteristics and immune protection. Such encapsulated cells will withstand mechanical, chemical or immune destruction within the host, and will additionally provide for free permeability to nutrients, ions, oxygen, and other materials needed to both maintain the cell and support normal metabolic functions. In one embodiment, the encapsulated cells are impermeable to bacteria, lymphocytes, and large proteins of the type responsible for immunochemical reactions. In one embodiment, the barrier will also function to prevent the non-autologous cells from escaping from the site of introduction, e.g., rogue cells that might cause harm to the subject if allowed to circulate. In one embodiment, the barrier is a selectively permeable barrier, e.g., a barrier that is permeable to small molecules such as hormones and small peptides but impermeable to larger polypeptides such as antibodies. For example, the barrier may be impermeable to molecules with a molecular weight greater than about 100,000, about 50,000, about 25,000, about 10,000, about 5,000 or about 1,000 daltons.

Two encapsulation methods, microencapsulation and macroencapsulation, are known in the art. Typically, microencapsulated cells are sequestered in a small spherical container, whereas macroencapsulated cells are entrapped in a larger non-spherical membrane. For encapsulation, living cells and other sensitive materials are treated under sufficiently mild conditions allowing the cells or biomaterial to remain substantially unaffected by the encapsulation process, yet permitting the formation of a capsule of sufficient strength to exist over long periods of time.

In one embodiment, the cells are encapsulated within a biocompatible semi-permeable membrane. The term "biocompatible" as used herein refers collectively to both the intact capsule and its contents. Specifically, it refers to the capability of the implanted intact encapsulated cell to avoid detrimental effects of the body's various protective systems, such as immune system or foreign body fibrotic response, and remain functional for a significant period of time.

The capsules of the present invention are especially useful for the administration of cells by injection, implantation or transplantation to a subject. Living cells can be encapsulated in a variety of gels, to form implantable devices, e.g., microbeads or microspheres to physically isolate the cells once implanted into a host. To prevent entry of smaller molecular weight substances such as antibodies and complement (with a molecular weight of about 150 kDa) into these mircoparticles, they can be coated with a material such as poly-L-lysine, chitosan, or PAN-PVC, which provides an outer shell with a controlled pore size or they can be treated by e.g., cross-linking, to control their internal porosity. Additional examples of useful materials include conventional biocompatible materials made up of natural or synthetic polymers or co-polymers, such as alginate, poly-L-lysine-alginate, collagen, gelatin, laminin, methyl methacrylate, hydroxyethyl methacrylate, MATRIGEL, VIRTOGEN, polyvinylalcohol, agarose, polyethylene glycol, hydrogels, polylactic acid, polyglycolic acid, poly(lactide-co-glycolide), polyhydroxybutyrate-polyhydroxyvalerate, copolymer, poly(lactide-co-caprolactone), polyesteramides, polyorthoesters, poly 13-hydroxybutyric acid, polyanhydrides, polyethylene terephthalate, polyetrafluoroethylene, polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, and poly(acrylonitrile/covinyl chloride).

In one embodiment, the cells are isolated and suspended in liquid medium and then encapsulated by a supporting matrix, e.g., a hydrogel matrix to form a microbead. This microbead may serve as a core of an implantable device. The core will maintain a proper cell distribution, provide strength, and enhance cell viability, longevity, and function. The core will also contribute to immunoisolation. The core will also protect the internal particle from direct cell-cell interactions that can elicit an undesirable host response.

The barrier may contain multiple layers, e.g., where each layer serves a different purpose (e.g., support, control of permeability). Barriers may also comprise contrast agents or other properties that render the barrier imageable (e.g., by x-ray, sonography, etc.) to ensure proper positioning of the implanted cells. Examples of barrier systems useful for cell implantation are described in U.S. Pat. Nos. 7,226,978, RE39,542 (agarose), U.S. Pat. Nos. 6,960,351, 6,916,640, 6,911,227 (polyethylene glycol), U.S. Pat. Nos. 6,818,018, 6,808,705, 6,783,964, 6,762,959, 6,727,322, 6,610,668 (poly-14-N-acetylglucosamine (p-GlcNAc) polysaccharide), U.S. Pat. Nos. 6,558,665, RE38,027, 6,495,161, 6,368,612, 6,365,385, 6,337,008, 6,306,454 (polyalkylene), U.S. Pat. Nos. 6,303,355, 6,287,558 (gel super matrix), U.S. Pat. Nos. 6,281,015, 6,264,941, 6,258,870, 6,180,007, 6,126,936 (polyamine acid), U.S. Pat. Nos. 6,123,700, 6,083,523, 6,020,200, 5,916,790, 5,912,005, 5,908,623, 5,902,745, 5,858,746, 5,846,530 (polysaccaharides), U.S. Pat. Nos. 5,843,743, 5,837,747, 5,837,234, 5,834,274, 5,834,001, 5,801,033, 5,800,829, 5,800,828, 5,798,113, 5,788,988, 5,786,216, 5,773,286, 5,759,578, 5,700,848, 5,656,481, 5,653,975, 5,648,099, 5,550,178, 4,806,355, 4,689,293, 4,680,174, 4,673,566, 4,409,331, 4,352,883, and U.S. Patent Application Publications 2006/0263405 (alginate/polymer) and 2004/0005302 (alignate-poly-L-lysine), each incorporated herein by references in its entirety.

In one embodiment, the polynucleotide encoding the gene switch and the polynucleotide encoding the reporter gene linked to a promoter are part of one larger polynucleotide, e.g., a vector. In another embodiment, the polynucleotide encoding the gene switch and the polynucleotide encoding the reporter gene linked to a promoter are separate polynucleotides.

The subject on which the diagnostic methods are carried out may be any subject for which a diagnosis is desired. For example, the subject may be one that is exhibiting one or more symptoms of a disease or disorder. The subject may also be one that is predisposed to a disease or disorder, e.g., due to genetics, family history, or environmental exposure. The subject may be a member of the general public, e.g., as part of a screening for the prevalence of a disease or disorder in a population.

The disease or disorder to be diagnosed by the methods of the invention may be any disease or disorder for which one or more diagnostic switch promoters are available. Examples of diseases or disorders which may be diagnosed by the methods of the invention include, without limitation, hyperproliferative diseases (e.g., cancer), cardiovascular diseases, neural diseases, autoimmune diseases, graft versus host disease, transplant rejection, bone diseases, gastrointestinal diseases, blood diseases, metabolic diseases, inflammatory diseases, and infections.

One embodiment of the invention relates to methods of preparing modified cells for diagnosing a disease or disorder in a subject, comprising introducing into cells of said subject (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor, to produce modified cells.

Another embodiment of the invention relates to methods of diagnosing a disease or disorder in a subject, comprising:

(a) administering ligand to modified cells of said subject; and (b) detecting reporter gene expression;

wherein expression of said reporter gene indicates that said subject has said disease or disorder, and wherein said modified cells of said subject comprise (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor.

The diagnostic switch promoters of the invention may be any promoter that is useful for diagnosing a specific disease or disorder, monitoring the progression of a disease, or monitoring the effectiveness or toxicity of a treatment. Examples include, without limitation, promoters of genes that exhibit increased or decreased expression only during a specific disease or disorder and promoters of genes that exhibit increased or decreased expression under specific cell conditions (e.g., proliferation, apoptosis, change in pH, oxidation state, oxygen level). In some embodiments where the gene switch comprises more than one transcription factor sequence, the specificity of the diagnostic methods can be increased by combining a disease- or condition-specific promoter with a tissue- or cell type-specific promoter to limit the tissues in which a diagnostic measurement occurs. Thus, tissue- or cell type-specific promoters are encompassed within the definition of diagnostic switch promoter.

As an example of disease-specific promoters, useful promoters for diagnosing cancer include the promoters of oncogenes. Examples of classes of oncogenes include, but are not limited to, growth factors, growth factor receptors, protein kinases, programmed cell death regulators and transcription factors. Specific examples of oncogenes include, but are not limited to, sis, erb B, erb B-2, ras, abl, myc and bcl-2 and TERT. Examples of other cancer-related genes include tumor associated antigen genes and other genes that are overexpressed in neoplastic cells (e.g., MAGE-1, carcinoembryonic antigen, tyrosinase, prostate specific antigen, prostate specific membrane antigen, p53, MUC-1, MUC-2, MUC-4, HER-2/neu, T/Tn, MART-1, gp100, GM2, Tn, sTn, and Thompson-Friedenreich antigen (TF)).

Examples of promoter sequences and other regulatory elements (e.g., enhancers) that are known in the art and are useful as diagnostic switch promoters in the present invention are disclosed in the references listed in Tables 1 and 2, along with the disease/disorder (Table 1) or tissue specificity (Table 2) associated with each promoter. The promoter sequences disclosed in these references are herein incorporated by reference in their entirety.

TABLE 1

| Promoter Sequence | Disease/Disorder | Patent/Published Application No. |
|---|---|---|
| Her-2/neu (ERBB2/c-erbB-2) | cancer | 5,518,885 |
| osteocalcin | calcified tumors | 5,772,993 |
| stromelysin-1 | cancer | 5,824,794 |
| prostate specific antigen | prostate cancer | 5,919,652 |
| human sodium-iodide symporter | thyroid carcinoma | 6,015,376 |
| H19, IF-1, IGF-2 | cancer | 6,306,833 |
| thymosin β15 | breast, pancreatic, prostate cancer | 6,489,463 |
| T cell factor | cancer | 6,608,037 |
| cartilage-derived retinoic acid-sensitive protein | chondrosarcoma, mammary tumor | 6,610,509 |
| insulin | pancreatic cancer | 6,716,824 |
| PEG-3 | cancer | 6,737,523 |
| telomerase reverse transcriptase | cancer | 6,777,203 |
| melanoma differentiation associated gene-7 | cancer | 6,841,362 |
| prostasin | cancer | 6,864,093 |
| telomerase catalytic subunit; cyclin-A | cancer | 6,936,595 |
| midkine; c-erbB-2 | cancer | 7,030,099 |
| prostate-specific membrane antigen | prostate cancer | 7,037,647 |
| p51 | cancer | 7,038,028 |
| telomerase RNA | cancer | 7,084,267 |
| prostatic acid phosphatase | prostate cancer | 7,094,533 |
| PCA3$_{dd3}$ | prostate cancer | 7,138,235 |
| DF3/MUC1 | cancer | 7,247,297 |
| hex II | cancer | 2001/0011128 |
| cyclooxygenase-2 | cancer | 2002/0107219 |
| super PSA | prostate cancer | 2003/0078224 |
| skp2 | cancer | 2003/0109481 |
| PRL-3 | metastatic colon cancer | 2004/0126785 |
| CA125/M17S2 | ovarian cancer | 2004/0126824 |
| IAI.3B | ovarian cancer | 2005/0031591 |
| CRG-L2 | liver cancer | 2005/0124068 |
| TRPM4 | prostate cancer | 2006/0188990 |
| RTVP | glioma | 2006/0216731 |
| TARP | prostate cancer, breast cancer | 2007/0032439 |
| telomere reverse transcriptase | cancer | 2007/0059287 |
| A4 amyloid protein | Alzheimer's disease | 5,151,508 |
| amyloid β-protein precursor | Alzheimer's disease | 5,643,726 |
| precursor of the Alzheimer's Disease A4 amyloid protein | Alzheimer's disease | 5,853,985 |
| neuropeptide FF | CNS disorders | 6,320,038 |
| endoplasmic reticulum stress elements | stress | 7,049,132 |
| urocortin II | psychopathologies | 7,087,385 |
| tyrosine hydroxylase | neurological disorders | 7,195,910 |
| complement factor 3; serum amyloid A3 | inflammation | 5,851,822 |
| tissue inhibitor of metalloproteinase-3 (TIMP-3) | rheumatism, cancer, autoimmune disease, inflammation | 5,854,019 |
| p75 tumor necrosis factor receptor | autoimmune disease | 5,959,094 |
| tumor necrosis factor-α | inflammation | 6,537,784 |
| peroxisome proliferator activated receptor/IIA-1 nonpancreatic secreted phospholipase A2 | inflammation | 6,870,044 |
| SOCS-3 | growth disorders, autoimmune disease, inflammation | 2002/0174448 |
| SR-BI | lipid disorders | 5,965,790 |
| Ob | obesity | 5,698,389 |
| site-1 protease | obesity, diabetes | 7,045,294 |
| TIGR | glaucoma | 7,138,511 |
| VL30 | anoxia | 5,681,706 |
| excitatory amino acid transporter-2 | nervous system ischemia | 2004/0171108 |
| MDTS9 | renal failure | 2006/0014931 |
| LIM, pyrroline 5-carboxylate reductase, SIM2 | prostate disorders | 2006/0134688 |
| Bax | apoptosis | 5,744,310 |
| fas | apoptosis | 5,888,764 |
| bbc3 | apoptosis | 7,202,024 |
| PINK-1 | PI-3 kinase/Akt pathway disorders | 2006/0228776 |

TABLE 2

| Promoter Sequence | Tissue Specificity | Patent/Published Application No. |
|---|---|---|
| troponin T | skeletal muscle | 5,266,488 |
| myoD | muscle | 5,352,595 |
| actin | muscle | 5,374,544 |
| smooth muscle 22α | arterial smooth muscle | 5,837,534 |
| utrophin | muscle | 5,972,609 |
| myostatin | muscle | 6,284,882 |
| smooth muscle myosin heavy chain | smooth muscle | 6,780,610 |
| cardiac ankyrin repeat protein | cardiac muscle | 7,193,075 |
| MLP | muscle | 2002/0042057 |
| smoothelin | smooth muscle | 2003/0157494 |
| MYBPC3 | cardiomyocytes | 2004/0175699 |
| Tα1 α-tubulin | neurons | 5,661,032 |
| intercellular adhesion molecule-4 (ICAM-4) | neurons | 5,753,502 |
| γ-aminobutyric acid type A receptor β1 subunit | hippocampus | 6,066,726 |
| neuronal nicotinic acetylcholine receptor β2-subunit | neurons | 6,177,242 |
| presenilin-1 | neurons | 6,255,473 |
| calcium-calmodulin-dependent kinase IIα | forebrain | 6,509,190 |
| $CRF_{2\alpha}$ receptor | brain | 7,071,323 |
| nerve growth factor | neurons | 2003/159159 |
| GLP-2 receptor | gut, brain | 2002/0045173 |
| type I transglutaminase | keratinocytes | 5,643,746 |
| K14 | keratinocytes | 6,596,515 |
| stearoyl-CoA desaturase | skin | 2002/0151018 |
| megsin | renal cells | 6,790,617 |
| prolactin | pituitary | 5,082,779 |
| GDF-9 | ovary, testes, hypothalamus, pituitary, placenta | 7,227,013 |
| PSP94 | prostate | 2003/0110522 |
| NRL; NGAL | mammary gland | 5,773,290 |
| long whey acidic protein | mammary gland | 5,831,141 |
| mammary associated amyloid A | mammary ductal epithelial cells | 2005/0107315 |
| endothelin-1 | endothelial cells | 5,288,846 |
| serglycin | hematopoietic cells | 5,340,739 |
| platelet-endothelial cell adhesion molecule-1 (PECAM-1) | platelets, leukocytes, endothelial cells | 5,668,012 |
| Tie receptor tyrosine kinase | endothelial cells, bone marrow | 5,877,020 |
| KDR/flk-1 | endothelial cells | 5,888,765 |
| endoglin | endothelial cells | 6,103,527 |
| CCR5 | myeloid and lymphoid cells | 6,383,746 |
| CD11d | myeloid cells | 6,881,834 |
| platelet glycoprotein IIb | hematopoietic cells | 6,884,616 |
| preproendothelin-1 | endothelial cells | 7,067,649 |
| interleukin-18 binding protein | mononuclear cells | 2006/0239984 |
| CD34 | hematopoietic stem cells | 5,556,954 |
| Tec tyrosine kinase | hematopoietic stem cells, liver | 6,225,459 |
| AC133 | stem cells | 2005/0125849 |

Other genes that exhibit changes in expression levels during specific diseases or disorders and therefore are useful in the present invention include, without limitation, the genes (along with the associated disease/disorder) listed in Table 3.

TABLE 3

| Gene | Disease/Disorder | Patent/Published Application No. |
|---|---|---|
| MLH1, MSH2, MSH6, PMS1, APC | Colorectal cancer | 7,148,016 |
| LEF-1 | Colon cancer | 2002/0169300 |
| $F_2$ receptor | Colon cancer | 2002/0187502 |
| TGF-β type II receptor | Colon cancer | 2004/0038284 |
| EYA4 | Colon cancer | 2005/0003463 |
| PCA3 | Prostate cancer | 7,138,235 |
| K2 | Prostate cancer | 6,303,361 |
| PROST 03 | Prostate cancer metastases | 2002/0009455 |
| PCAM-1 | Prostate cancer | 2002/0042062 |
| PCADM-1 | Prostate cancer | 2003/0100033 |

TABLE 3-continued

| Gene | Disease/Disorder | Patent/Published Application No. |
|---|---|---|
| PCA3$_{dd3}$ | Prostate cancer | 2003/0165850 |
| PCAV | Prostate cancer | 2006/0275747 |
| PAcP | Androgen-insensitive prostate cancer | 2006/0294615 |
| SEQ ID NO: 1 of the patent 5,866,329, incorporated by reference herein | Liver cancer | 5,866,329 |
| SEQ ID NOS: 1, 3 of the U.S. patent application publication 2002/0115094, incorporated by reference herein | Hepatocellular cancer | 2002/0115094 |
| SEQ ID NO: 1 of the patent U.S. application publication 2005/0037372, incorporated by reference herein | Hepatocellular carcinoma | 2005/0037372 |
| ATB$_0$ | Hepatocellular carcinoma | 2006/0280725 |
| SEQ ID NOS: 1, 3 of the U.S. patent application publication 2007/0042420, incorporated by reference herein | Liver cancer | 2007/0042420 |
| CSA-1 | Chondrosarcoma | 2001/0016649 |
| SEQ ID NOS: 1-15 of the U.S. patent application publication 2001/0016651, incorporated by reference herein | Pancreatic cancer | 2001/0016651 |
| SEQ ID NOS: 1-15 of the U.S. patent application publication 2003/0212264, incorporated by reference herein | Pancreatic cancer | 2003/0212264 |
| SYG972 | Breast cancer | 2002/0055107 |
| Urb-ctf | Breast cancer | 2003/0143546 |
| BCU399 | Breast cancer | 2003/0180728 |
| TBX2 | Breast cancer | 2004/0029185 |
| Cyr61 | Breast cancer | 2004/0086504 |
| DIAPH3 | Breast cancer | 2005/0054826 |
| SEQ ID NOS: 1-24 of the U.S. patent application publication 2007/0134669, incorporated by reference herein | Breast cancer | 2007/0134669 |
| Human aspartyl (asparaginyl) beta-hydroxylase | CNS cancer | 2002/0102263 |
| BEHAB | CNS cancer | 2003/0068661 |
| IL-8 | Kaposi's Sarcoma | 2003/0096781 |
| SEQ ID NOS: 1-278 of the U.S. patent application publication 2002/0198362, incorporated by reference herein | Hematological cancers | 2002/0198362 |
| BLSA | B-cell cancer | 2003/0147887 |
| BP1 | Leukemia | 2003/0171273 |
| DAP-kinase, HOXA9 | Non-small cell lung cancer | 2003/0224509 |
| ARP | Clear cell renal carcinoma, inflammatory disorders | 2004/0010119 |
| Nbk | Renal cancer | 2005/0053931 |
| CD43 | Ovarian cancer | 2006/0216231 |
| SEQ ID NOS: 1-84 of the U.S. patent application publication 2007/0054268, incorporated by reference herein | Ovarian cancer | 2007/0054268 |
| β7-hcG, β6-hCG, β6e-hCG, β5-hCG, β8-hcG, β3-hCG | Uterine tumors | 2006/0292567 |
| MTA1s | Hormone insensitive cancer | 2006/0204957 |
| Old-35, Old-64 | Tumor proliferation | 2003/0099660 |
| LAGE-1 | Cancer | 6,794,131 |
| CIF150/hTAF$_{II}$150 | Cancer | 6,174,679 |
| P65 oncofetal protein | Cancer | 5,773,215 |
| Telomerase | Cancer | 2002/0025518 |
| CYP1B1 | Cancer | 2002/0052013 |
| 14-3-3σ | Cancer | 2002/0102245 |
| NES1 | Cancer | 2002/0106367 |
| CAR-1 | Cancer | 2002/0119541 |
| HMGI, MAG | Cancer | 2002/0120120 |
| ELL2 | Cancer | 2002/0132329 |
| Ephrin B2 | Cancer | 2002/0136726 |
| WAF1 | Cancer | 2002/0142442 |
| CIF130 | Cancer | 2002/0143154 |
| C35 | Cancer | 2002/0155447 |

TABLE 3-continued

| Gene | Disease/Disorder | Patent/Published Application No. |
|---|---|---|
| BMP2 | Cancer | 2002/0159986 |
| BUB3 | Cancer | 2002/0160403 |
| Polymerase kappa | Cancer | 2003/0017573 |
| EAG1, EAG2 | Cancer | 2003/0040476 |
| SEQ ID NOS: 18, 20, 22 of the U.S. patent application publication 2003/0044813, incorporated by reference herein | Cancer | 2003/0044813 |
| HMG I | Cancer | 2003/0051260 |
| HLTF | Cancer | 2003/0082526 |
| Barx2 | Cancer | 2003/0087243 |
| SEQ ID NOS: 18, 20, 22, 32, 34, 36 of the U.S. patent application publication 2003/0108920, incorporated by reference herein | Cancer | 2003/0108920 |
| Cables | Cancer | 2003/0109443 |
| Pp 32r1 | Cancer | 2003/0129631 |
| BMP4 | Cancer | 2003/0134790 |
| TS10q23.3 | Cancer | 2003/0139324 |
| Nuclear spindle-associating protein | Cancer | 2003/0157072 |
| PFTAIRE | Cancer | 2003/0166217 |
| SEMA3B | Cancer | 2003/0166557 |
| MOGp | Cancer, multiple sclerosis, inflammatory disease | 2003/0166898 |
| Fortilin | Cancer | 2003/0172388 |
| SEQ ID NO: 1 of the U.S. patent application publication 2003/0215833, incorporated by reference herein | Cancer | 2003/0215833 |
| IGFBP-3 | Cancer | 2004/0005294 |
| Polyhomeotic 2 | Cancer | 2004/0006210 |
| PNQALRE | Cancer | 2004/0077009 |
| SEQ ID NOS: 1, 3 of the U.S. patent application publication 2004/0086916, incorporated by reference herein | Cancer | 2004/0086916 |
| SCN5A | Cancer | 2004/0146877 |
| miR15, miR16 | Cancer | 2004/0152112 |
| Headpin | Cancer | 2004/0180371 |
| PAOh1/SMO | Cancer | 2004/0229241 |
| Hippo, Mst2 | Cancer | 2005/0053592 |
| PSMA-like | Cancer, neurological disorders | 2005/0064504 |
| JAB1 | Cancer | 2005/0069918 |
| NF-AT | Cancer | 2005/0079496 |
| P28ING5 | Cancer | 2005/0097626 |
| MTG16 | Cancer | 2005/0107313 |
| ErbB-2 | Cancer | 2005/0123538 |
| HDAC9 | Cancer | 2005/0130146 |
| GPBP | Cancer | 2005/0130227 |
| MG20 | Cancer | 2005/0153352 |
| KLF6 | Cancer | 2005/0181374 |
| ARTS1 | Cancer | 2005/0266443 |
| Dock 3 | Cancer | 2006/0041111 |
| Annexin 8 | Cancer | 2006/0052320 |
| MH15 | Cancer | 2006/0068411 |
| DELTA-N p73 | Cancer | 2006/0088825 |
| RapR6 | Cancer | 2006/099676 |
| StarD10 | Cancer | 2006/0148032 |
| Ciz1 | Cancer | 2006/0155113 |
| HLJ1 | Cancer | 2006/0194235 |
| RapR7 | Cancer | 2006/0240021 |
| A34 | Cancer | 2006/0292154 |
| Sef | Cancer | 2006/0293240 |
| Killin | Cancer | 2007/0072218 |
| SGA-1M | Cancer | 2007/0128593 |
| TGFβ Type II receptor | Cancer | 2002/0064786 |
| GCA-associated genes | Giant cell arteritis | 6,743,903 |
| PRV-1 | Polycythemia vera | 6,686,153 |
| SEQ ID NOS: 2, 4 of the U.S. Pat. No. 5,948,637, incorporated by reference herein | Ischemia | 5,948,637 |
| Vezf1 | Vascular disorders | 2002/0023277 |
| MLP | Dilatative cardiomyopathy | 2002/0042057 |
| VEGI | Pathological angiogenesis | 2002/0111325 |
| PRO256 | Cardiovascular disorders | 2002/0123091 |
| AOP2 | Atherosclerosis | 2002/0142417 |

TABLE 3-continued

| Gene | Disease/Disorder | Patent/Published Application No. |
| --- | --- | --- |
| Remodelin | Arterial restenosis, fibrosis | 2002/0161211 |
| Phosphodiesterase 4D | Stroke | 2003/0054531 |
| Prostaglandin receptor subtype EP3 | Peripheral arterial occlusive disease | 2003/0157599 |
| CARP | Heart disorders | 2004/0014706 |
| HOP | Congenital heart disease | 2004/0029158 |
| SEQ ID NOS: 1-4 of the U.S. patent application publication 2004/0087784, incorporated by reference herein | Apoplexy | 2004/0087784 |
| PLTP | Atherosclerosis, vascular disease, hypercholesterolemia, Tangier's disease, familial HDL deficiency disease | 2006/0252787 |
| SEQ ID NOS: 1, 3-8, 15, 16 of the U.S. patent application publication 2007/0160996, incorporated by reference herein | Thrombosis | 2007/0160996 |
| UCP-2 | Stroke | 2002/0172958 |
| FLJ11011 | Fanconi's Anemia | 2006/0070134 |
| Codanin-1 | Anemia | 2006/0154331 |
| SEQ ID NOS: 1, 6, 8 of the U.S. Pat. No. 5,763,591, incorporated by reference herein | Insulin-dependent diabetes mellitus | 5,763,591 |
| Resistin | Type II diabetes | 2002/0161210 |
| Archipelin | Diabetes | 2003/0202976 |
| SEQ ID NOS: 2, 7, 16, 27 of the U.S. patent application publication 2004/0053397, incorporated by reference herein | Diabetes, hyperlipidemia | 2004/0053397 |
| Neuronatin | Metabolic disorders | 2004/0259777 |
| Ncb5or | Diabetes | 2005/0031605 |
| 7B2 | Endocrine disorders | 2005/0086709 |
| PTHrP, PEX | Metabolic bone diseases | 2005/0113303 |
| KChIP1 | Type II diabetes | 2005/0196784 |
| SLIT-3 | Type II diabetes | 2006/0141462 |
| CX3CR1 | Type II diabetes | 2006/0160076 |
| SMAP-2 | Diabetes | 2006/0210974 |
| SEQ ID NOS: 2, 8, 12, 16, 22, 26, 28, 32 of the U.S. patent application publication 2006/0228706, incorporated by reference herein | Type II diabetes | 2006/0228706 |
| IC-RFX | Diabetes | 2006/0264611 |
| E2IG4 | Diabetes, insulin resistance, obesity | 2007/0036787 |
| SEQ ID NOS: 2, 8, 10, 14, 18, 24, 26, 30, 34, 38, 44, 50, 54, 60, 62, 68, 74, 80, 86, 92, 98, 104, 110 of the U.S. patent application publication 2007/0122802, incorporated by reference herein | Diabetes | 2007/0122802 |
| UCP2 | Body weight disorders | 2002/0127600 |
| Ob receptor | Body weight disorders | 2002/0182676 |
| Ob | Bodyweight disorders | 2004/0214214 |
| Dp1 | Neurodegenerative disorders | 2001/0021771 |
| NRG-1 | Schizophrenia | 2002/0045577 |
| Synapsin III | Schizophrenia | 2002/0064811 |
| NRG1AG1 | Schizophrenia | 2002/0094954 |
| AL-2 | Neuronal disorders | 2002/0142444 |
| Proline dehydrogenase | Bipolar disorder, major depressive disorder, schizophrenia, obsessive compulsive disorder | 2002/0193581 |
| MNR2 | Chronic neurodegenerative disease | 2002/0197678 |
| ATM | Ataxia-telangiectasia | 2004/0029198 |
| Ho-1 | Dementing diseases | 2004/0033563 |
| CON202 | Schizophrenia | 2004/0091928 |
| Ataxin-1 | Neurodegenerative disorders | 2004/0177388 |
| NR3B | Motor neuron disorders | 2005/0153287 |
| NIPA-1 | Hereditary spastic paraplegia | 2005/0164228 |

TABLE 3-continued

| Gene | Disease/Disorder | Patent/Published Application No. |
|---|---|---|
| DEPP, adrenomedullin, csdA | Schizophrenia | 2005/0227233 |
| Inf-20 | Neurodegenerative diseases | 2006/0079675 |
| EOPA | Brain development and degeneration disorders | 2007/0031830 |
| SERT | Autism | 2007/0037194 |
| FRP-1 | Glaucoma | 2002/0049177 |
| Serum amyloid A | Glaucoma | 2005/0153927 |
| BMP2 | Osteoporosis | 2002/0072066 |
| BMPR1A | Juvenile polyposis | 2003/0072758 |
| ACLP | Gastroschisis | 2003/0084464 |
| Resistin-like molecule β | Familial adenomatous polyposis, diabetes, insulin resistance, colon cancer, inflammatory bowel disorder | 2003/0138826 |
| Dlg5 | Inflammatory bowel disease | 2006/0100132 |
| SEQ ID NOS: 1-82 of the U.S. patent application publication 2002/0119452, incorporated by reference herein | Osteoarthritis | 2002/0119452 |
| TRANCE | Immune system disorders | 2003/0185820 |
| Matrilin-3 | Osteoarthritis | 2003/0203380 |
| Synoviolin | Rheumatoid arthritis | 2004/0152871 |
| SEQ ID NOS: 9, 35 of the U.S. patent application publication 2007/0028314, incorporated by reference herein | Osteoarthritis | 2007/0028314 |
| HIV LTR | HIV infection | 5,627,023 |
| SHIVA | HIV infection | 2004/0197770 |
| EBI 1, EBI 2, EBI 3 | Epstein Barr virus infection | 2002/0040133 |
| NM23 family | Skin/intestinal disorders | 2002/0034741 |
| SEQ ID NO: 1 of the U.S. patent application publication 2002/0169127, incorporated by reference herein | Psoriasis | 2002/0169127 |
| Eps8 | Skin disorders, wound healing | 2003/0180302 |
| Beta-10 | Thyroid gland pathology | 2002/0015981 |
| SEQ ID NO: 2 of the U.S. patent application publication 2003/0207403, incorporated by reference herein | Thyroid conditions | 2003/0207403 |
| SEQ ID NO: 3 of the U.S. patent application publication 2007/0020275, incorporated by reference herein | Thyroid disorders | 2007/0020275 |
| Hair follicle growth factor | Alopecia | 2003/0036174 |
| Corneodesmosin | Alopecia | 2003/0211065 |
| GCR9 | Asthma, lymphoma, leukemia | 2003/0166150 |
| SEQ ID NO: 1-71 of the U.S. patent application publication 2004/0002084, incorporated by reference herein | Asthma | 2004/0002084 |
| Bg | Chediak-Higashi syndrome | 2002/0115144 |
| SEQ ID NOS: 1-16 of the U.S. patent application publication 2002/0127555, incorporated by reference herein | Endometriosis | 2002/0127555 |
| FGF23 | Hypophosphatemic disorders | 2005/0156014 |
| BBSR | Bardet-Biedl syndrome | 2003/0152963 |
| MIC-1 | Fetal abnormalities, cancer, inflammatory disorders, miscarriage, premature birth | 2004/0053325 |
| MIA-2 | Liver damage | 2004/0076965 |
| IL-17B | Cartilage degenerative disorders | 2004/0171109 |
| Formylglycine generating enzyme | Multiple sulfatase deficiency | 2004/0229250 |
| LPLA2 | Pulmonary alveolar proteinosis | 2006/0008455 |

TABLE 3-continued

| Gene | Disease/Disorder | Patent/Published Application No. |
| --- | --- | --- |
| CXCL1O | Respiratory illnesses | 2006/0040329 |
| SEQ ID NOS: 1, 2 of the U.S. patent application publication 2006/0140945, incorporated by reference herein | Nephropathy | 2006/0140945 |
| HFE2A | Iron metabolism disease | 2007/0166711 |

Once a gene with an expression pattern that is modulated during a disease or disorder is identified, the promoter of the gene may be used in the gene switch of the invention. The sequence of many genes, including the promoter region, is known in the art and available in public databases, e.g., Gen-Bank. Thus, once an appropriate gene is identified, the promoter sequence can be readily identified and obtained. Another aspect of the present invention is directed towards identifying suitable genes whose promoter can be isolated and placed into a gene switch. The identity of the gene, therefore, may not be critical to specific embodiments of the present invention, provided the promoter can be isolated and used in subsequent settings or environments. The current invention thus includes the use of promoters from genes that are yet to be identified. Once suitable genes are identified, it can be a matter of routine skill or experimentation to determine the genetic sequences needed for promoter function. Indeed, several commercial protocols exist to aid in the determination of the promoter region of genes of interest. By way of example, Ding et al. recently elucidated the promoter sequence of the novel Sprouty4 gene (*Am. J. Physiol. Lung Cell. Mol. Physiol.* 287: L52 (2004), which is incorporated by reference) by progressively deleting the 5'-flanking sequence of the human Sprouty4 gene. Briefly, once the transcription initiation site was determined, PCR fragments were generated using common PCR primers to clone segments of the 5'-flanking segment in a unidirectional manner. The generated segments were cloned into a luciferase reporter vector and luciferase activity was measured to determine the promoter region of the human Sprouty4 gene.

Another example of a protocol for acquiring and validating gene promoters includes the following steps: (1) acquire diseased and non-diseased cell/tissue samples of similar/same tissue type; (2) isolate total RNA or mRNA from the samples; (3) perform differential microarray analysis of diseased and non-diseased RNA; (4) identify candidate disease-specific transcripts; (5) identify genomic sequences associated with the disease-specific transcripts; (6) acquire or synthesize DNA sequence upstream and downstream of the predicted transcription start site of the disease-specific transcript; (7) design and produce promoter reporter vectors using different lengths of DNA from step 6; and (8) test promoter reporter vectors in diseased and non-diseased cells/tissues, as well as in unrelated cells/tissues.

The source of the promoter that is inserted into the gene switch can be natural or synthetic, and the source of the promoter should not limit the scope of the invention described herein. In other words, the promoter may be directly cloned from cells, or the promoter may have been previously cloned from a different source, or the promoter may have been synthesized.

The gene switch may be any gene switch that regulates gene expression by addition or removal of a specific ligand. In one embodiment, the gene switch is one in which the level of gene expression is dependent on the level of ligand that is present. Examples of ligand-dependent transcription factors that may be used in the gene switches of the invention include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and International Published Application No. WO 01/70816. Examples of chimeric ecdysone receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617, each of which is incorporated by reference in its entirety. An example of a non-steroidal ecdysone agonist-regulated system is the RheoSwitch® Mammalian Inducible Expression System (New England Biolabs, Ipswich, Mass.).

In one embodiment, the gene switch comprises a single transcription factor sequence encoding a ligand-dependent transcription factor under the control of a diagnostic switch promoter. The transcription factor sequence may encode a ligand-dependent transcription factor that is a naturally occurring or an artificial transcription factor. An artificial transcription factor is one in which the natural sequence of the transcription factor has been altered, e.g., by mutation of the sequence or by the combining of domains from different transcription factors. In one embodiment, the transcription factor comprises a Group H nuclear receptor LBD. In one embodiment, the Group H nuclear receptor LBD is from an EcR, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, or a farnesol receptor. In another embodiment, the Group H nuclear receptor LBD is from an ecdysone receptor.

The EcR and the other Group H nuclear receptors are members of the nuclear receptor superfamily wherein all members are generally characterized by the presence of an amino-terminal transactivation domain (TD), a DNA binding domain (DBD), and a LBD separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, *Science* 240:889 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for response elements. These domains may be either native, modified, or chimeras of different domains of heterologous receptor proteins. The EcR, like a subset of the nuclear receptor family, also possesses less well-defined regions responsible for heterodimerization properties. Because the domains of nuclear receptors are modular in nature, the LBD, DBD, and TD may be interchanged.

In another embodiment, the transcription factor comprises a TD, a DBD that recognizes a response element associated with the reporter gene whose expression is to be modulated; and a Group H nuclear receptor LBD. In certain embodiments, the Group H nuclear receptor LBD comprises a substitution mutation.

Figure 3:
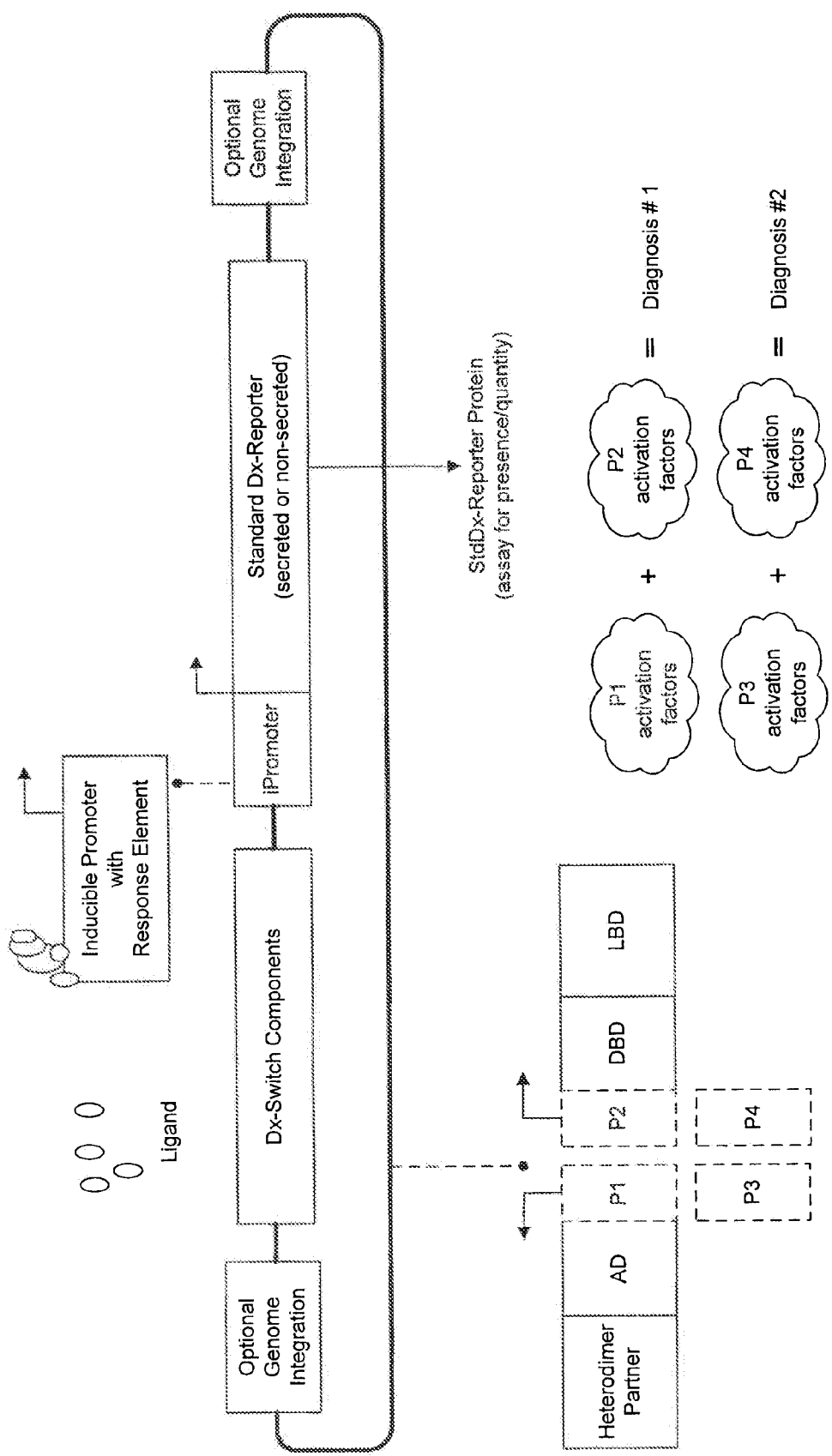

In another embodiment, the gene switch comprises a first transcription factor sequence under the control of a first diagnostic switch promoter and a second transcription factor sequence under the control of a second diagnostic switch promoter, wherein the proteins encoded by said first transcription factor sequence and said second transcription factor sequence interact to form a protein complex which functions as a ligand-dependent transcription factor, i.e., a "dual switch"- or "two-hybrid"-based gene switch. The first and second diagnostic switch promoters may be the same or different. In this embodiment, the presence of two different diagnostic switch promoters in the gene switch that are required for reporter gene expression enhances the specificity of the diagnostic method (see FIG. 3). FIG. 3 also demonstrates the ability to modify the diagnostic gene switch to detect any disease or disorder simply by inserting the appropriate diagnostic switch promoters.

Figure 1:
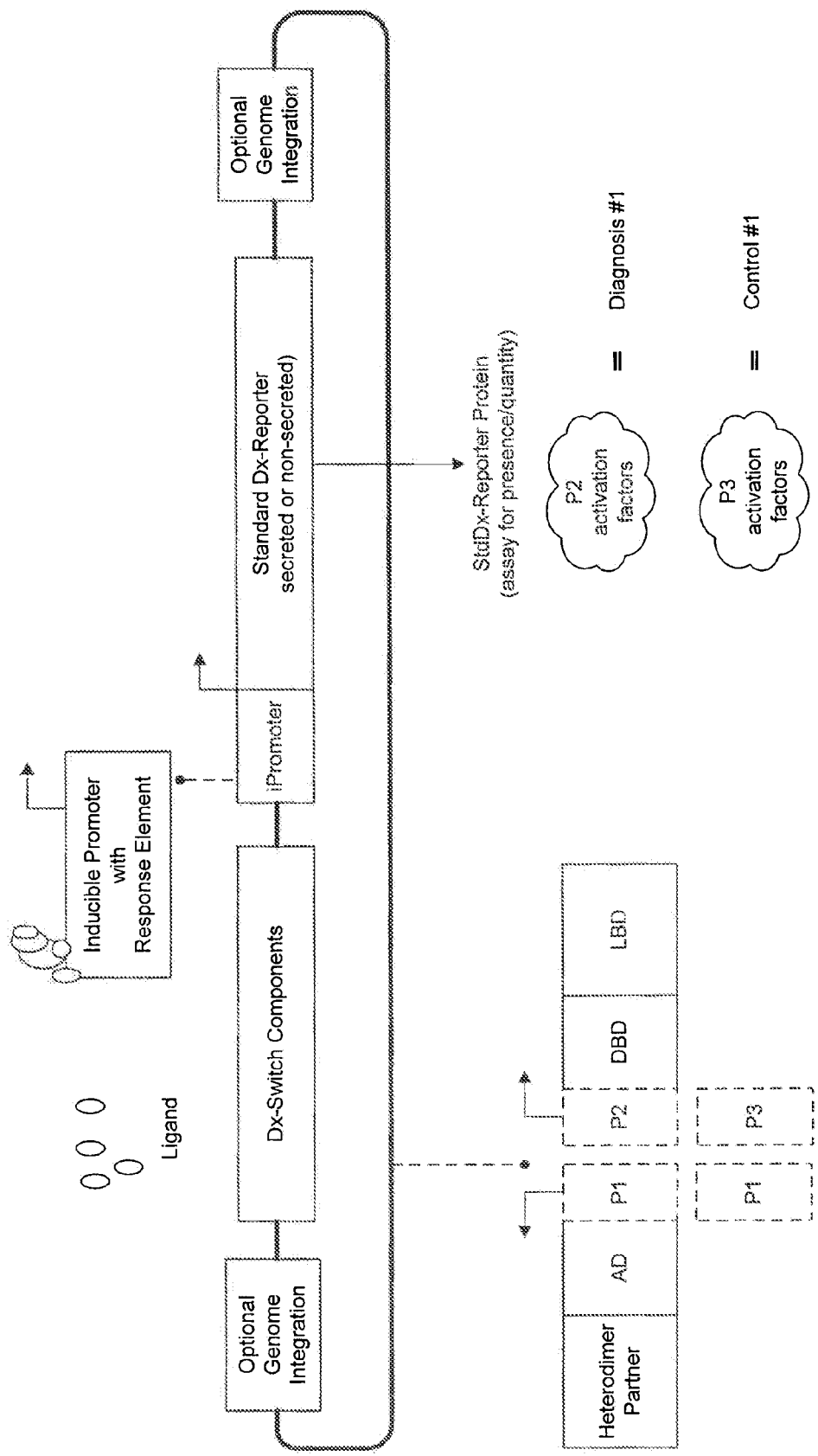

In a further embodiment, the first transcription factor sequence is under the control of a diagnostic switch promoter (e.g., P2 or P3 in FIG. 1) and the second transcription factor sequence is under the control of a constitutive promoter (e.g., P1 in FIG. 1). In this embodiment, one portion of the ligand-dependent transcription factor will be constitutively present while the second portion will only be synthesized if the subject has the disease or disorder.

Figure 2:
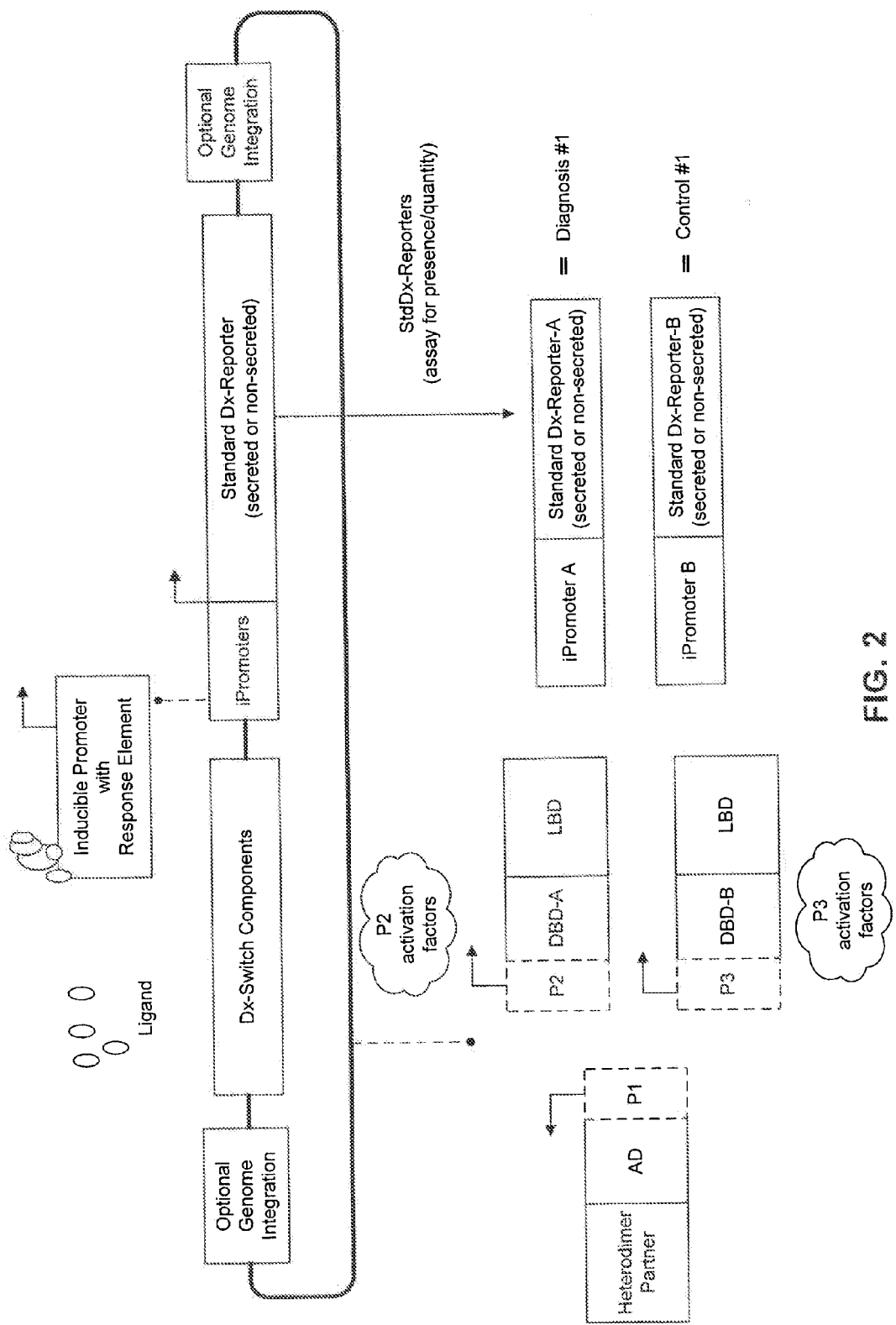

In another embodiment, the first transcription factor sequence is under the control of a first diagnostic switch promoter (e.g., P1 in FIG. 2) and two or more different second transcription factor sequences are under the control of different diagnostic switch promoters (e.g., P2 and P3 in FIG. 2). In this embodiment, each of the second transcription factor sequences may have a different DBD that recognizes a different inducible promoter sequence (e.g., DBD-A binds to inducible promoter A and DBD-B binds to inducible promoter B). Each of the inducible promoters may be operably linked to a different reporter gene that produces a unique signal. In this manner, multiple diagnoses may be made simultaneously or a differential diagnosis between two or more possible diseases may be made.

In one embodiment, the first transcription factor sequence encodes a polypeptide comprising a TD, a DBD that recognizes a response element associated with the reporter gene whose expression is to be modulated; and a Group H nuclear receptor LBD, and the second transcription factor sequence encodes a transcription factor comprising a nuclear receptor LBD selected from the group consisting of a vertebrate RXR LBD, an invertebrate RXR LBD, an ultraspiracle protein LBD, and a chimeric LBD comprising two polypeptide fragments, wherein the first polypeptide fragment is from a vertebrate RXR LBD, an invertebrate RXR LBD, or an ultraspiracle protein LBD, and the second polypeptide fragment is from a different vertebrate RXR LBD, invertebrate RXR LBD, or ultraspiracle protein LBD.

In another embodiment, the gene switch comprises a first transcription factor sequence encoding a first polypeptide comprising a nuclear receptor LBD and a DBD that recognizes a response element associated with the reporter gene whose expression is to be modulated, and a second transcription factor sequence encoding a second polypeptide comprising a TD and a nuclear receptor LBD, wherein one of the nuclear receptor LBDs is a Group H nuclear receptor LBD. In a preferred embodiment, the first polypeptide is substantially free of a TD and the second polypeptide is substantially free of a DBD. For purposes of the invention, "substantially free" means that the protein in question does not contain a sufficient sequence of the domain in question to provide activation or binding activity.

In another aspect of the invention, the first transcription factor sequence encodes a protein comprising a heterodimer partner and a TD and the second transcription factor sequence encodes a protein comprising a DBD and a LBD.

When only one nuclear receptor LBD is a Group H LBD, the other nuclear receptor LBD may be from any other nuclear receptor that forms a dimer with the Group H LBD. For example, when the Group H nuclear receptor LBD is an EcR LBD, the other nuclear receptor LBD "partner" may be from an EcR, a vertebrate RXR, an invertebrate RXR, an ultraspiracle protein (USP), or a chimeric nuclear receptor comprising at least two different nuclear receptor LBD polypeptide fragments selected from the group consisting of a vertebrate RXR, an invertebrate RXR, and a USP (see WO 01/70816 A2, International Patent Application No. PCT/US02/05235 and US 2004/0096942 A1, incorporated herein by reference in their entirety). The "partner" nuclear receptor ligand binding domain may further comprise a truncation mutation, a deletion mutation, a substitution mutation, or another modification.

In one embodiment, the vertebrate RXR LBD is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

In one embodiment, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), an ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

In one embodiment, the chimeric RXR LBD comprises at least two polypeptide fragments selected from the group consisting of a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment.

In one embodiment, the chimeric RXR ligand binding domain comprises at least one vertebrate species RXR polypeptide fragment and one invertebrate species RXR polypeptide fragment.

In another embodiment, the chimeric RXR ligand binding domain comprises at least one vertebrate species RXR polypeptide fragment and one non-Dipteran/non-Lepidopteran invertebrate species RXR homolog polypeptide fragment.

The ligand, when combined with the LBD of the nuclear receptor(s), which in turn are bound to the response element linked to the reporter gene, provides external temporal regulation of expression of the reporter gene. The binding mechanism or the order in which the various components of this invention bind to each other, that is, for example, ligand to LBD, DBD to response element, TD to promoter, etc., is not critical.

In a specific example, binding of the ligand to the LBD of a Group H nuclear receptor and its nuclear receptor LBD partner enables expression of the reporter gene. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and TD, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988)) or LexA protein from *Escherichia coli* (see Brent et al., *Cell* 43:729 (1985)), or synthetic response elements specific for targeted interactions with proteins designed, modified, and selected for such specific interactions (see, for example, Kim et al., *Proc. Natl. Acad. Sci. USA,* 94:3616 (1997)) to accommodate hybrid receptors.

The functional EcR complex may also include additional protein(s) such as immunophilins. Additional members of the nuclear receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC -1/NCoA-1, TIF2/GRIP/NCoA-2, ACTR/AIB1/RAC3/pCIP as well as the promiscuous coactivator C response element B binding protein, CBP/p300 (for review see Glass et al., *Curr. Opin. Cell Biol.* 9:222 (1997)). Also, protein cofactors generally known as corepressors (also known as repressors, silencers, or silencing mediators) may be required to effectively inhibit transcriptional activation in the absence of ligand. These corepressors may interact with the unliganded EcR to silence the activity at the response element. Current evidence suggests that the binding of ligand changes the conformation of the receptor, which results in release of the corepressor and recruitment of the above described coactivators, thereby abolishing their silencing activity. Examples of corepressors include N-CoR and SMRT (for review, see Horwitz et al., *Mol Endocrinol.* 10:1167 (1996)). These cofactors may either be endogenous within the cell or organism, or may be added exogenously as transgenes to be expressed in either a regulated or unregulated fashion.

The reporter gene may be any gene that encodes a detectable protein. The protein may be secreted or non-secreted. In one embodiment, the protein is one that can be assayed using various standard assay methods, e.g., immunoassays (such as those immunofluorescent antibodies), colorimetric assays, fluorescent assays, or luminescent assays. Examples of suitable reporter genes include, without limitation, luciferase, green fluorescent protein, β-galactosidase, β-glucuronidase, thymidine kinase, and chloramphenicol acetyltransferase.

The reporter gene is operably linked to a promoter comprising at least one response element that is recognized by the DBD of the ligand-dependent transcription factor encoded by the gene switch. In one embodiment, the promoter comprises 1, 2, 3, 4, 5, 6, 7, 8, 9, 10, or more copies of the response element. Promoters comprising the desired response elements may be naturally occurring promoters or artificial promoters created using techniques that are well known in the art, e.g., one or more response elements operably linked to a minimal promoter.

To introduce the polynucleotides into the cells, a vector can be used. The vector may be, for example, a plasmid vector or a single- or double-stranded RNA or DNA viral vector. Such vectors may be introduced into cells by well-known techniques for introducing DNA and RNA into cells. Viral vectors may be replication competent or replication defective. In the latter case, viral propagation generally will occur only in complementing host cells. As used herein, the term "host cell" or "host" is used to mean a cell of the present invention that is harboring one or more polynucleotides of the invention.

Thus, at a minimum, the vectors must include the polynucleotides of the invention. Other components of the vector may include, but are not limited to, selectable markers, chromatin modification domains, additional promoters driving expression of other polypeptides that may also be present on the vector (e.g., a lethal polypeptide), genomic integration sites, recombination sites, and molecular insertion pivots. The vectors may comprise any number of these additional elements, either within or not within the polynucleotides, such that the vector can be tailored to the specific goals of the diagnostic methods desired.

In one embodiment of the present invention, the vectors that are introduced into the cells further comprise a "selectable marker gene" which, when expressed, indicates that the diagnostic gene switch construct of the present invention has been integrated into the genome of the host cell. In this manner, the selector gene can be a positive marker for the genome integration. While not critical to the methods of the present invention, the presence of a selectable marker gene allows the practitioner to select for a population of live cells where the vector construct has been integrated into the genome of the cells. Thus, certain embodiments of the present invention comprise selecting cells where the vector has successfully been integrated. As used herein, the term "select" or variations thereof, when used in conjunction with cells, is intended to mean standard, well-known methods for choosing cells with a specific genetic make-up or phenotype. Typical methods include, but are not limited to, culturing cells in the presence of antibiotics, such as G418, neomycin and ampicillin. Other examples of selectable marker genes include, but are not limited to, genes that confer resistance to dihydrofolate reductase, hygromycin, or mycophenolic acid. Other methods of selection include, but are not limited to, a selectable marker gene that allows for the use of thymidine kinase, hypoxanthine-guanine phosphoribosyltransferase or adenine phosphoribosyltransferase as selection agents. Cells comprising a vector construct comprising an antibiotic resistance gene or genes would then be capable of tolerating the antibiotic in culture. Likewise, cells not comprising a vector construct comprising an antibiotic resistance gene or genes would not be capable of tolerating the antibiotic in culture.

As used herein, a "chromatin modification domain" (CMD) refers to nucleotide sequences that interact with a variety of proteins associated with maintaining and/or altering chromatin structure, such as, but not limited to, DNA insulators. See Ciavatta et al., *Proc. Nat'l Acad Sci. U.S.A.*, 103:9958 (2006), which is incorporated by reference herein. Examples of CMDs include, but are not limited to, the chicken β-globulin insulator and the chicken hypersensitive site 4 (cHS4). The use of different CMD sequences between one or more gene programs (i.e., a promoter, coding sequence, and 3' regulatory region), for example, can facilitate the use of the differential CMD DNA sequences as "mini homology arms" in combination with various microorganism or in vitro recombineering technologies to "swap" gene programs between existing multigenic and monogenic shuttle vectors. Other examples of chromatin modification domains are known in the art or can be readily identified.

Particular vectors for use with the present invention are expression vectors that code for proteins or portions thereof. Generally, such vectors comprise cis-acting control regions effective for expression in a host operatively linked to the polynucleotide to be expressed. Appropriate trans-acting factors are supplied by the host, supplied by a complementing vector or supplied by the vector itself upon introduction into the host.

A great variety of expression vectors can be used to express proteins. Such vectors include chromosomal, episomal and virus-derived vectors, e.g., vectors derived from bacterial plasmids, from bacteriophage, from yeast episomes, from yeast chromosomal elements, from viruses such as adeno-associated viruses, lentiviruses, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the present invention. Generally, any vector suitable to maintain, propagate or express polynucleotides or proteins in a host may be used for expression in this regard.

The DNA sequence in the expression vector is operatively linked to appropriate expression control sequence(s) including, for instance, a promoter to direct mRNA transcription. Representatives of additional promoters include, but are not limited to, constitutive promoters and tissue specific or inducible promoters. Examples of constitutive eukaryotic promoters include, but are not limited to, the promoter of the mouse metallothionein I gene (Hamer et al., *J. Mol. Appl. Gen.* 1:273 (1982)); the TK promoter of Herpes virus (McKnight, *Cell* 31:355 (1982)); the SV40 early promoter (Benoist et al., *Nature* 290:304 (1981)); and the vaccinia virus promoter. All of the above listed references are incorporated by reference herein. Additional examples of the promoters that could be used to drive expression of a protein include, but are not limited to, tissue-specific promoters and other endogenous promoters for specific proteins, such as the albumin promoter (hepatocytes), a proinsulin promoter (pancreatic beta cells) and the like. In general, expression constructs will contain sites for transcription, initiation and termination and, in the transcribed region, a ribosome binding site for translation. The coding portion of the mature transcripts expressed by the constructs may include a translation initiating AUG at the beginning and a termination codon (UAA, UGA or UAG) appropriately positioned at the end of the polypeptide to be translated.

In addition, the constructs may contain control regions that regulate, as well as engender expression. Generally, such regions will operate by controlling transcription, such as repressor binding sites and enhancers, among others.

Examples of eukaryotic vectors include, but are not limited to, pW-LNEO, pSV2CAT, pOG44, pXT1 and pSG available from Stratagene; pSVK3, pBPV, pMSG and pSVL available from Amersham Pharmacia Biotech; and pCMVDsRed2-express, pIRES2-DsRed2, pDsRed2-Mito, pCMV-EGFP available from Clontech. Many other vectors are well-known and commercially available.

Particularly useful vectors, which comprise molecular insertion pivots for rapid insertion and removal of elements of gene programs, are described in United States Published Patent Application No. 2004/0185556, U.S. patent application Ser. No. 11/233,246 and International Published Application Nos. WO 2005/040336 and WO 2005/116231, all of which are incorporated by reference. An example of such vectors is the UltraVector™ Production System (Intrexon Corp., Blacksburg, Va.), as described in WO 2007/038276, incorporated herein by reference. As used herein, a "gene program" is a combination of genetic elements comprising a promoter (P), an expression sequence (E) and a 3' regulatory sequence (3), such that "PE3" is a gene program. The elements within the gene program can be easily swapped between molecular pivots that flank each of the elements of the gene program. A molecular pivot, as used herein, is defined as a polynucleotide comprising at least two non-variable rare or uncommon restriction sites arranged in a linear fashion. In one embodiment, the molecular pivot comprises at least three non-variable rare or uncommon restriction sites arranged in a linear fashion. Typically any one molecular pivot would not include a rare or uncommon restriction site of any other molecular pivot within the same gene program. Cognate sequences of greater than 6 nucleotides upon which a given restriction enzyme acts are referred to as "rare" restriction sites. There are, however, restriction sites of 6 bp that occur more infrequently than would be statistically predicted, and these sites and the endonucleases that cleave them are referred to as "uncommon" restriction sites. Examples of either rare or uncommon restriction enzymes include, but are not limited to, AsiS I, Pac I, Sbf I, Fse I, Asc I, Mlu I, SnaB I, Not I, Sal I, Swa I, Rsr II, BSiW I, Sfo I, Sgr AI, AflIII, Pvu I, Ngo MIV, Ase I, Flp I, Pme I, Sda I, Sgf I, Srf I, and Sse8781 I.

The vector may also comprise restriction sites for a second class of restriction enzymes called homing endonuclease (HE) enzymes. HE enzymes have large, asymmetric restriction sites (12-40 base pairs), and their restriction sites are infrequent in nature. For example, the HE known as I-Scel has an 18 bp restriction site (5'TAGGGATAACAGGGTAAT3' (SEQ ID NO:4)), predicted to occur only once in every $7 \times 10^{10}$ base pairs of random sequence. This rate of occurrence is equivalent to only one site in a genome that is 20 times the size of a mammalian genome. The rare nature of HE sites greatly increases the likelihood that a genetic engineer can cut a gene program without disrupting the integrity of the gene program if HE sites were included in appropriate locations in a cloning vector plasmid.

Selection of appropriate vectors and promoters for expression in a host cell is a well-known procedure, and the requisite techniques for vector construction and introduction into the host, as well as its expression in the host are routine skills in the art.

The introduction of the polynucleotides into the cells can be a transient transfection, stable transfection, or can be a locus-specific insertion of the vector. Transient and stable transfection of the vectors into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis el al., Basic Methods in Molecular Biology (1986); Keown et al., 1990, Methods Enzymol. 185: 527-37; Sambrook et al., 2001, Molecular Cloning, A Laboratory Manual, Third Edition, Cold Spring Harbor Laboratory Press, N.Y., which are hereby incorporated by reference. These stable transfection methods result in random insertion of the vector into the genome of the cell. Further, the copy number and orientation of the vectors are also, generally speaking, random.

In one embodiment of the invention, the vector is inserted into a bio-neutral site in the genome. A bio-neutral site is a site in the genome where insertion of the polynucleotides interferes very little, if any, with the normal function of the cell. Bio-neutral sites may be analyzed using available bioinformatics. Many bio-neutral sites are known in the art, e.g., the ROSA-equivalent locus. Other bio-neutral sites may be identified using routine techniques well known in the art. Characterization of the genomic insertion site(s) is performed using methods known in the art. To control the location, copy number and/or orientation of the polynucleotides when introducing the vector into the cells, methods of locus-specific insertion may be used. Methods of locus-specific insertion are well-known in the art and include, but are not limited to, homologous recombination and recombinase-mediated genome insertion. Of course, if locus-specific insertion methods are to be used in the methods of the present invention, the vectors may comprise elements that aid in this locus-specific insertion, such as, but not limited to, homologous recombination. For example, the vectors may comprise one, two, three, four or more genomic integration sites (GISs). As used herein, a "genomic integration site" is defined as a portion of the vector sequence which nucleotide sequence is identical or nearly identical to portions of the genome within the cells that allows for insertion of the vector in the genome. In particular, the vector may comprise two genomic integration sites that flank at least the polynucleotides. Of course, the GISs may flank additional elements, or even all elements present on the vector.

In another embodiment, locus-specific insertion may be carried out by recombinase-site specific gene insertion. Briefly, bacterial recombinase enzymes, such as, but not limited to, PhiC31 integrase can act on "pseudo" recombination sites within the human genome. These pseudo recombination sites can be targets for locus-specific insertion using the recombinases. Recombinase-site specific gene insertion is described in Thyagarajan et al., *Mol. Cell Biol.* 21:3926 (2001), which is hereby incorporated by reference. Other examples of recombinases and their respective sites that may be used for recombinase-site specific gene insertion include, but are not limited to, serine recombinases such as R4 and TP901-1 and recombinases described in WO 2006/083253, incorporated herein by reference.

In a further embodiment, the vector may comprise a chemo-resistance gene, e.g., the multidrug resistance gene mdr1, dihydrofolate reductase, or $O^6$-alkylguanine-DNA alkyltransferase. The chemo-resistance gene may be under the control of a constitutive (e.g., CMV) or inducible (e.g., RheoSwitch®) promoter. In this embodiment, if it is desired to treat a disease diagnosed in a subject while maintaining the modified cells within the subject, a clinician may apply a chemotherapeutic agent to destroy diseased cells while the modified cells would be protected from the agent due to expression of a suitable chemo-resistance gene and may continue to be used for monitoring of the progression of the disease or effectiveness of the treatment. By placing the chemo-resistance gene under an inducible promoter, the unnecessary expression of the chemo-resistance gene can be avoided, yet it will still be available in case continued diagnosis is desired during treatment. If the modified cells themselves become diseased, they could still be destroyed by inducing expression of a lethal polypeptide as described below.

The methods of the invention are carried out by introducing the polynucleotides encoding the gene switch and the reporter gene into cells of a subject. Any method known for introducing a polynucleotide into a cell known in the art, such as those described above, can be used.

In an alternative embodiment, the polynucleotides encoding the gene switch and the reporter gene are introduced into non-autologous cells, e.g., cells that are allogeneic or xenogeneic to the subject.

When the polynucleotides are to be introduced into cells ex vivo, the cells may be obtained from a subject by any technique known in the art, including, but not limited to, biopsies, scrapings, and surgical tissue removal. The isolated cells may be cultured for a sufficient amount of time to allow the polynucleotides to be introduced into the cells, e.g., 2, 4, 6, 8, 10, 12, 18, 24, 36, 48, hours or more. Methods for culturing primary cells for short periods of time are well known in the art. For example, cells may be cultured in plates (e.g., in microwell plates) either attached or in suspension.

For ex vivo diagnosis methods, cells are isolated from a subject and cultured under conditions suitable for introducing the polynucleotides into the cells. Once the polynucleotides have been introduced into the cells, the cells are incubated for a sufficient period of time to allow the ligand-dependent transcription factor to be expressed, e.g., 0.5, 1, 2, 3, 4, 5, 6, 7, 8, 9, 10, 12, 18, or 24 hours or more. If expression of the ligand-dependent transcription factor is increased or decreased compared to control levels (i.e., if the subject has the disease or disorder and the promoters controlling expression of the transcription factor are activated or deactivated), the presence and/or level of the ligand-dependent transcription factor is detected by the addition of ligand, leading to expression of the reporter gene at a level corresponding to the level of the ligand-dependent transcription factor. The ligand may be added to the cells at any time before, during or after introduction of the polynucleotides into the cells. The optimal timing of ligand administration can be determined for each type of cell and disease or disorder using only routine techniques. In one embodiment, the ligand may be added, reporter gene expression determined, the ligand removed, and the process repeated one or more times to obtain multiple diagnostic measurements of the cells. In another embodiment, ligand is continuously present and reporter gene expression is measured periodically.

The first in vivo diagnostic embodiment of the invention (modification of isolated cells followed by reintroduction of the cells to the subject) may be used where the ex vivo method using isolated cells is insufficient, e.g., where circulating factors are necessary for diagnostic switch promoter activity to occur. In this embodiment, cells are isolated from a subject and the polynucleotides are introduced into the cells in culture as described above. At some point after the introduction of the polynucleotides into the cells, the cells are introduced back into the subject. Reintroduction may be carried out by any method known in the art, e.g., intravenous infusion or direct injection into a tissue or cavity. In one embodiment, the presence of the polynucleotides in the cells is determined prior to introducing the cells back into the subject. In another embodiment, cells containing the polynucleotides are selected (e.g., based on the presence of a selectable marker in the polynucleotides) and only those cells containing the polynucleotides are reintroduced into the subject. After the cells are reintroduced to the subject, ligand is administered to the subject and reporter gene expression is assayed. The ligand may be administered by any suitable method, either systemically (e.g., orally, intravenously) or locally (e.g., intraperitoneally, intrathecally, intraventricularly, direct injection into the tissue or organ where the cells were reintroduced). The optimal timing of ligand administration can be determined for each type of cell and disease or disorder using only routine techniques. In one embodiment, the ligand may be administered, reporter gene expression determined, the ligand removed, and the process repeated one or more times to obtain multiple diagnostic measurements of the cells. In another embodiment, ligand is continuously administered and reporter gene expression is measured periodically. The detection of reporter gene expression after ligand is administered can occur in vivo or ex vivo. For example, if the reporter gene encodes a secreted protein that circulates in the blood, detection of the protein can occur in a blood sample removed from the patient. If the reporter gene encodes a protein that produces a luminescent or fluorescent signal, the signal may be detected in vive. In another embodiment, a sample of the modified cells can be removed and expression of the reporter gene detected ex vivo.

The second in vivo diagnostic embodiment of the invention involves direct in vivo introduction of the polynucleotides into the cells of the subject. The polynucleotides may be introduced into the subject systemically or locally (e.g., at the site of the suspected disease or disorder). Once the polynucleotides have been introduced to the subject, the ligand may be administered and reporter gene expression assayed. The ligand may be administered by any suitable method, either systemically (e.g., orally, intravenously) or locally (e.g., intraperitoneally, intrathecally, intraventricularly, direct injection into the tissue or organ where the suspected disease or disorder is occurring). The optimal timing of ligand administration can be determined for each type of cell and disease or disorder using only routine techniques. In one embodiment, the ligand may be added, reporter gene expression determined, the ligand removed, and the process repeated one or more times to obtain multiple diagnostic measurements of the cells containing the polynucleotides. In another embodiment, ligand is continuously administered and reporter gene expression is measured periodically. The detection of reporter gene expression after ligand is administered can occur in vivo or ex vivo. For example, if the reporter gene encodes a secreted protein that circulates in the blood, detection of the protein can occur in a blood sample removed from the patient. If the reporter gene encodes a protein that produces a luminescent or fluorescent signal, the signal may be detected in vivo. In another embodiment, a sample of the modified cells can be removed and expression of the reporter gene detected ex vivo.

When non-autologous cells are used in the diagnostic methods, the cells may be obtained from any source, e.g., other subjects, cell lines, or animals. The non-autologous cells may be any cells that are viable after transplantation, such as fibroblasts or stem cells (e.g., embryonic stem cells, hematopoietic stem cells). The non-autologous cells are isolated and the polynucleotides are introduced into the cells in culture as described above. At some point after the introduction of the polynucleotides into the cells, the cells are introduced into the subject. Introduction may be carried out by any method known in the art, e.g., intravenous infusion or direct injection into a tissue or cavity. In one embodiment, the presence of the polynucleotides in the cells is determined prior to introducing the cells back into the subject. In another embodiment, cells containing the polynucleotides are selected (e.g., based on the presence of a selectable marker in the polynucleotides) and only those cells containing the polynucleotides are introduced into the subject. In one embodiment, the non-autologous cells are surrounded by a barrier (e.g., encapsulated) prior to introduction into the subject. After the cells are introduced to the subject, ligand is administered to the subject and reporter gene expression is assayed. The ligand may be administered by any suitable method, either systemically (e.g., orally, intravenously) or locally (e.g., intraperitoneally, intrathecally, intraventricularly, direct injection into the tissue or organ where the cells were introduced). The optimal timing of ligand administration can be determined for each type of cell and disease or disorder using only routine techniques. In one embodiment, the ligand may be administered, reporter gene expression determined, the ligand removed, and the process repeated one or more times to obtain multiple diagnostic measurements of the cells. In another embodiment, ligand is continuously administered and reporter gene expression is measured periodically. The detection of reporter gene expression after ligand is administered can occur in vivo or ex vivo. For example, if the reporter gene encodes a secreted protein that circulates in the blood, detection of the protein can occur in a blood sample removed from the patient. If the reporter gene encodes a protein that produces a luminescent or fluorescent signal, the signal may be detected in vivo. In another embodiment, a sample of the modified cells can be removed and expression of the reporter gene detected ex vivo.

In all in vivo embodiments, the polynucleotides or vector comprising the polynucleotides may comprise a sequence encoding a lethal polypeptide that can be turned on to express a product that will kill a cell containing the polynucleotides or vector. Lethal polypeptide expression can be used to eliminate the modified cells from a subject, either because diagnostic tests are no longer needed or because of a problem with the modified cells (e.g., hyperproliferation or toxicity). A lethal polypeptide, as used herein, is a polypeptide that, when expressed, is lethal to the cell that expresses the polypeptide, either because the polypeptide itself is lethal or the polypeptide produces a compound that is lethal. As used herein, a lethal polypeptide includes polypeptides that induce cell death in any fashion, including but not limited to, necrosis, apoptosis and cytotoxicity. Examples of lethal polypeptides include, but are not limited to, apoptosis inducing tumor suppressor genes such as, but not limited to, p53, Rb and BRCA-1, toxins such as diphtheria toxin (DTA), shigella neurotoxin, botulism toxin, tetanus toxin, cholera toxin, CSE-V2 and other variants of scorpion protein toxins to name a few, suicide genes such as cytosine deaminase and thymidine kinase, and cytotoxic genes, e.g., tumor necrosis factor, interferon-alpha. The present invention is not limited by the identity of the lethal polypeptide, provided that the polypeptide is capable of being lethal to the cell in which it is expressed. If the modified cells are short-lived cells (e.g., cells with a limited lifespan (e.g., about 10 days or less, such as dendritic cells), it may not be necessary to include a lethal polypeptide in the polynucleotides or vector as the cells will be naturally removed over a short period of time.

Another aspect of the invention relates to methods of monitoring progression of a disease or disorder by administering to cells of the subject the diagnostic gene switches of the invention and measuring reporter gene expression to monitor progression of the disease or disorder. In one embodiment, the invention relates to methods of monitoring the progression of a disease or disorder in a subject, comprising:
(a) introducing into cells of said subject (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor, to produce modified cells;
(b) administering ligand to said modified cells; and
(c) detecting reporter gene expression at least twice;
wherein a change in the level of expression of said reporter gene indicates progression of said disease or disorder in said subject.

Progression may be indicated by increasing or decreasing reporter gene expression depending on whether the diagnostic switch promoters are responsive to factor(s) that increase or decrease during progression of the disease or disorder. These methods may be carried out using any of the variants of the diagnostic methods described above (i.e., ex vivo cells, modification of cells ex vivo followed by reintroduction of the cells in vivo, or in vivo). A disease or disorder is monitored by measuring reporter gene expression at least twice as an indication of the state of the disease or disorder and noting any change in the level of expression. In one embodiment, the monitoring can be carried out by exposing the cells to ligand continuously and measuring reporter gene expression intermittently. In another embodiment, the monitoring can be carried out by exposing cells to ligand intermittently and measuring reporter gene expression during each exposure.

One embodiment of the invention relates to methods of preparing modified cells for monitoring the progression of a disease or disorder in a subject, comprising introducing into cells of said subject (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor, to produce modified cells.

Another embodiment of the invention relates to methods of monitoring the progression of a disease or disorder in a subject, comprising:
(a) administering ligand to modified cells of said subject; and
(b) detecting reporter gene expression at least twice;
wherein a change in the level of expression of said reporter gene indicates progression of said disease or disorder in said subject; and
wherein said modified cells of said subject comprise (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor.

In a further embodiment, the methods of monitoring progression of a disease or disorder are carried out using non-autologous cells, e.g., cells that are allogeneic or xenogeneic to the subject, and the modified non-autologous cells are introduced into the subject. In one embodiment, the non-autologous cells are surrounded by a barrier (e.g., encapsulated) prior to being introduced into the subject. One embodiment of the invention relates to methods of monitoring the progression of a disease or disorder in a subject, comprising:
(a) introducing into non-autologous cells (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor, to produce modified cells;
(b) introducing said modified cells into said subject;
(c) administering ligand to said modified cells; and
(d) detecting reporter gene expression at least twice;
wherein a change in the level of expression of said reporter gene indicates progression of said disease or disorder in said subject.

A further aspect of the invention relates to methods of monitoring the effectiveness of a treatment for a disease or disorder in a subject, comprising administering to the subject a treatment and carrying out the diagnostic methods of the invention at least twice to determine if reporter gene expression is increasing, decreasing, or remaining the same. In one embodiment, the invention relates to methods of monitoring the effectiveness of a treatment for a disease or disorder in a subject, comprising:
(a) administering said treatment to said subject;
(b) introducing into cells of said subject (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor, to produce modified cells;
(c) administering ligand to said modified cells; and
(d) detecting reporter gene expression at least twice;
wherein a change in the level of expression of said reporter gene indicates the effectiveness of said treatment.

A change in the level of expression of the reporter gene after the treatment is administered is an indication of the effectiveness of the treatment. A decrease in reporter gene expression indicates the treatment is effective if the diagnostic switch promoter(s) are responsive to factor(s) that are elevated in the disease or disorder. An increase in reporter gene expression indicates the treatment is effective if the diagnostic switch promoter(s) are responsive to factor(s) that are reduced in the disease or disorder. If reporter gene expression does not change after administration of the treatment, it may indicate that the treatment has halted the progression of the disease or disorder. These methods may be carried out using any of the variants of the diagnostic methods described above (i.e., ex vive cells, modification of cells ex vive followed by reintroduction of the cells in vivo, in vivo).

For the ex vive embodiment of the invention, cells may be isolated from the subject before treatment to determine baseline levels of reporter gene expression. After the treatment is administered to the subject, cells may be isolated from the subject at various intervals to determine reporter gene expression.

For the in vivo embodiments of the invention, modified cells or the polynucleotides can be introduced into a subject before, during, or after administration of the treatment. If the cells or polynucleotides are administered prior to the treatment, a baseline level of reporter gene expression can be obtained.

The measurement of reporter gene expression may be carried out ex vivo or in vivo. In one embodiment, the monitoring can be carried out by exposing the cells to ligand continuously and measuring reporter gene expression intermittently. In another embodiment, the monitoring can be carried out by exposing cells to ligand intermittently and measuring reporter gene expression during each exposure.

In one embodiment, one or both of the polynucleotides encoding a gene switch and a reporter gene may be part of a therapeutic vector that is being administered to a subject (e.g., a vector encoding a therapeutic protein or nucleic acid for gene therapy). In this embodiment, the therapeutic treatment and the diagnostic test for monitoring effectiveness of the treatment are administered together in one unit, ensuring that all cells that receive the treatment also receive the diagnostic gene switch.

One embodiment of the invention relates to methods of preparing modified cells for monitoring the effectiveness of a treatment for a disease or disorder in a subject, comprising introducing into cells of said subject (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor, to produce modified cells.

Another embodiment of the invention relates to methods of monitoring the effectiveness of a treatment for a disease or disorder in a subject, comprising:
(a) administering said treatment to said subject;
(b) administering ligand to modified cells of said subject; and
(c) detecting reporter gene expression at least twice;
wherein a change in the level of expression of said reporter gene indicates the effectiveness of said treatment; and
wherein said modified cells of said subject comprise (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor.

In a further embodiment, the methods of monitoring the effectiveness of a treatment for a disease or disorder are carried out using non-autologous cells, e.g., cells that are allogeneic or xenogeneic to the subject, and the modified non-autologous cells are introduced into the subject. In one embodiment, the non-autologous cells are surrounded by a barrier (e.g., encapsulated) prior to being introduced into the subject. In one embodiment the invention relates to methods of monitoring the effectiveness of a treatment for a disease or disorder in a subject, comprising:
(a) introducing into non-autologous cells (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder, and (2) a polynucleotide encoding a reporter gene linked to a promoter which is activated by said ligand-dependent transcription factor, to produce modified cells;
(b) introducing said modified cells into said subject;
(c) administering ligand to said modified cells; and
(d) detecting reporter gene expression at least twice;
wherein a change in the level of expression of said reporter gene indicates the effectiveness of said treatment.

Another aspect of the invention relates to methods of monitoring the potential toxicity of an administered treatment for a disease or disorder in a subject. In one embodiment, the invention relates to methods of monitoring the potential toxicity of an administered treatment for a disease or disorder in a subject, comprising: administering said treatment to said subject;
(a) introducing into cells of said subject (1) a polynucleotide encoding a gene switch, said gene switch comprising at least one transcription factor sequence, wherein said at least one transcription factor sequence encodes a ligand-dependent transcription factor, linked to a diagnostic switch promoter, wherein the activity of the promoter is modulated by factors found in cells that are being exposed to toxic conditions, and (2) a polynucleotide encoding a reporter gene linked to a promoter which is activated by said ligand-dependent transcription factor, to produce modified cells;
(b) administering ligand to said modified cells; and
(c) detecting reporter gene expression at least twice;
wherein a change in the level of expression of said reporter gene indicates the toxicity of said treatment.

In one embodiment, this aspect involves polynucleotides in which the transcription factor sequence(s) are under the control of promoters that are regulated by factors found in cells that are being exposed to toxic conditions, e.g., cells that are stressed or dying. Examples include, without limitation, promoters responsive to apoptosis signals, necrosis signals, hypoxia, reactive oxygen species, DNA or chromatin modification, protein degradation, oxidative/reductive state, changes in pH, etc. Suitable stress promoters include those disclosed in U.S. Published Application No. 2003/0027127 (incorporated herein by reference) and include, without limitation, promoters from the following genes: CYP1A1, GST Ya, GADD45, GRP78, JUN, FOS, XHF, HSP70, MT IIA, GADD153, ALDH 1, HMO, CRE, XRE, NFrxBRE, RARE, ThRE, PPRE, TRE, ERE, and p53RE. Suitable apoptosis-responsive promoters include, without limitation, Fas/CD95, TRAMP, TNF RI, DR1, DR2, DR3, DR4, DR5, DR6, FADD, RIP, TNFα, Fas ligand, TRAILR1, TRAILR2, TRAILR3, Bcl-2, p53, BAX, BAD, Akt, CAD, PI3 kinase, PP1, and caspase proteins. Detection of an increase in reporter gene expression following administration of a treatment is an indication that the treatment is harmful to the cells. By making the gene switch responsive to stress or death signals, it can be used to monitor the effects of a treatment and detect toxic effects on the cellular level long before the subject exhibits overt symptoms of toxicity.

These methods may be carried out using any of the variants of the diagnostic methods described above (i.e., ex vivo cells, modification of cells ex vivo followed by reintroduction of the cells in vivo, in vivo).

For the ex vivo embodiment of the invention, cells may be isolated from the subject before treatment to determine baseline levels of reporter gene expression. After the treatment is administered to the subject, cells may be isolated from the subject at various intervals to determine reporter gene expression.

For the in vivo embodiments of the invention, modified cells or the polynucleotides can be introduced into a subject before, during, or after administration of the treatment. If the cells or polynuclcotides are administered prior to the treatment, a baseline level of reporter gene expression can be obtained.

The measurement of reporter gene expression may be carried out er vive or in vivo. In one embodiment, the monitoring can be carried out by exposing the cells to ligand continuously and measuring reporter gene expression intermittently. In another embodiment, the monitoring can be carried out by exposing cells to ligand intermittently and measuring reporter gene expression during each exposure.

One embodiment of the invention relates to methods of preparing modified cells for monitoring the potential toxicity of an administered treatment for a disease or disorder in a subject, comprising introducing into cells of said subject (1) a polynucleotide encoding a gene switch, said gene switch comprising at least one transcription factor sequence, wherein said at least one transcription factor sequence encodes a ligand-dependent transcription factor, linked to a diagnostic switch promoter, wherein the activity of the promoter is modulated by factors found in cells that are being exposed to toxic conditions, and (2) a polynucleotide encoding a reporter gene linked to a promoter which is activated by said ligand-dependent transcription factor, to produce modified cells.

Another embodiment of the invention relates to methods of monitoring the potential toxicity of an administered treatment for a disease or disorder in a subject, comprising:
(a) administering said treatment to said subject;
(b) administering ligand to modified cells of said subject; and
(c) detecting reporter gene expression at least twice;
wherein a change in the level of expression of said reporter gene indicates the toxicity of said treatment; and
wherein said modified cells of said subject comprise (1) a polynucleotide encoding a gene switch, said gene switch comprising at least one transcription factor sequence, wherein said at least one transcription factor sequence encodes a ligand-dependent transcription factor, linked to a diagnostic switch promoter, wherein the activity of the promoter is modulated by factors found in cells that are being exposed to toxic conditions, and (2) a polynucleotide encoding a reporter gene linked to a promoter which is activated by said ligand-dependent transcription factor.

In a further embodiment, the methods of monitoring the potential toxicity of an administered treatment for a disease or disorder are carried out using non-autologous cells, e.g., cells that are allogeneic or xenogeneic to the subject, and the modified non-autologous cells are introduced into the subject. In one embodiment, the non-autologous cells are surrounded by a barrier (e.g., encapsulated) prior to being introduced into the subject. In one embodiment, the invention relates to methods of monitoring the potential toxicity of an administered treatment for a disease or disorder in a subject, comprising:
(a) introducing into non-autologous cells (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated by factors found in cells that are being exposed to toxic conditions, and (2) a polynucleotide encoding a reporter gene linked to a promoter which is activated by said ligand-dependent transcription factor, to produce modified cells;
(b) introducing said modified cells into said subject;
(c) administering ligand to said modified cells; and
(d) detecting reporter gene expression at least twice;
wherein a change in the level of expression of said reporter gene indicates the toxicity of said treatment.

In another embodiment of the invention, the polynucleotide comprises transcription factor sequence(s) that are under the control of promoters that are activated by the factor which is being administered as the treatment (e.g., gene therapy treatment with a therapeutic protein or nucleic acid). By making the gene switch responsive to the administered treatment, it can be used to monitor expression of the gene therapy treatment and detect undesirably high or low levels of the treatment long before the subject exhibits overt symptoms of overexpression or underexpression of the therapeutic factor. In one embodiment, the invention relates to methods of monitoring the level of a factor that is being administered to a subject for treatment for a disease or disorder, comprising: administering said treatment to said subject;
(a) introducing into cells of said subject (1) a polynucleotide encoding a gene switch, said gene switch comprising at least one transcription factor sequence, wherein said at least one transcription factor sequence encodes a ligand-dependent transcription factor, linked to a diagnostic switch promoter, wherein the activity of the promoter is modulated by said factor that is being administered for treatment, and (2) a polynucleotide encoding a reporter gene linked to a promoter which is activated by said ligand-dependent transcription factor, to produce modified cells;
(b) administering ligand to said modified cells; and
(c) detecting reporter gene expression;
wherein the level of expression of said reporter gene indicates the level of the factor being administered for treatment.

These methods may be carried out using any of the variants of the diagnostic methods described above (i.e., ex vivo cells, modification of cells ex vivo followed by reintroduction of the cells in vivo, in vivo).

For the ex vivo embodiment of the invention, cells may be isolated from the subject before treatment to determine baseline levels of reporter gene expression. After the treatment is administered to the subject, cells may be isolated from the subject at various intervals to determine reporter gene expression.

For the in vivo embodiments of the invention, modified cells or the polynucleotides can be introduced into a subject before, during, or after administration of the treatment. If the cells or polynucleotides are administered prior to the treatment, a baseline level of reporter gene expression can be obtained.

The measurement of reporter gene expression may be carried out ex vivo or in vivo. In one embodiment, the monitoring can be carried out by exposing the cells to ligand continuously and measuring reporter gene expression intermittently. In another embodiment, the monitoring can be carried out by exposing cells to ligand intermittently and measuring reporter gene expression during each exposure.

One embodiment of the invention relates to methods of preparing modified cells for monitoring the level of a factor that is being administered to a subject for treatment for a disease or disorder, comprising introducing into cells of said subject (1) a polynucleotide encoding a gene switch, said gene switch comprising at least one transcription factor sequence, wherein said at least one transcription factor sequence encodes a ligand-dependent transcription factor, linked to a diagnostic switch promoter, wherein the activity of the promoter is modulated by said factor that is being administered for treatment, and (2) a polynucleotide encoding a reporter gene linked to a promoter which is activated by said ligand-dependent transcription factor, to produce modified cells.

Another embodiment of the invention relates to method of monitoring the level of a factor that is being administered to a subject for treatment for a disease or disorder, comprising:
(a) administering said treatment to said subject;
(b) administering ligand to modified cells of said subject; and
(c) detecting reporter gene expression;
wherein the level of expression of said reporter gene indicates the level of the factor being administered for treatment; and
wherein said modified cells of said subject comprise (1) a polynucleotide encoding a gene switch, said gene switch comprising at least one transcription factor sequence, wherein said at least one transcription factor sequence encodes a ligand-dependent transcription factor, linked to a diagnostic switch promoter, wherein the activity of the promoter is modulated by said factor that is being administered for treatment, and (2) a polynucleotide encoding a reporter gene linked to a promoter which is activated by said ligand-dependent transcription factor.

In a further embodiment, the methods of monitoring the level of a factor that is being administered to a subject for treatment for a disease or disorder are carried out using non-autologous cells, e.g., cells that are allogeneic or xenogeneic to the subject, and the modified non-autologous cells are introduced into the subject. In one embodiment, the non-autologous cells are surrounded by a barrier (e.g., encapsulated) prior to being introduced into the subject. A method of monitoring the level of a factor that is being administered to a subject for a disease or disorder in a subject, comprising:
(a) introducing into non-autologous cells (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated by said factor that is being administered for treatment, and (2) a polynucleotide encoding a reporter gene linked to a promoter which is activated by said ligand-dependent transcription factor, to produce modified cells;
(b) introducing said modified cells into said subject;
(c) administering ligand to said modified cells; and
(d) detecting reporter gene expression;
wherein the level of expression of said reporter gene indicates the level of the factor being administered for treatment.

Another aspect of the invention relates to methods of detecting transplant rejection in a subject that has received an organ or tissue transplant, comprising:
(a) introducing into cells of said organ or tissue transplant (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during transplant rejection, and (2) a polynucleotide encoding a reporter gene linked to a promoter which is activated by said ligand-dependent transcription factor, to produce modified cells;
(b) administering ligand to said modified cells; and
(c) detecting reporter gene expression;
wherein expression of the reporter gene indicates that transplant rejection has been detected.

An additional embodiment of the invention relates to methods of monitoring the progression of transplant rejection in a subject that has received an organ or tissue transplant, comprising:
(a) introducing into cells of said organ or tissue transplant (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during transplant rejection, and (2) a polynucleotide encoding a reporter gene linked to a promoter which is activated by said ligand-dependent transcription factor, to produce modified cells;
(b) administering ligand to said modified cells; and
(c) detecting reporter gene expression at least twice;
wherein a change in the level of expression of said reporter gene indicates progression of said transplant rejection in said subject.

The methods for detecting and monitoring transplant rejection in a transplant recipient can be used to monitor the viability of transplanted organs or tissues. The ability to detect the onset of transplant rejection will allow a medical practitioner to adjust treatment of the transplant patient accordingly, e.g., by adjusting the level of immunosuppression therapy. The sensitivity of the present methods may allow for earlier detection of rejection than is possible with the current method of taking periodic tissue biopsies to look for tissue damage. The earlier detection of the occurrence of rejection in a subject will allow for a more rapid response and avoidance of further damage to the transplanted organs or tissues. The methods may be used for any organ or tissue transplant, including, without limitation, heart, kidney, lung, liver, pancreas, small and large intestine, skin, cornea, bone marrow, bone, ligament, tendon, neural tissue, and stem cell transplants.

In the methods of the invention the gene switch comprises one or more diagnostic switch promoters that are activated during transplant rejection, i.e., rejection promoters. A rejection promoter is any promoter that is activated in a transplanted organ or tissue when the rejection process begins to occur. Examples of rejection promoters that are useful in the present invention include, without limitation, promoters from the genes listed in Table 4, along with the organs in which increased expression has been detected during rejection.

TABLE 4

| Gene | Organ/Tissue |
| --- | --- |
| A Disintegrin And Metalloproteinase 17 (ADAM17) | Kidney |
| A Disintegrin And Metalloproteinase 19 (ADAM19) | Kidney |
| AGT | Kidney |
| Allograft Inflammatory Factor-1 (AIF-1) | Liver |
| Angiotensin II Type 1 Receptor (AGTR1) | Heart |
| APAF1 | Intestine |
| β2-Defensin | Lung |

TABLE 4-continued

| Gene | Organ/Tissue |
|---|---|
| Brain Natriuretic Peptide | Heart |
| C-Reactive Protein (CRP) | Liver |
| C3 | Kidney |
| CCL1 | Heart |
| CCL3 | Heart |
| CCL4 | Heart |
| CCL5 | Heart |
| CCR5 | Heart |
| CD3 | Kidney |
| CD95 | Liver |
| CD95 Ligand | Liver, Heart |
| CD103 | Kidney |
| Cellular Mediator of Immune Response (MIR) | Heart |
| CFLAR | Heart |
| Chemokine (C—X—C motif) Ligand 9 (CXCL9) | Heart |
| Collagen Type IX α3 | Kidney |
| Collagenase | Lung |
| Connective Tissue Growth Factor (CTGF) | Kidney |
| CX3CR1 | Heart |
| CXCR3 | Pancreas, Heart, Kidney |
| Cyclooxygenase-2 (COX-2) | Kidney, Heart |
| Early Growth Response Gene-1 (EGR-1) | Lung, Heart |
| ENA 78 | Heart |
| Eotaxin | Cornea |
| Epidermal Growth Factor Receptor (EGFR) | Kidney |
| EPST11 | Intestine |
| Fas | Heart |
| Fas Ligand | Kidney, Heart, Pancreas |
| Fork-Head Activin Signal Transducer-1 (FAST-1) | Heart |
| FOXP3 | Kidney |
| Fractalkine | Kidney, Heart |
| Gamma 2 | Kidney |
| Granulysin | Kidney |
| Granzyme B | Kidney, Pancreas, Intestine, Heart, Lung |
| Heat Shock Protein-60 (HSP-60) | Intestine |
| Heat Shock Protein-70 (HSP-70) | Intestine |
| Hepatocyte Growth Factor (HGF) | Heart |
| IF127 | Intestine |
| Integrin-α4 (ITGA4) | Heart |
| Interferon-γ | Kidney, Intestine, Heart |
| Interferon-Inducible Protein 10 (IP-10; CXCL10) | Kidney, Heart, Pancreas |
| Interleukin-2 (IL-2) | Heart |
| Interleukin-2 Receptor (IL-2R) | Intestine |
| Interleukin-4 (IL-4) | Kidney |
| Interleukin-15 (IL-15) | Heart, Lung |
| Interleukin-18 (IL-18) | Kidney |
| Intracellular Adhesion Molecule-1 (ICAM-1) | Kidney |
| Laminin | Kidney |
| LAP3 | Intestine |
| Macrophage Inflammatory Protein-2 (MIP-2) | Cornea |
| MADCAM-1 | Intestine |
| Matrix Metalloproteinase-2 (MMP-2) | Intestine, Kidney |
| Matrix Metalloproteinase-9 (MMP-9) | Kidney, Intestine |
| Matrix Metalloproteinase-11 (MMP-11) | Kidney |
| Matrix Metalloproteinase-12 (MMP-12) | Kidney |
| Matrix Metalloproteinase-14 (MMP-14) | Kidney |
| MDK | Intestine |
| MIG | Pancreas, Heart |
| MIP-1α | Cornea, Pancreas, Heart, Kidney |
| MIP-1β | Cornea, Heart |
| Monocyte Chemotactic Protein-1 (MCP-1) | Cornea, Pancreas, Heart |
| Monocyte Chemotactic Protein-2 (MCP-2) | Heart |
| MUC2 | Intestine |
| MUC4 | Intestine |
| NKG2D | Kidney |
| p16 (INK4a) | Kidney |
| p21 (WAF/CIP1) | Kidney |
| p27 (Kip1) | Kidney |
| Perforin | Kidney, Pancreas, Intestine, Heart |
| Programmed Cell Death (PDCD1) | Heart |
| RANTES | Cornea, Pancreas, Kidney, Heart |
| RAS Homolog Gene Family, Member U (RHOU) | Heart |
| Semaphorin 7A (SEMA7A) | Heart |
| Serine Proteinase Inhibitor-9 (PI-9) | Kidney |
| SOD2 | Heart |
| STK6 | Intestine |
| Surfactant Protein-C (SP-C) | Kidney |
| TIAF-1 | Kidney, Liver |
| TIM-3 | Kidney |
| Tissue Inhibitor of Metalloproteinase-1 (TIMP-1) | Kidney |
| Tissue Inhibitor of Metalloproteinase-2 (TIMP-2) | Kidney |
| Transforming Growth Factor-β1 (TGF-β1) | Intestine, Kidney, Heart |
| Transforming Growth Factor Type I Receptor | Intestine |
| Tumor Necrosis Factor-α (TNF-α) | Intestine, Heart, Kidney |
| Urokinase Plasminogen Activator (uPA) | Kidney |
| Urokinase Plasminogen Activator Receptor (uPAR) | Kidney |
| Vascular Cell Adhesion Molecule-1 (VCAM-1) | Kidney, Lung |
| Vasoactive Intestinal Peptide (VIP) | Intestine |
| WD Repeat Dommoain 40A (WDR40A) | Heart |
| XCL1 | Heart |

In one embodiment of the invention, the polynucleotides comprising the rejection promoters are administered to the organ or tissue to be transplanted prior to the transplantation process. Organs and tissues that are used for transplantation typically must be transplanted into a recipient within 24-48 hours after removal from the donor. In one embodiment, the polynucleotides of the invention are administered to the organ or tissue within 48 hours of removal from the donor, e.g., within 36, 24, 18, 12, or 6 hours of removal from the donor. In another embodiment, the polynucleotides are administered to the organ or tissue at least 48 hours prior to transplantation into the recipient, e.g., at least 36, 24, 18, 12, or 6 hours prior to transplantation. The polynucleotides may be introduced into the organ or tissue to be transplanted in one location or in more than one location within the organ or tissue, e.g., 2, 3, 4, 5, 6, 7, 8, 9, 10 or more locations.

In another embodiment, the polynucleotides are administered to the organ or tissue after it has been transplanted into a subject, e.g., 2, 4, 6, 8, 10, 12, or 18 hours, 1, 2, 3, 4, 5, or 6 days, or 1, 2, 3, or 4 weeks or more after the transplantation.

The polynucleotides may be administered to the organ or tissue by any means as discussed above, including direct injection, electroporation, viral delivery, etc. In other embodiments, the polynucleotides may be administered as part of transgenic cells, e.g., transgenic stem cells. The cells may be isolated from either the transplant donor or the transplant recipient. For example, stem cells may be isolated from a patent in need of a transplant and the polynucleotides of the invention introduced into the stem cells. The transgenic cells may then be stored (e.g., frozen) until an organ or tissue is available for transplantation. The transgenic cells may then be administered to the organ or tissue before or after transplantation.

In a further embodiment, the methods of detecting transplant rejection may be carried out by introducing the polynucleotides of the invention into non-autologous cells, e.g., cells that are allogeneic or xenogeneic to the organ or tissue being transplanted, and the modified non-autologous cells are introduced to the organ or tissue prior to transplantation. In one embodiment, the modified non-autologous cells are surrounded by a barrier (e.g., encapsulated) prior to being introduced into the organ or tissue.

In one embodiment of the invention, the gene switch comprises a single rejection promoter operably linked to a transcription factor sequence. In another embodiment, the gene switch comprises two rejection promoters that are operably linked to two different transcription factor sequences that together encode a ligand-dependent transcription factor. The two rejection promoters may be the same or different.

Figure 4:
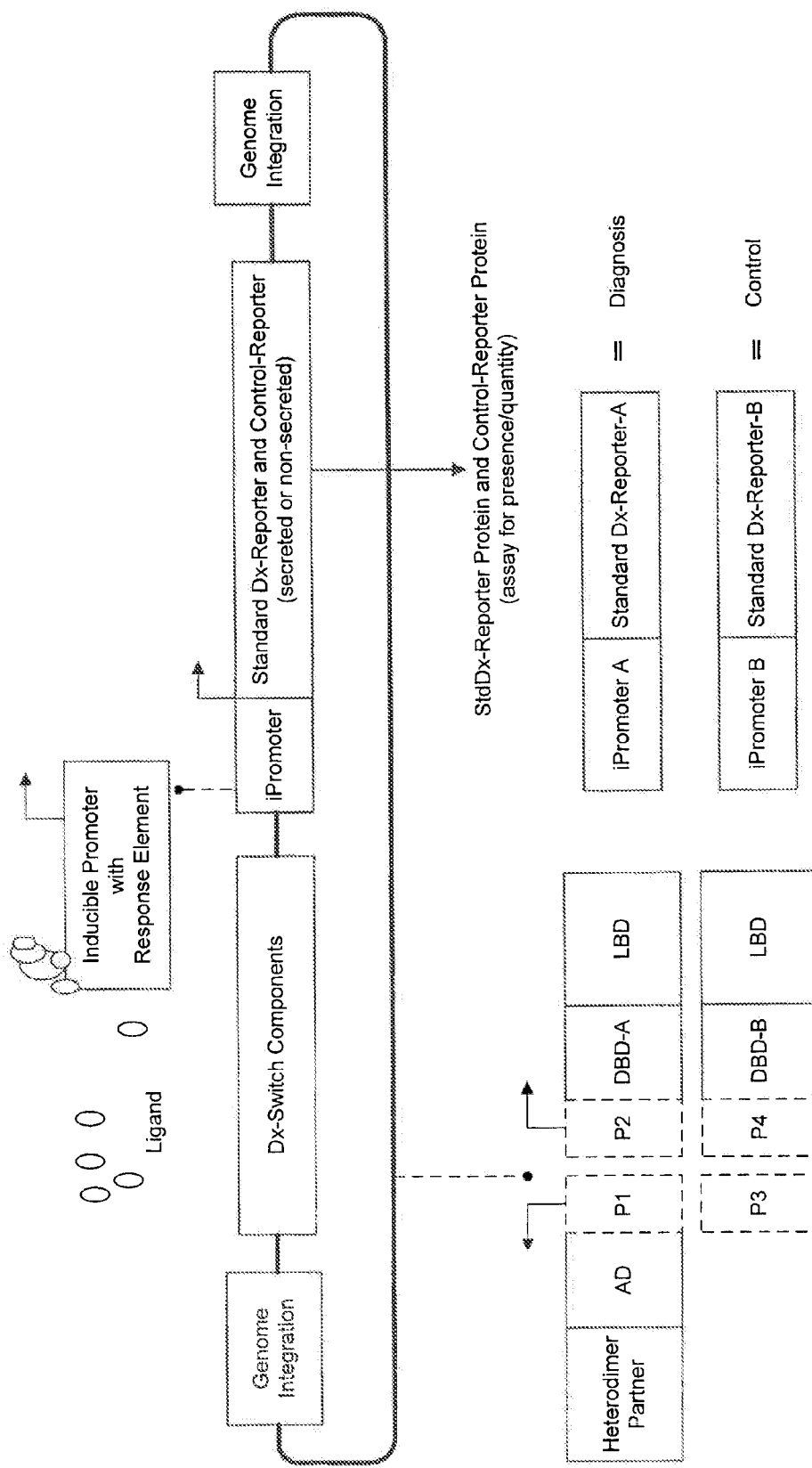

In another embodiment, the gene switch may further comprise a promoter that regulates expression of a control protein that is useful for monitoring the function of the gene switch, i.e., to show that the gene switch is operating properly in its environment, e.g., has not been subjected to gene silencing. The expression of the control protein may be used to limit false negative results from the diagnostic switch. In one embodiment, the promoter linked to the control protein is a constitutive promoter so that the control protein is always expressed. In a different embodiment, the promoter linked to the control protein is a switch promoter which is different from the rejection promoter(s) present in the gene switch. The control protein may be a ligand-dependent transcription factor that binds to a promoter operably linked to a second reporter gene that is different from the first reporter gene. For example, the control protein may be a ligand-dependent transcription factor having a different DNA binding domain than the transcription factor expressed from the rejection promoter(s), and that recognizes the response elements in the promoter operably linked to the second reporter gene as shown in FIG. 4.

In one embodiment of the methods for detecting or monitoring transplant rejection, the reporter gene is any reporter gene described above. In another embodiment, the reporter gene encodes a secreted protein, e.g., one that can be readily detected in a blood or urine sample of a transplant recipient. In another embodiment, the reporter gene encodes a protein that is endogenous to the transplant recipient, e.g., a protein that is normally expressed at low levels so that an increase in reporter gene expression upon the onset of rejection can be detected.

Once the polynucleotides of the invention have been administered to the organ or tissue transplant, the methods of detecting or monitoring transplant rejection may be carried out by detecting reporter gene expression. In one embodiment, the level of reporter gene expression may be measured once. In another embodiment, the level of reporter gene expression may be measured more than once, e.g., regularly, such as once every 1, 2, 3, 4, 5, 6 days, 1, 2, 3, 4 weeks, or every 1, 2, 3, 4, 5, 6 or more months. At each time point to be measured, a measurement of reporter gene expression may be made in the absence of ligand to get a background level of expression and in the presence ligand to obtain the level of reporter gene expression due to activation of the rejection promoter(s). In one embodiment, the level of reporter gene expression in the presence of ligand is determined shortly after transplantation (e.g., within 1, 2, 3, 4, 5, 6 days or 1, 2, 3, or 4 weeks) to obtain the ligand-induced baseline level of reporter gene expression prior to the occurrence of any transplant rejection. The initial timepoint (or any subsequent timepoint) can be used to determine how much ligand must be administered to the subject and how long the ligand must be present to obtain measurable reporter gene expression. Both the dose and time may be adjusted as needed for each subject. Regular monitoring of ligand-induced reporter gene expression may then be carried out to detect any increase in reporter gene expression, which is indicative of transplant rejection.

If a polynucleotide encoding a control protein (either constitutive or inducible) is present in the gene switch, the level of the control protein or the reporter gene induced by the control protein may be measured at the same time to confirm that the gene switch is functioning properly. If the gene switch is not functioning optimally, it may be necessary to increase the ligand concentration or the amount of time between ligand administration and reporter gene detection to increase the signal from the gene switch. In another embodiment, if the gene switch is no longer functioning, additional polynucleotides may be administered to the organ or tissue transplant so that monitoring of transplant rejection can be continued.

In a further embodiment, once an increase in reporter gene expression has been detected indicating the presence of transplant rejection, the diagnosis may be confirmed using traditional means, e.g., by obtaining a biopsy of the transplanted tissue.

One embodiment of the invention relates to methods of preparing on organ or tissue transplant for detecting transplant rejection in a subject, comprising introducing into cells of said organ or tissue transplant (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during transplant rejection, and (2) a polynucleotide encoding a reporter gene linked to a promoter which is activated by said ligand-dependent transcription factor, to produce modified cells.

Another embodiment of the invention relates to methods of detecting transplant rejection in a subject that has received an organ or tissue transplant, comprising:
(a) administering ligand to said subject; and
(b) detecting reporter gene expression;
wherein expression of the reporter gene indicates that transplant rejection has been detected; and
wherein said organ or tissue transplant comprises one or more cells comprising (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during transplant rejection, and (2) a polynucleotide encoding a reporter gene linked to a promoter which is activated by said ligand-dependent transcription factor.

One embodiment of the invention relates to methods of preparing an organ or tissue transplant for monitoring the progression of transplant rejection in a subject, comprising introducing into cells of said organ or tissue transplant (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during transplant rejection, and (2) a polynucleotide encoding a reporter gene linked to a promoter which is activated by said ligand-dependent transcription factor, to produce modified cells.

Another embodiment of the invention relates to methods of monitoring the progression of transplant rejection in a subject that has received an organ or tissue transplant, comprising:
(a) administering ligand to said subject; and
(b) detecting reporter gene expression at least twice;
wherein a change in the level of expression of said reporter gene indicates progression of said transplant rejection in said subject, and
wherein said organ or tissue transplant comprises one or more cells comprising (1) a polynucleotide encoding a gene switch, said gene switch comprising at least one transcription factor sequence, wherein said at least one transcription factor sequence encodes a ligand-dependent transcription factor, operably linked to a diagnostic switch promoter, wherein the activity of the promoter is modulated during transplant rejection, and (2) a polynucleotide encoding a reporter gene linked to a promoter which is activated by said ligand-dependent transcription factor.

In a further embodiment, the methods of monitoring transplant rejection may be carried out by introducing the polynucleotides of the invention into non-autologous cells, e.g., cells that are allogeneic or xenogeneic to the organ or tissue being transplanted, and the modified non-autologous cells are introduced to the organ or tissue prior to transplantation. In one embodiment, the modified non-autologous cells are surrounded by a barrier (e.g., encapsulated) prior to being introduced into the organ or tissue.

In one embodiment of the methods described above, one or both of the polynucleotides encoding a gene switch and a reporter gene may be part of a therapeutic vector that is being administered to a subject (e.g., a vector encoding a therapeutic factor (protein or nucleic acid) for gene therapy). In this embodiment, the factor and the diagnostic test for monitoring the level of the factor are administered together in one unit, ensuring that all cells that receive the treatment also receive the diagnostic gene switch.

For each of the methods described above, in one embodiment, the polynucleotide encoding the gene switch and the polynucleotide encoding the reporter gene linked to a promoter are part of one larger polynucleotide, e.g., a vector. In another embodiment, the polynucleotide encoding the gene switch and the polynucleotide encoding the reporter gene linked to a promoter are separate polynucleotides.

In one aspect, the invention relates to polynucleotides that may be used in the methods of the invention. In one embodiment, the polynucleotide encodes a gene switch, the gene switch comprising at least one transcription factor sequence, wherein said at least one transcription factor sequence encodes a ligand-dependent transcription factor, operably linked to a diagnostic switch promoter, wherein the activity of the promoter is modulated during said disease or disorder. In another embodiment, the polynucleotide further encodes a reporter gene linked to a promoter which is activated by said ligand-dependent transcription factor. In one embodiment, the gene switch is an EcR-based gene switch. In another embodiment, the gene switch comprises a first transcription factor sequence under the control of a first diagnostic switch promoter and a second transcription factor sequence under the control of a second diagnostic switch promoter, wherein the proteins encoded by said first transcription factor sequence and said second transcription factor sequence interact to form a protein complex which functions as a ligand-dependent transcription factor. In one embodiment, the first diagnostic switch promoter and the second diagnostic switch promoter are different. In another embodiment, the first diagnostic switch promoter and the second diagnostic switch promoter are the same. In another embodiment, the first transcription factor sequence encodes a protein comprising a heterodimer partner and a transactivation domain and the second transcription factor sequence encodes a protein comprising a DNA binding domain and a ligand-binding domain. In a further embodiment, the polynucleotide also encodes a lethal polypeptide operably linked to an inducible promoter.

In one aspect, the invention relates to polynucleotides encoding a gene switch, the gene switch comprising at least one transcription factor sequence, wherein said at least one transcription factor sequence encodes a ligand-dependent transcription factor, linked to a diagnostic switch promoter, wherein the activity of the promoter is modulated by factors found in cells that are being exposed to toxic conditions. In another embodiment, the polynucleotide further encodes a reporter gene linked to a promoter which is activated by said ligand-dependent transcription factor. In one embodiment, the gene switch is an EcR-based gene switch. In another embodiment, the gene switch comprises a first transcription factor sequence under the control of a first diagnostic switch promoter and a second transcription factor sequence under the control of a second diagnostic switch promoter, wherein the proteins encoded by said first transcription factor sequence and said second transcription factor sequence interact to form a protein complex which functions as a ligand-dependent transcription factor. In one embodiment, the first diagnostic switch promoter and the second diagnostic switch promoter are different. In another embodiment, the first diagnostic switch promoter and the second diagnostic switch promoter are the same. In another embodiment, the first transcription factor sequence encodes a protein comprising a heterodimer partner and a transactivation domain and the second transcription factor sequence encodes a protein comprising a DNA binding domain and a ligand-binding domain. In a further embodiment, the polynucleotide also encodes a lethal polypeptide operably linked to an inducible promoter.

In one aspect, the invention relates to polynucleotides encoding a gene switch, the gene switch comprising at least one transcription factor sequence, wherein said at least one transcription factor sequence encodes a ligand-dependent transcription factor, linked to a diagnostic switch promoter, wherein the activity of the promoter is modulated by said factor that is being administered for treatment. In another embodiment, the polynucleotide further encodes a reporter gene linked to a promoter which is activated by said ligand-dependent transcription factor. In one embodiment, the gene switch is an EcR-based gene switch. In another embodiment, the gene switch comprises a first transcription factor sequence under the control of a first diagnostic switch promoter and a second transcription factor sequence under the control of a second diagnostic switch promoter, wherein the proteins encoded by said first transcription factor sequence and said second transcription factor sequence interact to form a protein complex which functions as a ligand-dependent transcription factor. In one embodiment, the first diagnostic switch promoter and the second diagnostic switch promoter are different. In another embodiment, the first diagnostic switch promoter and the second diagnostic switch promoter are the same. In another embodiment, the first transcription factor sequence encodes a protein comprising a heterodimer partner and a transactivation domain and the second transcription factor sequence encodes a protein comprising a DNA binding domain and a ligand-binding domain. In a further embodiment, the polynucleotide also encodes a lethal polypeptide operably linked to an inducible promoter.

In one aspect, the invention relates to polynucleotides encoding a gene switch, the gene switch comprising at least one transcription factor sequence, wherein said at least one transcription factor sequence encodes a ligand-dependent transcription factor, linked to a diagnostic switch promoter, wherein the activity of the promoter is modulated during transplant rejection. In another embodiment, the polynucleotide further encodes a reporter gene linked to a promoter which is activated by said ligand-dependent transcription factor. In one embodiment, the gene switch is an EcR-based gene switch. In another embodiment, the gene switch comprises a first transcription factor sequence under the control of a first diagnostic switch promoter and a second transcription factor sequence under the control of a second diagnostic switch promoter, wherein the proteins encoded by said first transcription factor sequence and said second transcription factor sequence interact to form a protein complex which functions as a ligand-dependent transcription factor. In one embodiment, the first diagnostic switch promoter and the second diagnostic switch promoter are different. In another embodiment, the first diagnostic switch promoter and the second diagnostic switch promoter are the same. In another embodiment, the first transcription factor sequence encodes a protein comprising a heterodimer partner and a transactivation domain and the second transcription factor sequence encodes a protein comprising a DNA binding domain and a ligand-binding domain. In a further embodiment, the polynucleotide also encodes a lethal polypeptide operably linked to an inducible promoter.

Another aspect of the invention relates to vectors comprising any of the polynucleotides described above. In one embodiment, the vector is a plasmid vector or a viral vector. In one embodiment, the polynucleotides are present on the same vector. In a further embodiment, each of the polynucleotides is on a separate vector. The separate vectors may be the identical vector (e.g., the same plasmid), the same type of vector (e.g., both are plasmids but not the same plasmid), or different types of vectors (e.g., one vector is a plasmid, the other vector is a virus).

In another aspect, the invention provides kits that may be used in conjunction with methods the invention. Kits according to this aspect of the invention may comprise one or more containers, which may contain one or more components selected from the group consisting of one or more nucleic acid molecules, restriction enzymes and one or more cells comprising such nucleic acid molecules. Kits of the invention may further comprise one or more containers containing cell culture media suitable for culturing cells of the invention, one or more containers containing antibiotics suitable for use in culturing cells of the invention, one or more containers containing buffers, one or more containers containing transfection reagents, one or more containers containing substrates for enzymatic reactions, and/or one or more ligands for gene switch activation.

Kits of the invention may contain a wide variety of nucleic acid molecules that can be used with the invention. Examples of nucleic acid molecules that can be supplied in kits of the invention include those that contain promoters, sequences encoding gene switches, enhancers, repressors, selection markers, transcription signals, translation signals, primer hybridization sites (e.g., for sequencing or PCR), recombination sites, restriction sites and polylinkers, sites that suppress the termination of translation in the presence of a suppressor tRNA, suppressor tRNA coding sequences, sequences that encode domains and/or regions, origins of replication, telomeres, centromeres, and the like. In one embodiment, kits may comprise a polynucleotide comprising a gene switch without any diagnostic switch promoters, the polynucleotide being suitable for insertion of any diagnostic switch promoters of interest. Nucleic acid molecules of the invention may comprise any one or more of these features in addition to polynucleotides as described above.

Kits of the invention may comprise cells. The cells may comprise the polynucleotides of the invention, or the cells and the polynucleotides may be in separate containers. In one embodiment the cells may be autologous cells, e.g., as part of a kit designed for a specific subject. In another embodiment, the cells may be non-autologous cells, e.g., as part of a kit designed for any subject. In a further embodiment, the non-autologous cells may be surrounded by a barrier (e.g., encapsulated).

Kits of the invention may comprise containers containing one or more recombination proteins. Suitable recombination proteins include, but are not limited to, Cre, Int, IHF, Xis, Flp, Fis, Hin, Gin, Cin, Tn3 resolvase, ΦC31, TndX, XerC, and XerD. Other suitable recombination sites and proteins are those associated with the GATEWAY™ Cloning Technology available from Invitrogen Corp., Carlsbad, Calif., and described in the product literature of the GATEWAY™ Cloning Technology (version E, Sep. 22, 2003), the entire disclosures of which are incorporated herein by reference.

Kits of the invention can also be supplied with primers. These primers will generally be designed to anneal to molecules having specific nucleotide sequences. For example, these primers can be designed for use in PCR to amplify a particular nucleic acid molecule. Sequencing primers may also be supplied with the kit.

One or more buffers (e.g., one, two, three, four, five, eight, ten, fifteen) may be supplied in kits of the invention. These buffers may be supplied at working concentrations or may be supplied in concentrated form and then diluted to the working concentrations. These buffers will often contain salt, metal ions, co-factors, metal ion chelating agents, etc. for the enhancement of activities or the stabilization of either the buffer itself or molecules in the buffer. Further, these buffers may be supplied in dried or aqueous forms. When buffers are supplied in a dried form, they will generally be dissolved in water prior to use.

Kits of the invention may contain virtually any combination of the components set out above or described elsewhere herein. As one skilled in the art would recognize, the components supplied with kits of the invention will vary with the intended use for the kits. Thus, kits may be designed to perform various functions set out in this application and the components of such kits will vary accordingly.

The present invention further relates to instructions for performing one or more methods of the invention. Such instructions can instruct a user of conditions suitable for performing methods of the invention. Instructions of the invention can be in a tangible form, for example, written instructions (e.g., typed on paper), or can be in an intangible form, for example, accessible via a computer disk or over the internet.

It will be recognized that a full text of instructions for performing a method of the invention or, where the instructions are included with a kit, for using the kit, need not be provided. One example of a situation in which a kit of the invention, for example, would not contain such full length instructions is where the provided directions inform a user of the kits where to obtain instructions for practicing methods for which the kit can be used. Thus, instructions for performing methods of the invention can be obtained from internet web pages, separately sold or distributed manuals or other product literature, etc. The invention thus includes kits that direct a kit user to one or more locations where instructions not directly packaged and/or distributed with the kits can be found. Such instructions can be in any form including, but not limited to, electronic or printed forms.

Having now fully described the invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

EXAMPLES

Example 1

Figure 5:
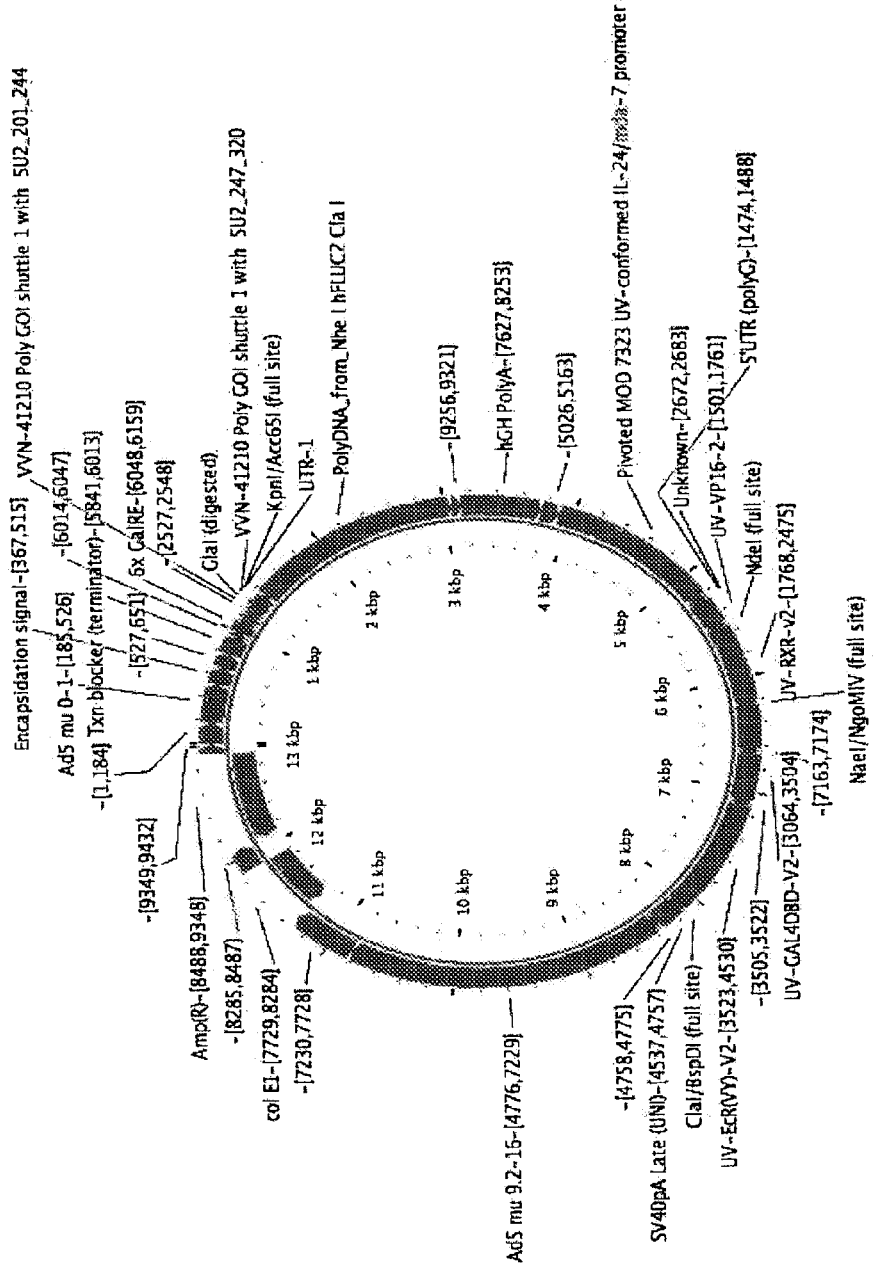
FIG. 5 shows an embodiment of a single promoter shuttle vector (SEQ ID No.: 5), which includes the IL-24/mda-7 promoter. Adenovirus produced using this vector is used to transduce cells isolated from lymphatic samples.

The vector shown in FIG. 5 includes IL-24/mda-7 promoter (SEQ ID NO.: 5). Adenovirus produced using the adenoviral shuttle vector is used to transduce cells isolated from lymphatic samples. The transduces cells are split into two groups and cultured either in the presence or absence of activator ligand. Both sets of cells are then disrupted, and the resulting cell lysates are used in luciferase assays.

Example 2

Figure 6:
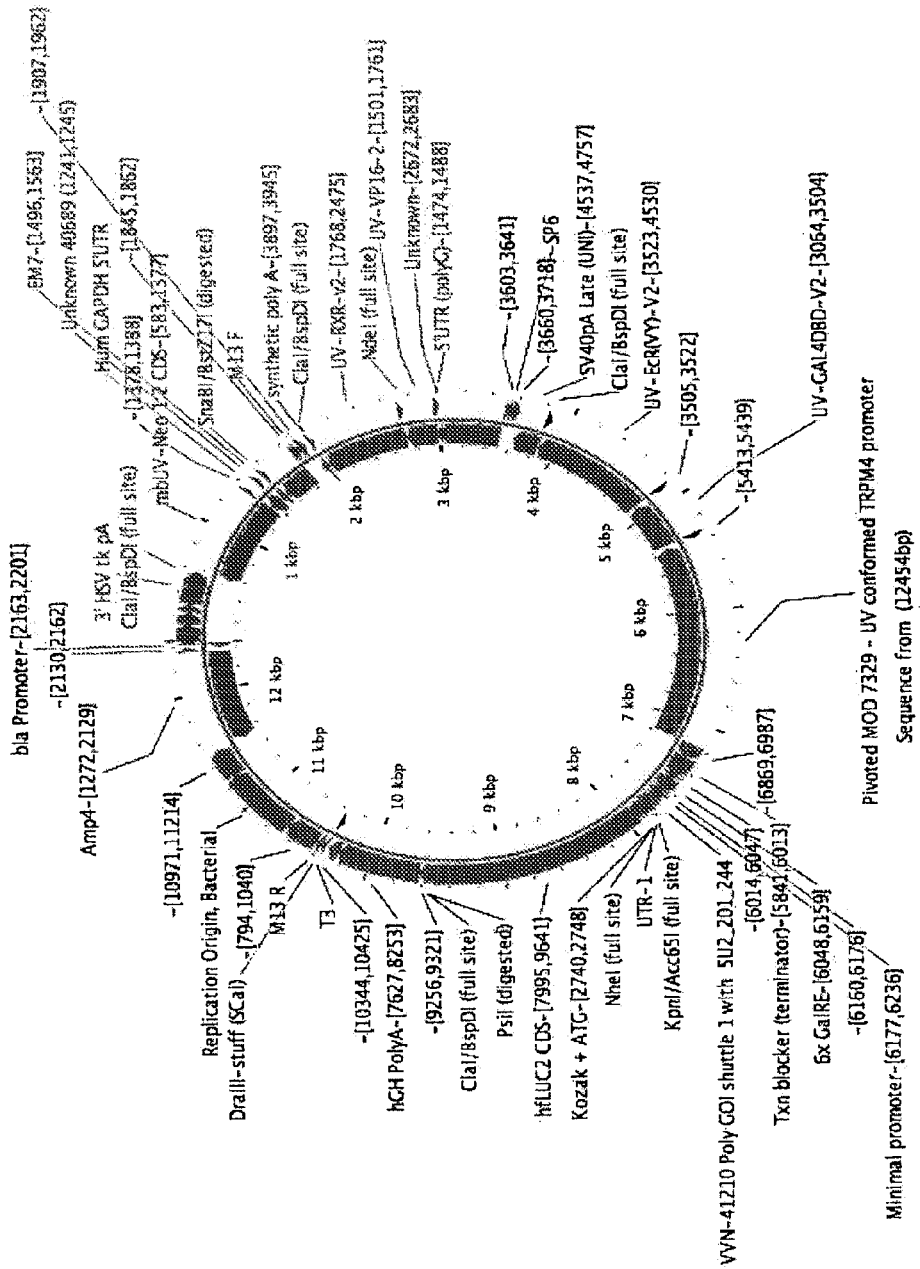
FIG. 6 shows an embodiment of a dual promoter vector (SEQ ID NO.: 6), which includes TRPM4 and TRGC1/TARP promoters. This DNA vector is used to transduce a prostate biopsy using non-viral transduction systems.

The vector shown in FIG. 6 includes TRPM4 and TRGC1/TARP promoters (SEQ ID NO.: 6). The DNA vector is used to transduce a prostate biopsy using non-viral transduction systems. The transduced biopsy is split into two groups and cultured either in the presence or absence of an activator ligand. Both sets of biopsied tissues are homogenized, and the resulting lysates are used in luciferase assays.

Example 3

Figure 7:
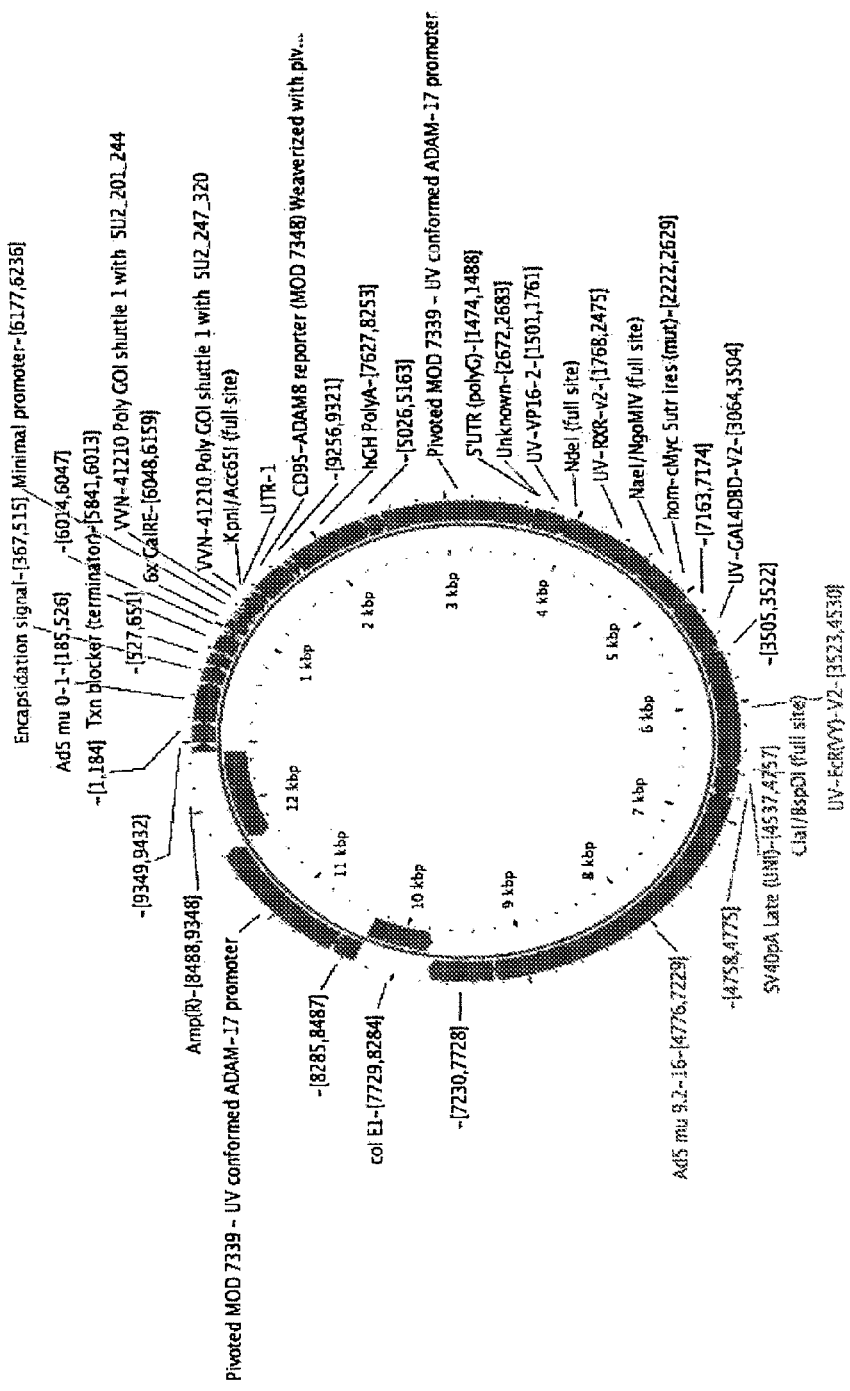
FIG. 7 shows an embodiment of a single promoter vector (SEQ ID NO.: 7), which includes the ADAM-17 promoter and the CD95-ADAM8 dual reporter (SEQ ID NO.: 10).

The vector shown in FIG. 7 includes the ADAM-17 promoter (SEQ ID NO.: 7) and the CD95-ADAM8 reporter (SEQ ID NOs: 10-11). Adenovirus produced using the adenoviral shuttle vector is used to transduced a portion of a donor kidney before transplantation. Following transplantation, serum samples are assayed for the reporter gene for a period defined by the physician. The assay protocol consists of assaying reporter expression from samples not exposed to activator ligand. Immediately after blood draw of the non-activated group, ligand is administered for 24 hours and then discontinued; another blood sample is acquired within one hour before the ligand treatment is completed. Reporter assay results are compared between the ligand-treated and untreated samples. A period of 60 hours must pass before this procedure is performed again.

Example 4

Figure 8:
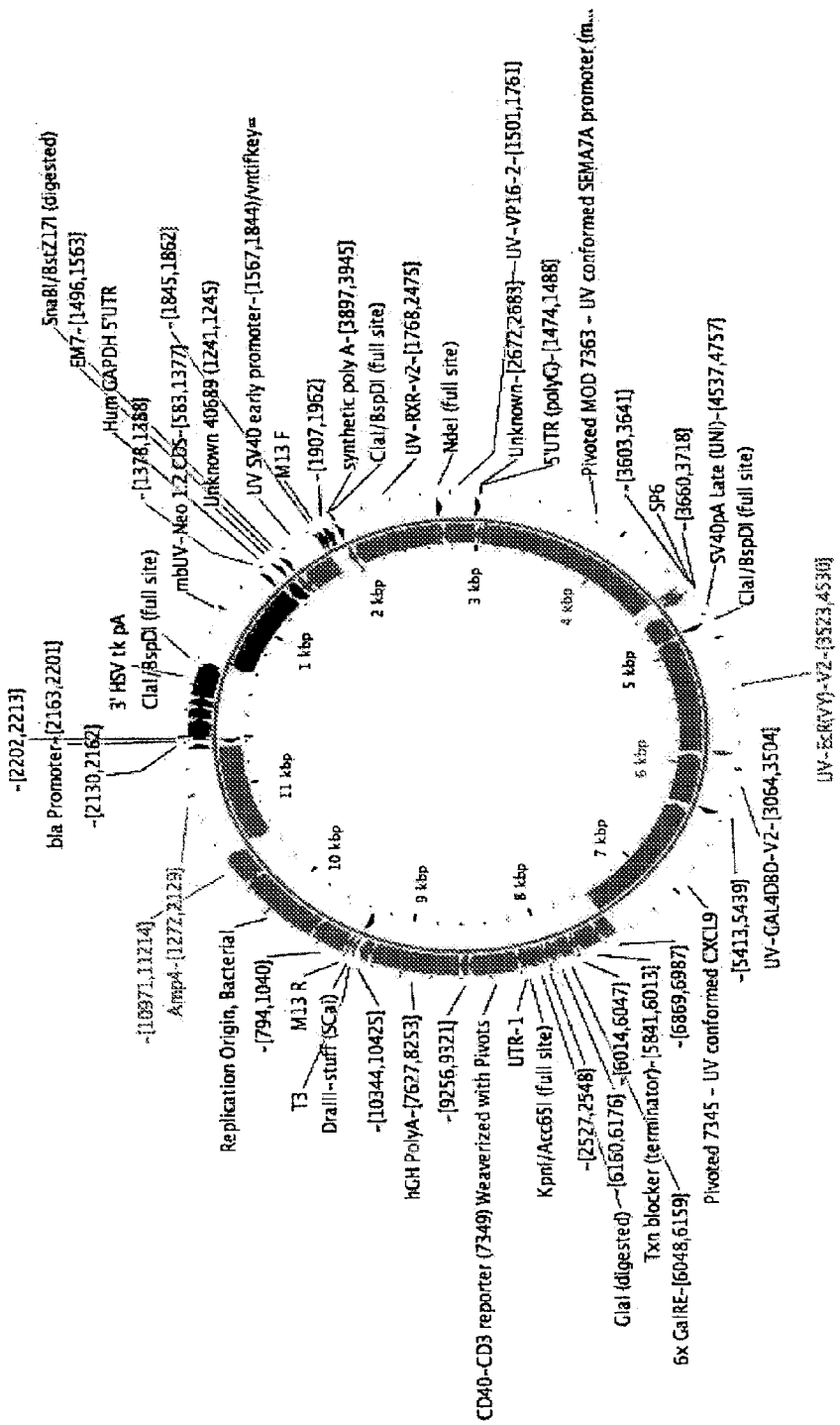
FIG. 8 shows an embodiment of a dual promoter vector (SEQ ID NO.: 8), which includes the CXCL9 and SEMA7A promoters and the CD40-CD3 dual reporter (SEQ ID NO.: 12).

The vector shown in FIG. 8 includes the CXCL9 and SEMA7A promoters (SEQ ID NO.: 8) and the CD40-CD3 reporter (SEQ ID NOs.: 12-13). This vector is used to transduce a portion of a donor heart before transplantation via direct needle injection. Following transplantation, serum samples are assayed for the reporter gene for a period defined by the physician. The assay protocol consists of assaying reporter expression from samples not exposed to an activator ligand. Immediately after the blood draw of the "non-activated" group, ligand is administered for 24 hours and then discontinued; another blood sample is acquired within one hour before the ligand treatment is completed. Reporter assay results are compared between the ligand-treated and untreated samples. A period of 60 hours must pass before this procedure can be performed again.

Example 5

Figure 9:
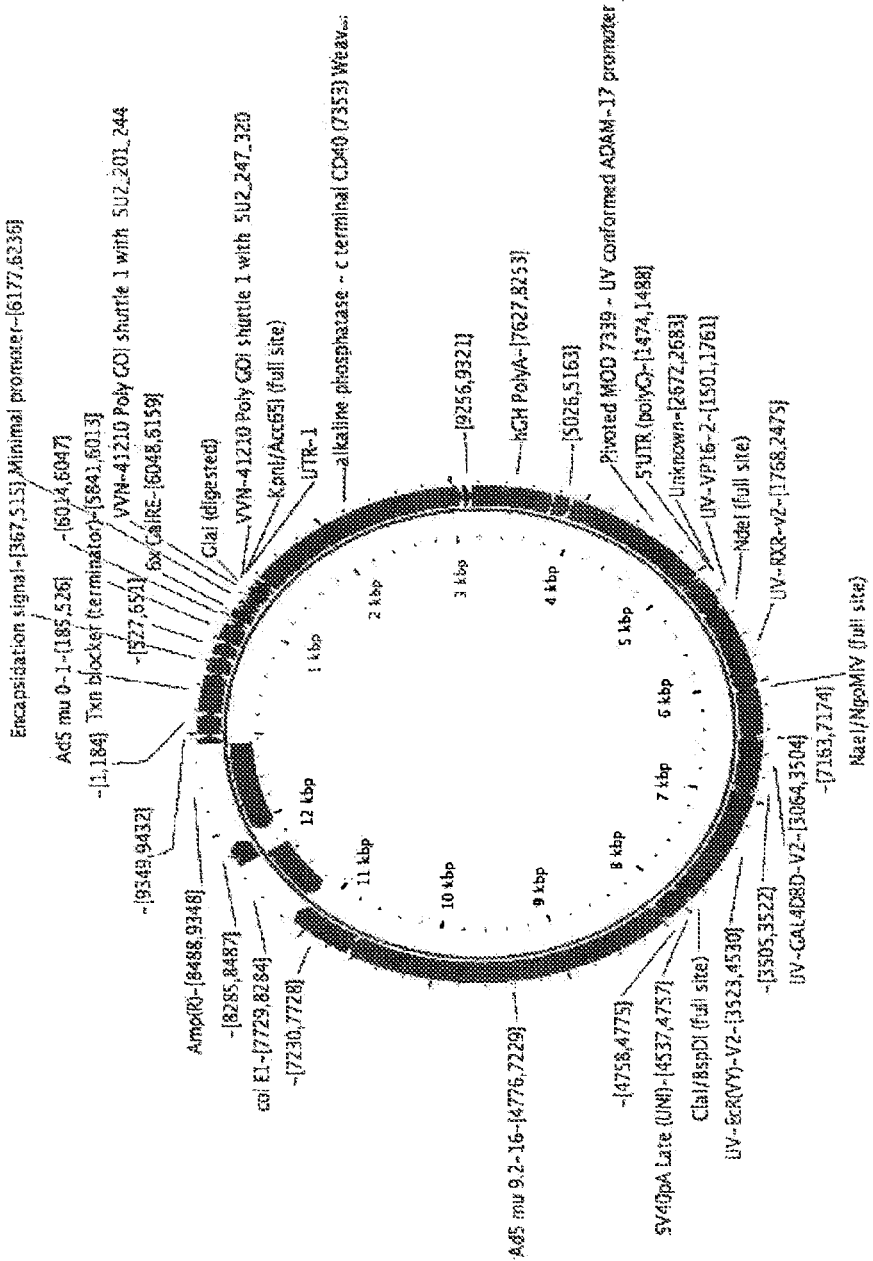
FIG. 9 shows an embodiment of a single promoter vector (SEQ ID NO.: 9), which includes the ADAM-17 promoter and the alkaline phosphatase—c terminal CD40 reporter (SEQ ID NO.: 14).

The vector shown in FIG. 9 includes the ADAM-17 promoter and the alkaline phosphatase—c terminal CD40 reporter (SEQ ID NO.: 14). Adenovirus produced using this adenoviral shuttle vector is used to transduce primary porcine kidney cells. The resulting cells are encapsulated in alginate (see WO 2007/046719A2), and then implanted into a donor kidney before transplantation. Following transplantation, serum samples are assayed for the reporter gene for a period defined by the physician. The assay protocol consists of assaying reporter expression from samples not exposed to activator ligand. Immediately after the blood draw of the "non-activated" group, ligand is administered for 24 hours and then discontinued; another blood sample is acquired within one hour before the ligand treatment is completed. Reporter assay results are compared between the ligand-treated and untreated samples. A period of 60 hours must pass before this procedure can be performed again.

What is claimed is:

1. A method of detecting kidney transplant rejection in a subject that has received a kidney transplant, comprising:
    introducing into cells of said organ or tissue transplant (1) a polynucleotide encoding a gene switch, said gene switch comprising at least one transcription factor sequence, wherein said at least one transcription factor sequence encodes a ligand-dependent transcription factor, operably linked to a diagnostic ADAM-17 switch promoter, wherein the activity of the promoter is modulated during transplant rejection, and (2) a polynucleotide encoding a CD95-ADAM8 dual reporter or a alkaline phosphatase—c terminal CD40 reporter gene linked to a promoter which is activated by said ligand-dependent transcription factor, to produce modified cells;
    administering ligand to said modified cells; and
    detecting reporter gene expression;
    wherein expression of the CD95-ADAM8 dual reporter or the alkaline phosphatase—c terminal CD40 reporter gene indicates that transplant rejection has been detected.

2. The method of claim 1, wherein said polynucleotides are introduced into said cells prior to transplantation.

3. The method of claim 1, wherein said polynucleotides are introduced into said cells after transplantation.

4. The method of claim 1, wherein said gene switch is an ecdysone receptor (EcR)-based gene switch.

5. The method of claim 4, wherein said ligand binds to the EcR ligand binding domain.

6. The method of claim 5, wherein said ligand is a diacylhydrazine.

7. The method of claim 6, wherein said ligand is selected from the group consisting of RG-115819, RG-115830, and RG-115932.

8. The method of claim 1, wherein one of said polynucleotides further encodes a lethal polypeptide operably linked to an inducible promoter.

* * * * *

SEQUENCE LISTING

```
<160> NUMBER OF SEQ ID NOS: 23

<210> SEQ ID NO 1
<211> LENGTH: 15
<212> TYPE: PRT
<213> ORGANISM: Artificial Sequence
<220> FEATURE:
<223> OTHER INFORMATION: Synthetic ecdysone receptor
<220> FEATURE:
<221> NAME/KEY: MISC_FEATURE
<222> LOCATION: (4)..(4)
<223> OTHER INFORMATION: X is Glycine or Threonine
<220> FEATURE:
<221> NAME/KEY: MISC_FEATURE
<222> LOCATION: (12)..(12)
<223> OTHER INFORMATION: X is Cysteine or Alanine

<400> SEQUENCE: 1

Arg Arg Gly Xaa Thr Cys Ala Asn Thr Gly Ala Xaa Cys Tyr Tyr
1               5                   10                  15

<210> SEQ ID NO 2
<211> LENGTH: 13
<212> TYPE: DNA
<213> ORGANISM: Artificial Sequence
<220> FEATURE:
<223> OTHER INFORMATION: Synthetic ecdysone receptor
```

```
<220> FEATURE:
<221> NAME/KEY: misc_feature
<222> LOCATION: (7)..(7)
<223> OTHER INFORMATION: n can be any nucleotide

<400> SEQUENCE: 2
aggtcanagg tca                                                         13

<210> SEQ ID NO 3
<211> LENGTH: 15
<212> TYPE: DNA
<213> ORGANISM: Artificial Sequence
<220> FEATURE:
<223> OTHER INFORMATION: Synthetic ecdysone receptor

<400> SEQUENCE: 3
gggttgaatg aattt                                                       15

<210> SEQ ID NO 4
<211> LENGTH: 18
<212> TYPE: DNA
<213> ORGANISM: Artificial Sequence
<220> FEATURE:
<223> OTHER INFORMATION: Synthetic homing endonuclease (HE) enzyme known
      as I-SceI

<400> SEQUENCE: 4
tagggataac agggtaat                                                    18

<210> SEQ ID NO 5
<211> LENGTH: 13028
<212> TYPE: DNA
<213> ORGANISM: Artificial Sequence
<220> FEATURE:
<223> OTHER INFORMATION: Synthetic promoter

<400> SEQUENCE: 5
taaacaaata gggggttccgc gcacatttcc ccgaaaagtg ccacctgacg tctaagaaac       60
cattattatc atgacattaa cctataaaaa taggcgtatc acgaggccct ttcgtcttca      120
agaaaattaa tcgcaccggt atctatgtcg ggtgcggaga agaggtaat gaaatggcag       180 ctagcatcat caataatata ccttattttg gattgaagcc aatatgataa tgaggggtg       240 gagtttgtga cgtggcgcgg ggcgtgggaa cggggcgggt gacgtagtag tgtgcggaa       300 gtgtgatgtt gcaagtgtgg cggaacacat gtaagcgacg gatgtggcaa aagtgacgtt      360
tttggtgtgc gccggtgtac acaggaagtg acaattttcg cgcggtttta ggcggatgtt      420
gtagtaaatt tgggcgtaac cgagtaagat ttggccattt tcgcgggaaa actgaataag      480
aggaagtgaa atctgaataa ttttgtgtta ctcatagcgc gtaatagtgc gccggtgtac      540
acaggaagtg acaattttcg cgcggtttta ggcggatgtt gtagtaaatt tgggcgtaac      600
cgagtaagat ttggccattt tcgcgggaaa actgaataag aggaagtgaa atctgaataa      660
ttttgtgtta ctcattttgt ctaggagat ccggtaccga tatcctagac aacgatgctg      720
agctaactat aacggtccta aggtagcgac cgcggagact aggtgtattt atctaagcga      780
tcgcttaatt aaggccggcc gccgcaataa aatatcttta ttttcattac atctgtgtgt      840
tggttttttg tgtgaatcca tagtactaac atacgctctc catcaaaaca aaacgaaaca      900
aaacaaacta gcaaaatagg ctgtccccag tgcaagtcca ggtgccagaa catttctcta      960
tccataatgc aggggtaccg ggtgatgacg gtgaaaacct ccaattgcgg agtactgtcc     1020
tccgagcgga gtactgtcct ccgagcggag tactgtcctc cgagcggagt actgtcctcc     1080
```

```
gagcggagta ctgtcctccg agcggagtac tgtcctccga gcggagagtc cccggggacc    1140
tagagggtat ataatgggtg ccttagctgg tgtgtgacct catcttcctg tacgccctg     1200 caggggcgcg ccacgcgtcg aagaaggtga gtaatcttaa catgctcttt tttttttttt    1260
ttgctaatcc cttttgtgtg ctgatgttag gatgacattt acaacaaatg tttgttcctg    1320
acaggaaaaa ccttgctggg taccttcgtt gccggacact tcttgtcctc tactttggaa    1380
aaaaggaatt gagagccgct agcgccacca tggaagatgc caaaaacatt aagaagggcc    1440
cagcgccatt ctacccactc gaagacggga ccgctggcga gcagctgcac aaagccatga    1500
agcgctacgc cctggtgccc ggcaccatcg cctttaccga cgcacatatc gaggtggaca    1560
ttacctacgc cgagtacttc gagatgagcg ttcggctggc agaagctatg aagcgctatg    1620
ggctgaatac aaaccatcgg atcgtggtgt gcagcgagaa tagcttgcag ttcttcatgc    1680
ccgtgttggg tgccctgttc atcggtgtgg ctgtggcccc agctaacgac atctacaacg    1740
agcgcgagct gctgaacagc atgggcatca gccagcccac cgtcgtattc gtgagcaaga    1800
aagggctgca aaagatcctc aacgtgcaaa agaagctacc gatcatacaa agatcatca     1860 tcatggatag caagaccgac taccaggggct tccaaagcat gtacaccttc gtgacttccc    1920
atttgccacc cggcttcaac gagtacgact tcgtgcccga gagcttcgac cgggacaaaa    1980
ccatcgccct gatcatgaac agtagtggca gtaccggatt gcccaagggc gtagccctac    2040
cgcaccgcac cgcttgtgtc cgattcagtc atgcccgcga ccccatcttc ggcaaccaga    2100
tcatccccga caccgctatt ctcagcgtgg tgccatttca ccacggcttc ggcatgttca    2160
ccacgctggg ctacttgatc tgcggctttc gggtcgtgct catgtaccgc ttcgaggagg    2220
agctattctt gcgcagcttg caagactata agattcaatc tgccctgctg gtgcccacac    2280
tatttagctt cttcgctaag agcactctca tcgacaagta cgacctaagc aacttgcacg    2340
agatcgccag cggcggagcg cctctcagca aggaggtagg tgaggccgtg gccaaacgct    2400
tccacctacc aggcatccgc cagggctacg gcctgacaga aacaaccagc gccattctga    2460 tcaccccga aggggacgac aagcctggcg cagtaggcaa ggtggtgccc ttcttcgagg     2520
ctaaggtggt ggacttggac acaggtaaga ccctgggtgt gaaccagcgc ggcgagctgt    2580
gcgtccgtgg ccccatgatc atgagcggct acgtgaacaa ccccgaggct acaaacgctc    2640
tcatcgacaa ggacggctgg ctgcacacgc gcgacatcgc ctactgggac gaggacgagc    2700
acttcttcat cgtggaccgg ctcaagagcc tgatcaaata caagggctac caggtagccc    2760
cagccgaact ggagagcatc ctgctgcaac accccaacat cttcgacgcc ggggtcgctg    2820
gcctgcccga cgacgatgct ggcgagctgc ccgccgcagt cgtcgtgctg aacacggta     2880 aaaccatgac cgagaaggag atcgtggact atgtggccag ccaggttaca accgccaaga    2940
agctgcgcgg tggtgttgtg ttcgtggacg aggtgcctaa aggactgacc ggcaagttgg    3000
acgcccgcaa gatccgcgag attctcatta aggccaagaa gggcggcaag atcgccgtgt    3060
aaatcgattg cgcaaagctt tcgcgatagg cgagaccaat gggtgtgtac gtagcggccg    3120
cgtcgacgat agcttgatgg gtggcatccc tgtgacccct ccccagtgcc tctcctggcc    3180
ctggaagttg ccactccagt gcccaccagc cttgtcctaa taaaattaag ttgcatcatt    3240
ttgtctgact aggtgtcctt ctataatatt atggggtgga gggggtggt atggagcaag     3300 gggcaagttg gaagacaac ctgtagggcc tgcgggtct attgggaacc aagctggagt      3360
gcagtggcac aatcttggct cactgcaatc tccgcctcct gggttcaagc gattctcctg    3420
```

```
cctcagcctc ccgagttgtt gggattccag gcatgcatga ccaggctcag ctaatttttg    3480 ttttttggt agagacgggg tttcaccata ttggccaggc tggtctccaa ctcctaatct     3540
caggtgatct acccaccttg gcctcccaaa ttgctgggat tacaggcgtg aaccactgct    3600
cccttccctg tccttctgat tttaaaataa ctataccagc aggaggacgt ccagacacag    3660
cataggctac ctggccatgc ccaaccggtg ggacatttga gttgcttgct tggcactgtc    3720
ctctcatgcg ttgggtccac tcagtagatg cctgttgaat tctgatttaa atcggtccgc    3780
gtacggcgtg gtaggtccga acgaatccat ggattaccct gttatcccta tccggagtta    3840
acctcgagga cttcggaact tctagaacca gaccgttcag tttaaacgct cttctccccc    3900
tcgagccata tggtctcagt cacaactact catctctgcc tctgtagcac gaaagcaatt    3960
agcaacaata tgtcaacaaa catatgtgac cccatgaaaa ctttatttat tatggatacg    4020
gaaacctgaa aataatgtct ttcttttgat tttttcccca atcattaaaa aacgtaaaaa    4080
ctactcttag gtcgcaaggt taagccattc tcagcttggc agtggcaggc tggatttggc    4140
ttgtgaccta cagttggcca atccctgatt cccaaaatgt attcctcagg gatgtgggca    4200
aatacttatg ggaagtgctg gattaaacag agttaagaag catcagacat ttccaggacg    4260
ggctagcaca tgccagggct ctctaactga cctcattgga ttcatctgtt tcatggagga    4320
tcttgcaaga caagaattcc tcaaacctag agtctgagga ctgtgctttg ggaaacactg    4380
ctctgcttga tgccctcact gggcacatgg tagaatctgg agctgagtgc cttgctagct    4440
ggagataggg tcagagctct tgactgccct ggcagtcttg acacatcacg ctgtctgtgt    4500 ccctgagtg gttcagagct acacaggcca agactagccc accagagcac caggcctccc    4560
agctttctgg gcttgtccat gcgtacattt ccttattctt cctggtttcc agaacctaag    4620
gagaggcaca ttttggttga gtgattataa ccctagggac catgggtagc tgcatgtcag    4680
gaaacactcc tcaacttcct ggccctgatg gattaaagga gaggtactta caggttattt    4740
cttcgctgtg gactactgtc ccagcatgaa tagggcatca ttattgaatt attttgacag    4800
gaaggagact ggtgtatgct gcacagtaat aatgtattta catgtgtaca gagtttacca    4860
agcacctctg tgttgttttt gccttttgttt attacacttg gacaaatttt ttaaaattta    4920
tacatgcaga gactgcagcg cagagaagct aagagacttg cccctgccca cacagccagt    4980
ggtagagcct gaactcaaac ccaggtctca tctcacctca ggggctgctt tccccatcgc    5040
tgtattgtcc ttaaagtgat gggtgactag gcaatgaagt aattctctag gaaagcatga    5100
ccaatttccc tttctccacc tccctctttt tcctccaccc ctcccccatc agccccata     5160 tatatgccca aatctccaca aagccttgct tgcctgcaaa cctttacttc tgaaatgact    5220
tccacgcatg cggggggggg gggggcaat tggccaccat gggcccccaag aagaaaagga   5280 aggtggcccc cccaccgac gtgagcctgg gcgacgagct gcacctggac ggcgaggacg    5340
tggccatggc ccacgccgac gccctggacg acttcgacct ggacatgctg gcgacggcg    5400 acagccccgg ccccggcttc accccccacg acagcgcccc ctacgcgcc ctggacatgg   5460 ccgacttcga gttcgagcag atgttcaccg acgccctggg catcgacgag tacggcggcc    5520
atatggagat gccccgtggac aggattctgg aggccgaact cgccgtggag cagaaaagcg    5580
accagggcgt ggagggcccc ggcggaaccg gcggcagcgg cagcagcccc aacgaccccg    5640
tgaccaacat ctgccaggcc gccgacaagc agctgttcac cctggtggag tgggccaaga    5700
ggattcccca cttcagcagc ctgccctgg acgaccaggt gatcctgctg agggccggat    5760
ggaacgagct gctgatcgcc agcttcagcc acaggagcat cgacgtgagg gacggcatcc    5820
```

```
tgctggccac cggcctgcac gtccatagga acagcgccca cagcgccgga gtgggcgcca    5880
tcttcgacag ggtgctgacc gagctggtga gcaagatgag ggacatgagg atggacaaga    5940
ccgagctggg ctgcctgagg gccatcatcc tgttcaaccc cgaggtgagg ggcctgaaaa    6000
gcgcccagga ggtggagctg ctgagggaga aggtgtacgc cgccctggag gagtacacca    6060
ggaccaccca ccccgacgag cccggcagat tcgccaagct gctgctgagg ctgcccagcc    6120
tgaggagcat cggcctgaag tgcctggagc acctgttctt cttcaggctg atcggcgacg    6180
tgcccatcga caccttcctg atggagatgc tggagagccc cagcgacagc tgagccggca    6240
actcgctgta gtaattccag cgagaggcag agggagcgag cgggcggcgg gctagggtgg    6300
aggagcccgg cgagcagagc tgcgctgcgg gcgtcctggg aagggagatc cggagcgaat    6360
agggggcttc gcctctggcc cagccctccc gctgatcccc cagccagcgg tgcgcaaccc    6420
tagccgcatc cacgaaactt tgcccatagc agcgggcggg cactttgcac tggaacttac    6480
aacacccgag caaggacgcg actctcccga cgcggggagg ctattctgcc catttgggga    6540
cacttccccg ccgctgccag gacccgcttc tctgaaaggc tctccttgca gctgcttaga    6600
cgctggattt ttttcgggta gtggaaaacc agcagcctcc cgcgaccaga tctgccacca    6660
tgaagctgct gagcagcatc gagcaggctt gcgacatctg caggctgaag aagctgaagt    6720
gcagcaagga aagcccaagt gcgccaagt gcctgaagaa caactgggag tgcagataca    6780
gccccaagac caagaggagc cccctgacca gggcccacct gaccgaggtg gagagcaggc    6840
tggagaggct ggagcagctg ttcctgctga tcttccccag gaaggacctg acatgatcc    6900
tgaagatgga cagcctgcaa gacatcaagg ccctgctgac cggcctgttc gtgcaggaca    6960
acgtgaacaa ggacgccgtg accgacaggc tggccagcgt ggagaccgac atgcccctga    7020
cctgaggca gcacaggatc agcgccacca gcagcagcga ggagagcagc aacaagggcc    7080
agaggcagct gaccgtgagc cccgagtttc ccgggatcag gcccgagtgc gtggtgcccg    7140
agacccagtg cgccatgaaa aggaaggaga agaaggccca aaggagaag acaagctgc    7200
ccgtgagcac caccaccgtc gatgaccaca tgcccccat catgcagtgc gagcccccc    7260
cccccgaggc cgccaggatt cacgaggtcg tgcccaggtt cctgagcgac aagctgctgg    7320
tgaccaacag gcagaagaac atcccccagc tgaccgccaa ccagcagttc ctgatcgcca    7380
ggctgatctg gtatcaggac ggctacgagc agcccagcga cgaggacctg aaaaggatca    7440
cccagacctg gcagcaggcc gacgacgaga acgaggagag cgacacccc ttcaggcaga    7500
tcaccgagat gaccatcctg accgtgcagc tgatcgtgga gttcgccaag ggcctgcccg    7560
gattcgccaa gatcagccag cccgaccaga tcaccctgct gaaggcttgc agcagcgagg    7620
tgatgatgct gagggtggcc aggaggtacg acgccgccag cgacagcatc ctgttcgcca    7680
acaaccaggc ttacaccagg acaactaca ggaaggctgg catggccgag gtgatcgagg    7740
acctcctgca cttctgcaga tgtatgtaca gcatggccct ggacaacatc cactacgccc    7800
tgctgaccgc cgtggtgatc ttcagcgaca ggcccggcct ggagcagccc cagctggtgg    7860
aggagatcca gaggtactac ctgaacaccc tgaggatcta catcctgaac cagctgagcg    7920
gcagcgccag gagcagcgtg atctacggca agatcctgag catcctgagc gagctgagga    7980
ccctgggaat gcagaacagc aatatgtgta tcagcctgaa gctgaagaac aggaagctgc    8040
ccccccttcct ggaggagatt tgggacgtgg ccgacatgag ccacacccag ccccccccca    8100
tcctggagag ccccaccaac ctgtgaatcg attagacatg ataagataca ttgatgagtt    8160
```

```
tggacaaacc acaactagaa tgcagtgaaa aaaatgctta atttgtgaaa tttgtgatgc    8220
tattgcttaa tttgtaacca ttataagctg caataaacaa gttaataaaa catttgcatt    8280
cattttatgt ttcaggttca gggggagatg tgggaggttt tttaaagcaa gtaaaacctc    8340
tacaaatgtg gtatctagag ctcttccaaa tagatctgga aggtgctgag gtacgatgag    8400
acccgcacca ggtgcagacc ctgcgagtgt ggcggtaaac atattaggaa ccagcctgtg    8460
atgctggatg tgaccgagga gctgaggccc gatcacttgg tgctggcctg cacccgcgct    8520
gagtttggct ctagcgatga agatacagat tgaggtactg aaatgtgtgg gcgtggctta    8580
agggtgggaa agaatatata aggtgggggt cttatgtagt tttgtatctg ttttgcagca    8640
gccgccgccg ccatgagcac caactcgttt gatggaagca ttgtgagctc atatttgaca    8700
acgcgcatgc ccccatgggc cggggtgcgt cagaatgtga tgggctccag cattgatggt    8760
cgccccgtcc tgcccgcaaa ctctactacc ttgacctacg agaccgtgtc tggaacgccg    8820
ttggagactg cagcctccgc cgccgcttca gccgctgcag ccaccgcccg cgggattgtg    8880
actgactttg ctttcctgag cccgcttgca agcagtgcag cttcccgttc atccgcccgc    8940
gatgacaagt tgacggctct tttggcacaa ttggattctt tgacccggga acttaatgtc    9000
gtttctcagc agctgttgga tctgcgccag caggtttctg ccctgaaggc ttcctcccct    9060
cccaatgcgg tttaaaacat aaataaaaaa ccagactctg tttggatttg atcaagcaa    9120 gtgtcttgct gtctttattt aggggttttg cgcgcgcggt aggcccggga ccagcggtct    9180
cggtcgttga gggtcctgtg tattttttcc aggacgtggt aaaggtgact ctggatgttc    9240
agatacatgg gcataagccc gtctctgggg tggaggtagc accactgcag agcttcatgc    9300
tgcggggtgg tgttgtagat gatccagtcg tagcaggagc gctgggcgtg gtgcctaaaa    9360
atgtctttca gtagcaagct gattgccagg ggcaggccct tggtgtaagt gtttacaaag    9420
cggttaagct gggatgggtg catacgtggg gatatgagat gcatcttgga ctgtatttttt   9480 aggttggcta tgttcccagc catatccctc cggggattca tgttgtgcag aaccaccagc    9540
acagtgtatc cggtgcactt gggaaatttg tcatgtagct tagaaggaaa tgcgtggaag    9600
aacttggaga cgcccttgtg acctccaaga ttttccatgc attcgtccat aatgatggca    9660
atgggcccac gggcggcggc ctgggcgaag atatttctgg gatcactaac gtcatagttg    9720
tgttccagga tgagatcgtc ataggccatt tttacaaagc gcgggcggag ggtgccagac    9780
tgcggtataa tggttccatc cggcccaggg gcgtagttac cctcacagat ttgcatttcc    9840
cacgctttga gttcagatgg ggggatcatg tctacctgcg gggcgatgaa gaaaacggtt    9900
tccggggtag gggagatcag ctgggaagaa agcaggttcc tgagcagctg cgacttaccg    9960
cagccggtgg gcccgtaaat cacacctatt accgggtgca actggtagtt aagagagctg    10020
cagctgccgt catccctgag caggggggcc acttcgttaa gcatgtccct gactcgcatg    10080 ttttcccctga ccaaatccgc cagaaggcgc tcgccgccca gcgatagcag ttcttgcaag    10140
gaagcaaagt ttttcaacgg tttgagaccg tccgccgtag gcatgctttt gagcgtttga    10200
ccaagcagtt ccaggcggtc ccacagctcg gtcacctgct ctacggcatc tcgatccagc    10260
atatctcctc gtttcgcggg ttggggcgga tttcgctgta cggcagtagt cggtgctcgt    10320
ccagacgggc cagggtcatg tctttccacg ggcgcagggt cctcgtcagc gtagtctggg    10380
tcacggtgaa ggggtgcgct ccgggctgcg cgctggccag ggtgcgcttg aggctggtcc    10440
tgctggtgct gaagcgctgc cggtcttcgc cctgcgcgtc ggccaggtag catttgacca    10500
tggtgtcata gtccagcccc tccgcggcgt ggcccttggc gcgcagcttg cccttggagg    10560
```

```
aggcgccgca cgaggggcag tgcagacttt tgagggcgta gagcttgggc gcgagaaata   10620
ccgattccgg ggagtaggca tccgcgccgc aggccccgca gacggtctcg cattccacga   10680
gccaggtgag ctctggccgt tcggggtcaa aaaccaggtt tcccccatgc tttttgatgc   10740
gtttcttacc tctggtttcc atgagccggt gtccacgctc ggtgacgaaa aggctgtccg   10800
tgtccccgta tacagacttg agaggcctgt cctcgaccga tgcccttgag agccttcaac   10860
ccagtcagct ccttccggtg ggcgcggggc atgactatcg tcgccgcact tatgactgtc   10920
ttctttatca tgcaactcgt aggacaggtg ccggcagcgc tctgggtcat tttcggcgag   10980
gaccgctttc gctggagcgc gacgatgatc ggcctgtcgc ttgcggtatt cggaatcttg   11040
cacgccctcg ctcaagcctt cgtcactggt cccgccacca aacgtttcgg cgagaagcag   11100
gccattatcg ccggcatggc ggccgacgcg ctgggctacg tcttgctggc gttcgcgacg   11160
cgaggctgga tggccttccc cattatgatt cttctcgctt ccggcggcat cgggatgccc   11220
gcgttgcagg ccatgctgtc caggcaggta gatgacgacc atcagggaca gcttcaaggc   11280
cagcaaaagg ccaggaaccg taaaaaggcc gcgttgctgg cgttttttcca taggctccgc   11340 cccccctgacg agcatcacaa aaatcgacgc tcaagtcaga ggtggcgaaa cccgacagga   11400
ctataaagat accaggcgtt tccccctgga agctccctcg tgcgctctcc tgttccgacc   11460
ctgccgctta ccggatacct gtccgccttt ctcccttcgg gaagcgtggc gctttctcat   11520
agctcacgct gtaggtatct cagttcggtg taggtcgttc gctccaagct gggctgtgtg   11580
cacgaacccc ccgttcagcc cgaccgctgc gccttatccg gtaactatcg tcttgagtcc   11640
aacccggtaa gacacgactt atcgccactg gcagcagcca ctggtaacag gattagcaga   11700
gcgaggtatg taggcggtgc tacagagttc ttgaagtggt ggcctaacta cggctacact   11760
agaaggacag tatttggtat ctgcgctctg ctgaagccag ttaccttcgg aaaaagagtt   11820
ggtagctctt gatccggcaa acaaaccacc gctggtagcg gtggtttttt tgtttgcaag   11880
cagcagatta cgcgcagaaa aaaaggatct caagaagatc ctttgatctt ttctacgggg   11940
tctgacgctc agtggaacga aaactcacgt taagggattt tggtcatgag attatcaaaa   12000
aggatcttca cctagatcct tttaaattaa aaatgaagtt ttaaatcaat ctaaagtata   12060
tatgagtaaa cttggtctga cagttaccaa tgcttaatca gtgaggcacc tatctcagcg   12120
atctgtctat ttcgttcatc catagttgcc tgactccccg tcgtgtagat aactacgata   12180
cgggagggct taccatctgg ccccagtgct gcaatgatac cgcgagaccc acgctcaccg   12240
gctccagatt tatcagcaat aaaccagcca gccggaaggg ccgagcgcag aagtggtcct   12300
gcaactttat ccgcctccat ccagtctatt aattgttgcc gggaagctag agtaagtagt   12360 tcgcagtta atagtttgcg caacgttgtt gccattgctg caggcatcgt ggtgtcacgc   12420
tcgtcgtttg gtatggcttc attcagctcc ggttcccaac gatcaaggcg agttacatga   12480
tcccccatgt tgtgcaaaaa agcggttagc tccttcggtc ctccgatcgt tgtcagaagt   12540
aagttggccg cagtgttatc actcatggtt atggcagcac tgcataattc tcttactgtc   12600
atgccatccg taagatgctt ttctgtgact ggtgagtact caaccaagtc attctgagaa   12660
tagtgtatgc ggcgaccgag ttgctcttgc ccggcgtcaa cacgggataa taccgcgcca   12720
catagcagaa ctttaaaagt gctcatcatt ggaaaacgtt cttcggggcg aaaactctca   12780
aggatcttac cgctgttgag atccagttcg atgtaaccca ctcgtgcacc caactgatct   12840
tcagcatctt ttactttcac cagcgtttct gggtgagcaa aaacaggaag gcaaaatgcc   12900
```

```
gcaaaaaagg gaataagggc gacacggaaa tgttgaatac tcatactctt cctttttcaa   12960
tattattgaa gcatttatca gggttattgt ctcatgagcg gatacatatt tgaatgtatt   13020
tagaaaaa                                                            13028

<210> SEQ ID NO 6
<211> LENGTH: 12454
<212> TYPE: DNA
<213> ORGANISM: Artificial Sequence
<220> FEATURE:
<223> OTHER INFORMATION: Synthetic promoter

<400> SEQUENCE: 6
taaacaaata gggttccgc gcacatttcc ccgaaaagtg ccacctgacg tactgaggac      60
gccagggttt tcccagtcac gacgttgtaa aacgacggcc agtagcagac aagcccgtca    120
gggcgcgtca gcgggtgttg gccctaggac gaaaggaggt cgtgaaatgg ataaaaaaat    180
acagcgtttt tcatgtacaa ctatactagt tgtagtgcct aaataatgct tttaaaactt    240
aaaaataatc aatgtcctca gcggggtgtc ggggatttag gtgacactat aggctgagcg    300
ccgcacaggc atctagaggc tatggcaggg cctgccgccc cgacgttggc tgcgagccct    360
gggccttcac ccgaacttgg ggggtggggt ggggaaaagg aagaaacgcg ggcgtattgg    420
ccccaatggg gtctcggtgg ggtatcgaca gagtgccagc cctgggaccg aaccccgcgt    480
ttatgaacaa acgacccaac accgtgcgtt ttattctgtc tttttattgc cgtcatagcg    540
cgggttcctt ccggtattgt ctccttccgt gtttcaatcg attcaaaaga actcgtccag    600
cagacggtaa aaagcaatgc gttgagaatc cggtgcagca atgccataca gcaccagaaa    660
gcgatcagcc cattcaccgc ccagttcttc agcaatgtca cggggttgcca gtgcgatgtc    720 ctgatagcga tcagccacgc ccaggcgacc gcagtcgata aagccggaga aacggccgtt    780
ttccaccata atgtttggca gacaagcatc gccgtgggtc acaaccaggt cctcgccatc    840
tggcatacgt gctttcaggc gtgcgaacag ttctgccggt gccagaccct gatgttcctc    900
gtccaggtca tcctgatcaa ccaggccagc ttccatgcga gtgcgtgcgc gctcgatacg    960
gtgtttagct tggtgatcga atgggcaagt agctgggtcc agggtatgca gacggcgcat   1020
agcatcagcc atgatggaaa ccttttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtgcaga ccgtcttgtt caatcatggt   1380
ggcaattggg tgtctgagcg atgtggctcg gctggcgacg caaaagaaga tgcggctgac   1440
tgtcgaacag gaggagcaga gagcgaagcg ggaggctgcg ggctcaatttt gcatgctttc    1500 gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
gtcagccatg gggcggagaa tgggcggaac tgggcggagt taggggcggg atgggcggag   1680 ttagggggcgg gactatggtt gctgactaat tgagatgctt gctttgcata cttctgcctg   1740
ctggggagcc tggggacttt ccacacctgg ttgctgacta attgagatgc ttgctttgca   1800
tacttctgcc tgctggggag cctggggact ttccacaccc taacctcgag gccatcgtgg   1860
cacgccaggg ttttcccagt cacgacgttg taaaacgacg gccagtgctc ttctcccccg   1920
```

```
cgggaggttt tataaatccg actgtctaga ttgttgttaa atcacacaaa aaaccaacac   1980
acagatgtaa tgaaaataaa gatatttat tatcgattca gctgtcgctg gggctctcca    2040
gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg gcgtacacct   2220
tctccctcag cagctccacc tcctgggcgc ttttcaggcc cctcacctcg ggttgaaca    2280 ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccaggggcag gctgctgaag tggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgccctggt cgcttttctg ctccacggcg agttcggcct   2700
ccagaatcct gtccacgggc atctccatat ggccgccgta ctcgtcgatg cccagggcgt   2760
cggtgaacat ctgctcgaac tcgaagtcgg ccatgtccag ggcgccgtag ggggcgctgt   2820
cgtggggggt gaagccgggg ccggggctgt cgccgtcgcc cagcatgtcc aggtcgaagt   2880
cgtccagggc gtcggcgtgg gccatggcca cgtcctcgcc gtccaggtgc agctcgtcgc   2940
ccaggctcac gtcggtgggg ggggccacct tccttttctt cttggggccc atcaattggc   3000 caccccccc cccccccccg catgctgtgc cacctgtctt cattcttaac ctgaagattt    3060
agtcttttag ggtttctttt gcacttgggg tacttaacat gccactatgc atattgtaga   3120
tttatagata cttttcaact gatactgctc ccacaggcaa acatgcctgg tgaaacactt   3180
gtttcttttt ggcaaacaag aaatgtttgc ataaaagact cgtgtctgga aaaatgtctt   3240
gagaaattga tatgctactc taagccccaa atctcctttt cacttacctt cccctgctg    3300 caggatgaca atccatgggc ctgtgctttc tgatagtgaa agagaagaaa actcataaat   3360
atagtgtcta ccatgagtca ggcactaact atgcatttat ctctttctgc tttaccctat   3420
aaatggttat taccattaaa agtcatgtga ggaaacagaa ttagggagtt caaactgagc   3480
caggatttca gttcaagttt tccagatcct cgagtaggcg agaccaatgg gtgcgccatg   3540
ggctcttcca aaaatttagg tgacactata gggcaccgct cgcacctgcg cacaggcccg   3600
cggctacaaa ctacgaacga tcattctaga taccacattt gtagaggttt tacttgcttt   3660
aaaaaacctc ccacatctcc ccctgaacct gaaacataaa atgaatgcaa atgttttatt   3720
aacttgttta ttgcagctta taatggttac aaattaagca atagcatcac aaatttcaca   3780
aattaagcat tttttcact gcattctagt tgtggtttgt ccaaactcat caatgtatct    3840
tatcatgtct aatcgattca caggttggtg gggctctcca ggatgggggg gggctgggtg   3900
tggctcatgt cggccacgtc ccaaatctcc tccaggaagg ggggcagctt cctgttcttc   3960
agcttcaggc tgatacacat attgctgttc tgcattccca gggtcctcag ctcgctcagg   4020
atgctcagga tcttgccgta gatcacgctg ctcctggcgc tgccgctcag ctggttcagg   4080
atgtagatcc tcagggtgtt caggtagtac ctctggatct cctccaccag ctggggctgc   4140
tccaggccgg gcctgtcgct gaagatcacc acggcggtca gcagggcgta gtggatgttg   4200
tccagggcca tgctgtacat acatctgcag aagtgcagga ggtcctcgat cacctcggcc   4260
```

```
atgccagcct tcctgtagtt gtccctggtg taagcctggt tgttggcgaa caggatgctg    4320
tcgctggcgg cgtcgtacct cctggccacc ctcagcatca tcacctcgct gctgcaagcc    4380
ttcagcaggg tgatctggtc gggctggctg atcttggcga atccgggcag gcccttggcg    4440
aactccacga tcagctgcac ggtcaggatg gtcatctcgg tgatctgcct gaaggggtg    4500 tcgctctcct cgttctcgtc gtcggcctgc tgccaggtct gggtgatcct tttcaggtcc    4560
tcgtcgctgg gctgctcgta gccgtcctga taccagatca gcctggcgat caggaactgc    4620
tggttggcgg tcagctgggg gatgttcttc tgcctgttgg tcaccagcag cttgtcgctc    4680
aggaacctgg gcacgacctc gtgaatcctg gcggcctcgg ggggggggg ctcgcactgc    4740 atgatggggg gcatgtggtc atcgacggtg gtggtgctca cgggcagctt gtccttctcc    4800
ttctgggcct tcttctcctt ccttttcatg gcgcactggg tctcgggcac cacgcactcg    4860
ggcctcccga gtttcccggg atcgctcacg gtcagctgcc tctggcccct gttgctgctc    4920
tcctcgctgc tgctggtggc gctgatcctg tgctgcctca gggtcagggg catgtcggtc    4980
tccacgctgg ccagcctgtc ggtcacggcg tccttgttca cgttgtcctg cacgaacagg    5040
ccggtcagca gggccttgat gtcttgcagg ctgtccatct tcaggatcat gtccaggtcc    5100
tccctgggga agatcagcag gaacagctgc tccagcctct ccagcctgct ctccacctcg    5160
gtcaggtggg ccctggtcag ggggctcctc ttggtcttgg ggctgtatct gcactcccag    5220
ttgttcttca ggcacttggc gcacttgggc ttctccttgc tgcacttcag cttcttcagc    5280
ctgcagatgt cgcaagcctg ctcgatgctg ctcagcagct tcatggtggc caattgcccc    5340 ccccccccc cgcatgctgc ttccagaccc gcccagagca aaccggatcc tccactttcc    5400
agcctagcct ggggcggggc gaggtctggg gggcgggag tcttggagac tccaaagcgg    5460
gaggcgggga gagggcgggt cccaggccgc gataagggga cagagggaca gcgacctggg    5520
gggtgcagag gtccgggcct ggggagagag acacacagg ggagactcca agggcaagcg    5580
cgagatggga acagaaggag ttgggggcca gtggcgagag ggaacagac tcagaaagga    5640 ggatgccaga cagggagggg acaatttaac ccaaagaggg ggagacaaag acttagggga    5700
cagagaatca gaaggtgggg cagcaggac ccagggatag acagagagag aggggacag    5760 agacccacag agagagggg acagagaccc agggagaggg gacagagacc cagagagagt    5820
gggacagaga cccagagaga gtgggacaga gacccacaga gagaggggga cagagaccca    5880
gggagaggag gacagagacc cagagagggg gggacagaga cccagagagg ggggacagag    5940
gacccaggga ggggggaca gagacccagg gagaggggac agagacccac ggagagggg    6000 acagagaccc agggagaggg gacagagacc cagagagagg gggacagaga cccagagaga    6060
ggggacagag acccagagag acagggaca gagacccaga gagaggggga cagacccca    6120 gagagagggg aacagagacc cagagagaga ggaggacaga gacccagaga gaggggaca    6180 gagacccaga gacagggga cagagacccca gagagagggg gacagagacc cagagagagg    6240
ggaacagaga cccagagaga gaggaggaca gagacccaga gagggggga cagagaccca    6300 gagaggggg acagagacc cagggatggg gggacagaga cccagggaga gggacagag    6360 acccacggag aggggtacag agacccaggg gagggggaca gagacccaga gaggggga    6420 cagagactct gagacagagg gggacagaga ccctgagaga ggggacagag acccagaga    6480 gaggggaaca gagacccaga gagagggg gacagagacc cacagagaga ggggaacaga    6540
gacccagaga gaggggaca gagatccaca gagagagggg gacagagacc cacagagaga    6600
ggggaacaga gacccagaga gaggggaca gagatccaca gagagagggg gacagagacc    6660
```

```
cagggagagg gggacagaga cccagagaga gggggacaga gacccaggga gaggtggaca      6720
gagactctga gacagagggg gacagagact ctgagagaga gtggggacag agacccagag      6780
aggtggatgc cagagatggg gaggagacac cttgactgag gcaaggggca gaggggatg       6840 caaaaaccaa agaattgggg gaagggcagg aactcagaaa ggaggggcca gagatttagg      6900
ggagagagag ggacacagac ttgggggagg actgacacta agataagagt gggacagaag      6960
cccagagtga gagggagagg caatcccatg gaggagggac agggaccctg agagagcaga      7020
tgacagaatt gaagagagag gaggacccgt gaacaggaaa ggagacccta gtgggggcag      7080
tcatgaaggg tgaggagtag gaaatactga cacacagaga caggcaaggc cacttgtctc      7140
ctgccagccc tctgtgatgg ctcgagtggt aatacaatgg ccggttccca tggacctgca      7200
tcgtggtgta actataacgg tcctaaggta gcgaccgcgg agactaggtg tatttatcta      7260
agcgatcgct taattaaggc cggccgccgc aataaaatat ctttattttc attacatctg      7320
tgtgttggtt ttttgtgtga atccatagta ctaacatacg ctctccatca aaacaaaacg      7380
aaacaaaaca aactagcaaa ataggctgtc cccagtgcaa gtccaggtgc cagaacattt      7440
ctctatccat aatgcagggg taccgggtga tgacggtgaa aacctccaat tgcggagtac      7500
tgtcctccga gcggagtact gtcctccgag cggagtactg tcctccgagc ggagtactgt      7560
cctccgagcg gagtactgtc ctccgagcgg agtactgtcc tccgagcgga gagtccccgg      7620
ggacctagag ggtatataat gggtgcctta gctggtgtgt gacctcatct tcctgtacgc      7680
ccctgcaggg gcgcgccacg cgtcgaagaa ggtgagtaat cttaacatgc tcttttttt      7740 ttttttgct aatccctttt gtgtgctgat gttaggatga catttacaac aaatgtttgt       7800
tcctgacagg aaaaaccttg ctgggtacct tcgttgccgg acacttcttg tcctctactt      7860
tggaaaaaag gaattgagag ccgctagcgc caccatggaa gatgccaaaa acattaagaa      7920
gggcccagcg ccattctacc cactcgaaga cgggaccgct ggcgagcagc tgcacaaagc      7980
catgaagcgc tacgccctgg tgcccggcac catcgccttt accgacgcac atatcgaggt      8040
ggacattacc tacgccgagt acttcgagat gagcgttcgg ctggcagaag ctatgaagcg      8100
ctatgggctg aatacaaacc atcggatcgt ggtgtgcagc gagaatagct tgcagttctt      8160
catgcccgtg ttgggtgccc tgttcatcgg tgtggctgtg gccccagcta acgacatcta      8220
caacgagcgc gagctgctga acagcatggg catcagccag cccaccgtcg tattcgtgag      8280
caagaaaggg ctgcaaaaga tcctcaacgt gcaaagaag ctaccgatca tacaaaagat       8340
catcatcatg gatagcaaga ccgactacca gggcttccaa agcatgtaca ccttcgtgac      8400
ttcccatttg ccacccggct tcaacgagta cgacttcgtg cccgagagct tcgaccggga      8460
caaaaccatc gccctgatca tgaacagtag tggcagtacc ggattgccca agggcgtagc      8520
cctaccgcac cgcaccgctt gtgtccgatt cagtcatgcc cgcgacccca tcttcggcaa      8580
ccagatcatc cccgacaccg ctattctcag cgtggtgcca tttcaccacg gcttcggcat      8640
gttcaccacg ctgggctact tgatctgcgg cttccgggtc gtgctcatgt accgcttcga      8700
ggaggagcta ttcttgcgca gcttgcaaga ctataagatt caatctgccc tgctggtgcc      8760
cacactattt agcttcttcg ctaagagcac tctcatcgac aagtacgacc taagcaactt      8820
gcacgagatc gccagcggcg gagcgcctct cagcaaggag gtaggtgagg ccgtggccaa      8880
acgcttccac ctaccaggca tccgccaggg ctacggcctg acagaaacaa ccagcgccat      8940
tctgatcacc cccgaagggg acgacaagcc tggcgcagta ggcaaggtgg tgcccttctt      9000
```

```
cgaggctaag gtggtggact tggacacagg taagaccctg ggtgtgaacc agcgcggcga   9060
gctgtgcgtc cgtggcccca tgatcatgag cggctacgtg aacaaccccg aggctacaaa   9120
cgctctcatc gacaaggacg gctggctgca cagcggcgac atcgcctact gggacgagga   9180
cgagcacttc ttcatcgtgg accggctcaa gagcctgatc aaatacaagg ctaccaggt    9240 agccccagcc gaactggaga gcatcctgct gcaacacccc aacatcttcg acgccgggt    9300 cgctggcctg cccgacgacg atgctggcga gctgcccgcc gcagtcgtcg tgctggaaca   9360
cggtaaaacc atgaccgaga aggagatcgt ggactatgtg gccagccagg ttacaaccgc   9420
caagaagctg cgcggtggtg ttgtgttcgt ggacgaggtg cctaaaggac tgaccggcaa   9480
gttggacgcc cgcaagatcc gcgagattct cattaaggcc aagaagggcg gcaagatcgc   9540
cgtgttaatc gattgcgcaa agctttcgcg ataggcgaga ccaatgggtg tgtacgtagc   9600
ggccgcgtcg acgatagctt gatgggtggc atccctgtga cccctcccca gtgcctctcc   9660
tggccctgga agttgccact ccagtgccca ccagccttgt cctaataaaa ttaagttgca   9720
tcattttgtc tgactaggtg tccttctata atattatggg gtggaggggg gtggtatgga   9780
gcaaggggca agttgggaag acaacctgta gggcctgcgg ggtctattgg gaaccaagct   9840
ggagtgcagt ggcacaatct tggctcactg caatctccgc ctcctgggtt caagcgattc   9900
tcctgcctca gcctcccgag ttgttgggat tccaggcatg catgaccagg ctcagctaat   9960
ttttgttttt ttggtagaga cggggtttca ccatattggc caggctggtc tccaactcct  10020
aatctcaggt gatctaccca ccttggcctc ccaaattgct gggattacag gcgtgaacca  10080
ctgctcccct tccctgtcct tctgatttta aataactata ccagcaggag gacgtccaga  10140
cacagcatag gctacctggc catgcccaac cggtgggaca tttgagttgc ttgcttggca  10200
ctgtcctctc atgcgttggg tccactcagt agatgcctgt tgaattctga tttaaatcgg  10260
tccgcgtacg gcgtggtagg tccgaacgaa tccatggatt accctgttat ccctactcaa  10320
ggacatcatc cctttagtga gggttaattc acgcagtggg tacggaacta aaggcagcac  10380
acatcgtgta atcatggtca tagctgtttc ctgtgtgaaa ttgttatccg ctacgtctct  10440
cccccgcagt aagggctaga ttaactcgtc tcgtgaatat ccggaactcc ctttagtgag  10500
ggttaattgc gttgcgctca ctgcccgctt tccagtcggg aaacctgtcg tgccagctta  10560
atcatggtca tagctgtttc ctgtgtgaaa ttgttatccg ctaccggaaa cgcttccttc  10620
atgtgagcaa aaggccagca aaaggccagg aaccgtaaaa aggccgcgtt gctggcgttt  10680
ttccataggc tccgcccccc tgacgagcat cacaaaaatc gacgctcaag tcagaggtgg  10740
cgaaacccga caggactata agataccagg cgtttccccc tggaagctcc ctcgtgcgc   10800 tctcctgttc cgaccctgcc gcttaccgga tacctgtccg cctttctccc ttcgggaagc   10860
gtggcgcttt ctcatagctc acgctgtagg tatctcagtt cggtgtaggt cgttcgctcc   10920
aagctgggct gtgtgcacga accccccgtt cagcccgacc gctgcgcctt atccggtaac   10980
tatcgtcttg agtccaaccc ggtaagacac gacttatcgc cactggcagc agccactggt   11040
aacaggatta gcagagcgag gtatgtaggc ggtgctacag agttcttgaa gtggtggcct   11100
aactacggct acactagaag aacagtattt ggtatctgcg ctctgctgaa gccagttacc   11160
ttcggaaaaa gagttggtag ctcttgatcc ggcaaacaaa ccaccgctgg tagcggtggt   11220
ttttttgttt gcaagcagca gattacgcgc agaaaaaaag gatctcaaga agatcctttg   11280
atcttttcta cggggtctga cgctcagtgg aacgaaaact cacgttaagg gattttggtc   11340
atgatctatg tcgggtgcgg agaaagaggt aatgaaatgg catacgagta aacttggtct   11400
```

```
gacaccgctg catgagatta tcaaaaagga tcttcaccta gatccttta aattaaaaat    11460 gaagttttaa atcaatctaa agtatatatg agtaaacttg gtctgacagt taccaatgct    11520
taatcagtga ggcacctatc tcagcgatct gtctatttcg ttcatccata gttgcctgac    11580
tccccgtcgt gtagataact acgatacggg agggcttacc atctggcccc agtgctgcaa    11640
tgataccgcg agaccacgc tcaccggctc cagatttatc agcaataaac cagccagccg    11700
gaagcgccga gcgcagaagt ggtcctgcaa ctttatccgc ctccatccag tctattaact    11760
gttgccggga agctagagta agtagttcgc cagttaatag tttgcggagc gttgttgcca    11820
ttgctacagg catcgtggtg tcacgctcgt cgtttggtat ggcttcattc agctccggtt    11880
cccaacgatc aaggcgagtt acatgatccc ccatgttgtg caaaaaagcg gttagctcct    11940
tcggtcctcc gatggttgtc agaagtaagt tggccgcagt gttatcactc atggttatgg    12000
cagcactgca taattctctt actgtcatgc catccgtaag atgcttttct gtgactggtg    12060
agtattcaac caagtcattc tgagaatagt gtatgcggcg accgagttgc tcttgcccgg    12120
cgtcaatacg ggataatacc gcgccacata gcagaacttt aaaagtgctc atcattggga    12180
agcgttcttc ggggcgaaaa ctctcaagga tcttaccgct gttgagatcc agttcgatgt    12240
aacccacacg agcacccaac tgatcttcag catcttttac tttcaccagc gtttctgggt    12300
gagcaaaaac aggaaggcaa aatgccgcaa aaaagggaat aagggcgaca cggaaatgtt    12360
gaatactcat acgcttcctt tttcaatagt attgaagcat ttatcagggt tattgtctcg    12420
ggagcgaata catatttgaa tgtatttaga aaaa                                12454

<210> SEQ ID NO 7
<211> LENGTH: 12579
<212> TYPE: DNA
<213> ORGANISM: Artificial Sequence
<220> FEATURE:
<223> OTHER INFORMATION: Synthetic promoter

<400> SEQUENCE: 7
taaacaaata ggggttccgc gcacatttcc ccgaaaagtg ccacctgacg tctaagaaac        60
cattattatc atgacattaa cctataaaaa taggcgtatc acgaggccct ttcgtcttca       120
agaaaattaa tcgcaccggt atctatgtcg ggtgcggaga agaggtaat gaaatggcag        180 ctagcatcat caataatata ccttattttg gattgaagcc aatatgataa tgaggggtg        240 gagtttgtga cgtggcgcgg ggcgtgggaa cggggcgggt gacgtagtag tgtggcggaa       300
gtgtgatgtt gcaagtgtgg cggaacacat gtaagcgacg gatgtggcaa aagtgacgtt       360
tttggtgtgc gccggtgtac acaggaagtg acaattttcg cgcggtttta ggcggatgtt       420
gtagtaaatt tgggcgtaac cgagtaagat ttggccattt tcgcgggaaa actgaataag       480
aggaagtgaa atctgaataa ttttgtgtta ctcatagcgc gtaatagtgc gccggtgtac       540
acaggaagtg acaattttcg cgcggtttta ggcggatgtt gtagtaaatt tgggcgtaac       600
cgagtaagat ttggccattt tcgcgggaaa actgaataag aggaagtgaa atctgaataa       660
ttttgtgtta ctcattttgt ctagggagat ccggtaccga tatcctagac aacgatgctg       720
agctaactat aacggtccta aggtagcgac cgcgagagact aggtgtattt atctaagcga       780
tcgcttaatt aaggccggcc gccgcaataa aatatcttta ttttcattac atctgtgtgt       840
tggttttttg tgtgaatcca tagtactaac atacgctctc catcaaaaca aaacgaaaca       900
aaacaaacta gcaaaatagg ctgtccccag tgcaagtcca ggtgccagaa catttctcta       960
```

```
tccataatgc agggtaccg ggtgatgacg gtgaaaacct ccaattgcgg agtactgtcc      1020
tccgagcgga gtactgtcct ccgagcggag tactgtcctc cgagcggagt actgtcctcc     1080
gagcggagta ctgtcctccg agcggagtac tgtcctccga gcggagagtc cccggggacc    1140
tagagggtat ataatgggtg ccttagctgg tgtgtgacct catcttcctg tacgccctg      1200 caggggcgcg ccacgcgtcg aagaaggtga gtaatcttaa catgctcttt ttttttttt     1260 ttgctaatcc cttttgtgtg ctgatgttag gatgacattt acaacaaatg tttgttcctg   1320
acaggaaaaa ccttgctggg taccttcgtt gccggacact tcttgtcctc tactttggaa   1380
aaaaggaatt gagagccgct agcgccacca tgattagccc tttcctcgtg ctcgccattg   1440
gcacatgcct caccaatagc ctcgtgcctg agaaagagaa agacggaggc ggaggctccg   1500
gcggaggcgg aagcggaggc ggaggctccg agtccctgaa actgaggaga agggtgcatg   1560
agacagacaa aaactgtaga tccggcacac cccctcagac cggcctggag aaacccacag   1620
gcacaggcca agaaaaacag ggagccggag cccctaccgc tcccggaccc ggaggctccc   1680
ccggaggcta aatcgattgc gcaaagcttt cgcgataggc gagaccaatg ggtgtgtacg   1740
tagcggccgc gtcgacgata gcttgatggg tggcatccct gtgacccctc cccagtgcct   1800
ctcctggccc tggaagttgc cactccagtg cccaccagcc ttgtcctaat aaaattaagt   1860
tgcatcattt tgtctgacta ggtgtccttc tataatatta tggggtggag gggggtggta   1920
tggagcaagg ggcaagttgg gaagacaacc tgtagggcct gcggggtcta ttgggaacca   1980
agctggagtg cagtggcaca atcttggctc actgcaatct ccgcctcctg ggttcaagcg   2040
attctcctgc ctcagcctcc cgagttgttg ggattccagg catgcatgac caggctcagc   2100 taattttgt ttttttggta gagacggggt ttcaccatat tggccaggct ggtctccaac   2160
tcctaatctc aggtgatcta cccaccttgg cctcccaaat tgctgggatt acaggcgtga   2220
accactgctc ccttccctgt ccttctgatt ttaaaataac tataccagca ggaggacgtc   2280
cagacacagc ataggctacc tggccatgcc caaccggtgg gacatttgag ttgcttgctt   2340
ggcactgtcc tctcatgcgt tgggtccact cagtagatgc ctgttgaatt ctgatttaaa   2400
tcggtccgcg tacggcgtgg taggtccgaa cgaatccatg gattaccctg ttatccctat   2460
ccggagttaa cctcgaggac ttcggaactt ctagaaccag accgttcagt ttaaacgctc   2520
ttctccccct cgagtatgtc ctacttttat aaactttggt tgaactaaat aaaacagcaa   2580
catgtaccca acgttttag actgttttat tcagtaccat aaacattcac taaactatac   2640
agagctaaaa tcatgcaaaa gattgcaaaa caaactgcct tgggaaattt ccagtctaag   2700
ctaaatggac caagtatagg attgaatttt aagaagttgg tgggaagatt ccagctcttg   2760
tactcacagg taaggtccta ggattctatt tgttgaagtg tctgcagacc ctctccctac   2820
agcaggggcg tggagcaaat gtgcattcag gaagtgctta ttagtccccc caaaaccttt   2880
ttcgtgacga cagacggatg gaggcctcag acgactccgg cagtaggacc ctgaaccaaa   2940
tgcctgagct gcgctcgaaa ggctcgtctt gcaggagctg gcgagtggca cgggcttcgg   3000
tggccgggct cggggctcgg ggctcggggc ccggagccgg gggggcggg gggtccgtgc     3060 ccagggcgct ctgtggctcg attcatgtcc ccgccctccc acctgagcac actgggcaga   3120
gagcctgcgg catcgggcca gtcgcgcctc ctcgtccgcc ctgggcgggt cgctgggccc   3180
caggccgctt tctacagctc ctttaataaa atggacagca ggggtcctaa ccagacgtgg   3240
gcatcaagac aaaggaggcg gccagacgcg cttgagggcc tgctcgctag ctcccgcccc   3300
cccattccgc ggtcatccgg ggacagaggc caggccggac tgggtggagt tgggactcat   3360
```

```
acgtctgcgt ccaggaaggc gccgggcgag ccccagctag acgtgacggg cggggccgaa    3420
cacggcagcg gaccagaggc ccgcggcgca ccggcgtggg gcggggcaag cggagccttc    3480
cgggatgccg cgcggcagcc ggcttccggc tgtgggtggt gcgggggaca gcggcggccg    3540
gaagctgact gagccggcct ttggtaacgc cgcctgcact tctggggggcg tcgagcctgg    3600 cggtagaatc ttcccagtag gcggcgcggg agggaaaaga ggattgaggg catgcggggg    3660 ggggggggggg caattggcca ccatgggccc caagaagaaa aggaaggtgg cccccccac    3720 cgacgtgagc ctgggcgacg agctgcacct ggacggcgag gacgtggcca tggcccacgc    3780
cgacgccctg gacgacttcg acctggacat gctgggcgac ggcgacagcc ccggccccgg    3840
cttcaccccc cacgacagcg ccccctacgg cgccctggac atggccgact cgagttcga    3900 gcagatgttc accgacgccc tgggcatcga cgagtacggc ggccatatgg agatgccgt    3960 ggacaggatt ctggaggccg aactcgccgt ggagcagaaa agcgaccagg gcgtggaggg    4020
ccccggcgga accggcggca gcggcagcag ccccaacgac cccgtgacca acatctgcca    4080
ggccgccgac aagcagctgt tcaccctggt ggagtgggcc aagaggattc cccacttcag    4140
cagcctgccc ctggacgacc aggtgatcct gctgagggcc ggatgaaacg agctgctgat    4200
cgccagcttc agccacagga gcatcgacgt gagggacggc atcctgctgg ccaccggcct    4260
gcacgtccat aggaacagcg cccacagcgc cggagtgggc gccatcttcg acagggtgct    4320
gaccgagctg gtgagcaaga tgagggacat gaggatggac aagaccgagc tgggctgcct    4380
gagggccatc atcctgttca accccgaggt gaggggcctg aaaagcgccc aggaggtgga    4440
gctgctgagg gagaaggtgt acgccgccct ggaggagtac accaggacca cccacccga    4500 cgagcccggc agattcgcca agctgctgct gaggctgccc agcctgagga gcatcggcct    4560
gaagtgcctg gagcacctgt tcttcttcag gctgatcggc gacgtgccca tcgacacctt    4620
cctgatggag atgctggaga gccccagcga cagctgagcc ggcaactcgc tgtagtaatt    4680
ccagcgagag gcagagggag cgagcgggcg gcgggctagg gtggaggagc ccggcgagca    4740
gagctgcgct gcgggcgtcc tgggaaggga gatccggagc gaataggggg cttcgcctct    4800
ggcccagccc tcccgctgat ccccccagcca gcggtgcgca cccctagccg catccacgaa    4860
actttgccca tagcagcggg cgggcacttt gcactgaaac ttacaacacc cgagcaagga    4920
cgcgactctc ccgacgcggg gaggctattc tgcccatttg gggacacttc cccgccgctg    4980
ccaggacccg cttctctgaa aggctctcct tgcagctgct tagacgctgg attttttcg    5040 ggtagtggaa aaccagcagc ctcccgcgac cagatctgcc accatgaagc tgctgagcag    5100
catcgagcag gcttgcgaca tctgcaggct gaagaagctg aagtgcagca aggagaagcc    5160
caagtgcgcc aagtgcctga gaacaactg ggagtgcaga tacagcccca agaccaagag    5220
gagccccctg accagggccc acctgaccga ggtggagagc aggctggaga ggctggagca    5280
gctgttcctg ctgatcttcc ccagggagga cctggacatg atcctgaaga tggacagcct    5340
gcaagacatc aaggccctgc tgaccggcct gttcgtgcag gacaacgtga acaaggacgc    5400
cgtgaccgac aggctggcca gcgtggagac cgacatgccc ctgacccctga ggcagcacag    5460 gatcagcgcc accagcagca gcgaggagag cagcaacaag ggcagaggc agctgaccgt    5520 gagccccgag tttccccggga tcaggcccga gtgcgtggtg cccgagaccc agtgcgccat    5580
gaaaaggaag gagaagaagg cccagaagga gaaggacaag ctgccccgtga gcaccaccac    5640 cgtcgatgac cacatgcccc ccatcatgca gtgcgagccc ccccccccg aggccgccag    5700
```

-continued

```
gattcacgag gtcgtgccca ggttcctgag cgacaagctg ctggtgacca acaggcagaa   5760
gaacatcccc cagctgaccg ccaaccagca gttcctgatc gccaggctga tctggtatca   5820
ggacggctac gagcagccca gcgacgagga cctgaaaagg atcacccaga cctggcagca   5880
ggccgacgac gagaacgagg agagcgacac ccccttcagg cagatcaccg agatgaccat   5940
cctgaccgtg cagctgatcg tggagttcgc caagggcctg cccggattcg ccaagatcag   6000
ccagcccgac cagatcaccc tgctgaaggc ttgcagcagc gaggtgatga tgctgagggt   6060
ggccaggagg tacgacgccg ccagcgacag catcctgttc gccaacaacc aggcttacac   6120
cagggacaac tacaggaagg ctggcatggc cgaggtgatc gaggacctcc tgcacttctg   6180
cagatgtatg tacagcatgg ccctggacaa catccactac gccctgctga ccgccgtggt   6240
gatcttcagc acaggcccg gcctggagca gccccagctg gtggaggaga tccagaggta   6300
ctacctgaac accctgagga tctacatcct gaaccagctg agcggcagcg ccaggagcag   6360
cgtgatctac ggcaagatcc tgagcatcct gagcgagctg aggaccctgg aatgcagaa   6420 cagcaatatg tgtatcagcc tgaagctgaa gaacaggaag ctgccccct tcctggagga   6480 gatttgggac gtggccgaca tgagccacac ccagcccccc ccatcctgg agagccccac   6540 caacctgtga atcgattaga catgataaga tacattgatg agtttggaca aaccacaact   6600
agaatgcagt gaaaaaaatg cttaatttgt gaaatttgtg atgctattgc ttaatttgta   6660
accattataa gctgcaataa acaagttaat aaaacatttg cattcatttt atgtttcagg   6720
ttcaggggga gatgtgggag gttttttaaa gcaagtaaaa cctctacaaa tgtggtatct   6780
agagctcttc caaatagatc tggaaggtgc tgaggtacga tgagaccgc accaggtgca   6840 gaccctgcga gtgtggcggt aaacatatta ggaaccagcc tgtgatgctg gatgtgaccg   6900
aggagctgag gcccgatcac ttggtgctgg cctgcacccg cgctgagttt ggctctagcg   6960
atgaagatac agattgaggt actgaaatgt gtgggcgtgg cttaagggtg ggaaagaata   7020
tataaggtgg gggtcttatg tagttttgta tctgtttttgc agcagccgcc gccgccatga   7080
gcaccaactc gtttgatgga agcattgtga gctcatattt gacaacgcgc atgcccccat   7140
gggccggggt gcgtcagaat gtgatgggct ccagcattga tggtcgcccc gtcctgcccg   7200
caaactctac taccttgacc tacgagaccg tgtctggaac gccgttggag actgcagcct   7260
ccgccgccgc ttcagccgct gcagccaccg cccgcgggat tgtgactgac tttgctttcc   7320
tgagcccgct tgcaagcagt gcagcttccc gttcatccgc ccgcgatgac aagttgacgg   7380
ctcttttggc acaattggat tctttgaccc gggaacttaa tgtcgtttct cagcagctgt   7440
tggatctgcg ccagcaggtt tctgccctga aggcttcctc ccctcccaat gcggtttaaa   7500
acataaataa aaaaccagac tctgtttgga tttggatcaa gcaagtgtct tgctgtcttt   7560
atttaggggt tttgcgcgcg cggtaggccc gggaccagcg gtctcggtcg ttgagggtcc   7620 tgtgtattt ttccaggacg tggtaaaggt gactctggat gttcagatac atgggcataa   7680
gcccgtctct ggggtggagg tagcaccact gcagagcttc atgctgcggg gtggtgttgt   7740
agatgatcca gtcgtagcag gagcgctggg cgtggtgcct aaaaatgtct tcagtagca   7800 agctgattgc caggggcagg cccttggtgt aagtgtttac aaagcggtta agctgggatg   7860
ggtgcatacg tggggatatg agatgcatct tggactgtat ttttaggttg gctatgttcc   7920
cagccatatc cctccgggga ttcatgttgt gcagaaccac cagcacagtg tatccggtgc   7980
acttgggaaa tttgtcatgt agcttagaag gaaatgcgtg gaagaacttg agacgccct   8040 tgtgacctcc aagattttcc atgcattcgt ccataatgat ggcaatgggc ccacgggcgg   8100
```

```
cggcctgggc gaagatattt ctgggatcac taacgtcata gttgtgttcc aggatgagat      8160
cgtcataggc cattttttaca aagcgcgggc ggagggtgcc agactgcggt ataatggttc     8220
catccggccc aggggcgtag ttaccctcac agatttgcat ttcccacgct ttgagttcag      8280 atgggggat catgtctacc tgcggggcga tgaagaaaac ggtttccggg gtaggggaga       8340
tcagctggga agaaagcagg ttcctgagca gctgcgactt accgcagccg gtgggcccgt      8400
aaatcacacc tattaccggg tgcaactggt agtaagaga gctgcagctg ccgtcatccc       8460
tgagcagggg ggccacttcg ttaagcatgt ccctgactcg catgttttcc ctgaccaaat      8520
ccgccagaag gcgctcgccg cccagcgata gcagttcttg caaggaagca aagttttca      8580 acggtttgag accgtccgcc gtaggcatgc ttttgagcgt ttgaccaagc agttccaggc     8640
ggtcccacag ctcggtcacc tgctctacgg catctcgatc cagcatatct cctcgtttcg     8700
cgggttgggg cggctttcgc tgtacggcag tagtcggtgc tcgtccagac gggccagggt     8760
catgtctttc cacgggcgca gggtcctcgt cagcgtagtc tgggtcacgg tgaaggggtg     8820
cgctccgggc tgcgcgctgg ccagggtgcg cttgaggctg gtcctgctgg tgctgaagcg     8880
ctgccggtct tcgccctgcg cgtcggccag gtagcatttg accatggtgt catagtccag     8940
cccctccgcg gcgtggccct tggcgcgcag cttgcccttg gaggaggcgc cgcacgaggg     9000
gcagtgcaga cttttgaggg cgtagagctt gggcgcgaga aataccgatt ccggggagta    9060
ggcatccgcg ccgcaggccc cgcagacggt ctcgcattcc acgagccagg tgagctctgg    9120
ccgttcgggg tcaaaaacca ggtttccccc atgcttttg atgcgtttct tacctctggt     9180
ttccatgagc cggtgtccac gctcggtgac gaaaaggctg tccgtgtccc cgtatacaga    9240
cttgagaggc ctgtcctcga ccgatgccct tgagagcctt caacccagtc agctccttcc    9300
ggtgggcgcg gggcatgact atcgtcgccg cacttatgac tgtcttcttt atcatgcaac    9360
tcgtaggaca ggtgccggca gcgctctggg tcattttcgg cgaggaccgc tttcgctgga    9420
gcgcgacgat gatcggcctg tcgcttgcgg tattcggaat cttgcacgcc ctcgctcaag    9480
ccttcgtcac tggtcccgcc accaaacgtt tcggcgagaa gcaggccatt atcgccggca    9540
tggcggccga cgcgctgggc tacgtcttgc tggcgttcgc gacgcgaggc tggatggcct    9600
tccccattat gattcttctc gcttccggcg gcatcgggat gcccgcgttg caggccatgc    9660
tgtccaggca ggtagatgac gaccatcagg gacagcttca aggccagcaa aaggccagga    9720
accgtaaaaa ggccgcgttg ctggcgtttt tccataggct ccgccccct gacgagcatc     9780 acaaaaatcg acgctcaagt cagaggtggc gaaacccgac aggactataa agataccagg    9840
cgtttccccc tggaagctcc ctcgtgcgct ctcctgttcc gaccctgccg cttaccggat    9900
acctgtccgc ctttctccct tcgggaagcg tggcgctttc tcatagctca cgctgtaggt    9960
atctcagttc ggtgtaggtc gttcgctcca agctgggctg tgtgcacgaa ccccccgttc   10020
agcccgaccg ctgcgcctta tccggtaact atcgtcttga gtccaacccg gtaagacacg   10080
acttatcgcc actggcagca gccactggta acaggattag cagagcgagg tatgtaggcg   10140
gtgctacaga gttcttgaag tggtggccta actacggcta cactagaagg acagtatttg   10200
gtatctgcgc tctgctgaag ccagttacct tcggaaaaag agttggtagc tcttgatccg   10260
gcaaacaaac caccgctggt agcggtggtt ttttgtttg caagcagcag attacgcgca    10320
gaaaaaaagg atctcaagaa gatcctttga tcttttctac ggggtctgac gctcagtgga   10380
acgaaaactc acgttaaggg attttggtca tgagattatc aaaaaggatc ttcacctaga   10440
```

| | | | | | |
|---|---|---|---|---|---|
| tcctttttaaa | ttaaaaatga | agttttaaat | caatctaaag | tatatatgag | taaacttggt | 10500 |
| ctgacagctc | gagtatgtcc | tacttttata | aactttggtt | gaactaaata | aaacagcaac | 10560 |
| atgtacccaa | cgtttttaga | ctgttttatt | cagtaccata | aacattcact | aaactataca | 10620 |
| gagctaaaat | catgcaaaag | attgcaaaac | aaactgcctt | gggaaatttc | cagtctaagc | 10680 |
| taaatggacc | aagtatagga | ttgaatttta | agaagttggt | gggaagattc | cagctcttgt | 10740 |
| actcacaggt | aaggtcctag | gattctattt | gttgaagtgt | ctgcagaccc | tctccctaca | 10800 |
| gcagggcgt | ggagcaaatg | tgcattcagg | aagtgcttat | tagtccccc | aaaaccttt | 10860 |
| tcgtgacgac | agacggatgg | aggcctcaga | cgactccggc | agtaggaccc | tgaaccaaat | 10920 |
| gcctgagctg | cgctcgaaag | gctcgtcttg | caggagctgg | cgagtggcac | gggcttcggt | 10980 |
| ggccgggctc | ggggctcggg | gctcggggcc | cggagccggg | ggggcgggg | ggtccgtgcc | 11040 |
| cagggcgctc | tgtggctcga | ttcatgtccc | cgccctccca | cctgagcaca | ctgggcagag | 11100 |
| agcctgcggc | atcgggccag | tcgcgcctcc | tcgtccgccc | tgggcgggtc | gctgggcccc | 11160 |
| aggccgctt | ctacagctcc | tttaataaaa | tggacagcag | gggtcctaac | cagacgtggg | 11220 |
| catcaagaca | aaggaggcgg | ccagacgcgc | ttgagggcct | gctcgctagc | tcccgccccc | 11280 |
| ccattccgcg | gtcatccggg | gacagaggcc | aggccggact | gggtggagtt | gggactcata | 11340 |
| cgtctgcgtc | caggaaggcg | ccgggcgagc | cccagctaga | cgtgacgggc | ggggccgaac | 11400 |
| acggcagcgg | accagaggcc | cgcggcgcac | cggcgtgggg | cggggcaagc | ggagccttcc | 11460 |
| gggatgccgc | gcggcagccg | gcttccggct | gtgggtggtg | cggggacag | cggcggccgg | 11520 |
| aagctgactg | agccggcctt | tggtaacgcc | gcctgcactt | ctgggggcgt | cgagcctggc | 11580 |
| ggtagaatct | tcccagtagg | cggcgcggga | gggaaaagag | gattgagggc | atgcttacca | 11640 |
| atgcttaatc | agtgaggcac | ctatctcagc | gatctgtcta | tttcgttcat | ccatagttgc | 11700 |
| ctgactcccc | gtcgtgtaga | taactacgat | acgggagggc | ttaccatctg | gccccagtgc | 11760 |
| tgcaatgata | ccgcgagacc | cacgctcacc | ggctccagat | ttatcagcaa | taaaccagcc | 11820 |
| agccggaagg | gccgagcgca | gaagtggtcc | tgcaacttta | tccgcctcca | tccagtctat | 11880 |
| taattgttgc | cgggaagcta | gagtaagtag | ttcgccagtt | aatagtttgc | gcaacgttgt | 11940 |
| tgccattgct | gcaggcatcg | tggtgtcacg | ctcgtcgttt | ggtatggctt | cattcagctc | 12000 |
| cggttcccaa | cgatcaaggc | gagttacatg | atccccatg | ttgtgcaaaa | aagcggttag | 12060 |
| ctccttcggt | cctccgatcg | ttgtcagaag | taagttggcc | gcagtgttat | cactcatggt | 12120 |
| tatggcagca | ctgcataatt | ctcttactgt | catgccatcc | gtaagatgct | tttctgtgac | 12180 |
| tggtgagtac | tcaaccaagt | cattctgaga | atagtgtatg | cggcgaccga | gttgctcttg | 12240 |
| cccggcgtca | acacgggata | ataccgcgcc | acatagcaga | actttaaaag | tgctcatcat | 12300 |
| tggaaaacgt | tcttcggggc | gaaaactctc | aaggatctta | ccgctgttga | gatccagttc | 12360 |
| gatgtaaccc | actcgtgcac | ccaactgatc | ttcagcatct | tttactttca | ccagcgtttc | 12420 |
| tgggtgagca | aaaacaggaa | ggcaaaatgc | cgcaaaaaag | ggaataaggg | cgacacggaa | 12480 |
| atgttgaata | ctcatactct | tcctttttca | atattattga | agcatttatc | agggttattg | 12540 |
| tctcatgagc | ggatacatat | ttgaatgtat | ttagaaaaa | | | 12579 |

<210> SEQ ID NO 8
<211> LENGTH: 11443
<212> TYPE: DNA
<213> ORGANISM: Artificial Sequence
<220> FEATURE:
<223> OTHER INFORMATION: Synthetic promoter

<400> SEQUENCE: 8

```
taaacaaata ggggttccgc gcacatttcc ccgaaaagtg ccacctgacg tactgaggac    60
gccagggttt tcccagtcac gacgttgtaa aacgacggcc agtagcagac aagcccgtca   120
gggcgcgtca gcgggtgttg gccctaggac gaaaggaggt cgtgaaatgg ataaaaaaat   180
acagcgtttt tcatgtacaa ctatactagt tgtagtgcct aaataatgct tttaaaactt   240
aaaaataatc aatgtcctca gcggggtgtc ggggatttag gtgacactat aggctgagcg   300
ccgcacaggc atctagaggc tatggcaggg cctgccgccc cgacgttggc tgcgagccct   360
gggccttcac ccgaacttgg ggggtggggt ggggaaaagg aagaaacgcg ggcgtattgg   420
ccccaatggg gtctcggtgg ggtatcgaca gagtgccagc cctgggaccg aaccccgcgt   480
ttatgaacaa acgacccaac accgtgcgtt ttattctgtc tttttattgc cgtcatagcg   540
cgggttcctt ccggtattgt ctccttccgt gtttcaatcg attcaaaaga actcgtccag   600
cagacggtaa aaagcaatgc gttgagaatc cggtgcagca atgccataca gcaccagaaa   660
gcgatcagcc cattcaccgc ccagttcttc agcaatgtca cgggttgcca gtgcgatgtc   720
ctgatagcga tcagccacgc ccaggcgacc gcagtcgata aagccggaga acggccgtt   780
ttccaccata atgtttggca gacaagcatc gccgtgggtc acaaccaggt cctcgccatc   840
tggcatacgt gctttcaggc gtgcgaacag ttctgccggt gccagaccct gatgttcctc   900
gtccaggtca tcctgatcaa ccaggccagc ttccatgcga gtgcgtgcgc gctcgatacg   960
gtgtttagct tggtgatcga atgggcaagt agctgggtcc agggtatgca gacggcgcat  1020
agcatcagcc atgatggaaa ccttttctgc cggtgccaga tgagaggaca gcagatcctg  1080
gcctggaacc tcgcccagca gcagccagtc gcggccagcc tcggtcacaa catccagcac  1140
agctgcgcat ggaacgccgg tagtagccag ccaggacaga cgagctgctt catcttgcag  1200
ttcgttcagt gcgccggaca gatcggtctt aacaaacagc accggacggc cttgagcgga  1260
cagacggaac acagctgcgt cggagcaacc gatagtctgt tgagcccagt catagccaaa  1320
cagacgttcc acccaagcag ccggagaacc agcgtgcaga ccgtcttgtt caatcatggt  1380
ggcaattggg tgtctgagcg atgtggctcg gctggcgacg caaaagaaga tgcggctgac  1440
tgtcgaacag gaggagcaga gagcgaagcg ggaggctgcg ggctcaattt gcatgcttta  1500
gttcctcacc ttgtcgtatt atactatgcc gatatactat gccgatgatt aattgtcaac  1560
gtatacggaa tagctctgag gccgaggcag cttcggcctc tgcataaata aaaaaaatta  1620
gtcagccatg gggcggagaa tgggcggaac tgggcggagt taggggcggg atgggcggag  1680
ttaggggcgg gactatggtt gctgactaat tgagatgctt gctttgcata cttctgcctg  1740
ctggggagcc tggggacttt ccacacctgg ttgctgacta attgagatgc ttgctttgca  1800
tacttctgcc tgctggggag cctggggact tccacaccc taacctcgag gccatcgtgg  1860
cacgccaggg ttttcccagt cacgacgttg taaaacgacg ccagtgctc ttctcccccg   1920
cgggaggttt tataaatccg actgtctaga ttgttgttaa atcacacaaa aaaccaacac  1980
acagatgtaa tgaaaataaa gatattttat tatcgattca gctgtcgctg gggctctcca  2040
gcatctccat caggaaggtg tcgatgggca cgtcgccgat cagcctgaag aagaacaggt  2100
gctccaggca cttcaggccg atgctcctca ggctgggcag cctcagcagc agcttggcga  2160
atctgccggg ctcgtcgggg tgggtggtcc tggtgtactc ctccagggcg cgtacacct   2220
tctccctcag cagctccacc tcctgggcgc ttttcaggcc cctcacctcg gggttgaaca  2280
```

```
ggatgatggc cctcaggcag cccagctcgg tcttgtccat cctcatgtcc ctcatcttgc    2340
tcaccagctc ggtcagcacc ctgtcgaaga tggcgcccac tccggcgctg tgggcgctgt    2400
tcctatggac gtgcaggccg gtggccagca ggatgccgtc cctcacgtcg atgctcctgt    2460
ggctgaagct ggcgatcagc agctcgttcc atccggccct cagcaggatc acctggtcgt    2520 ccagggcag gctgctgaag tggggaatcc tcttggccca ctccaccagg gtgaacagct     2580
gcttgtcggc ggcctggcag atgttggtca cggggtcgtt ggggctgctg ccgctgccgc    2640
cggttccgcc ggggccctcc acgccctggt cgcttttctg ctccacggcg agttcggcct    2700
ccagaatcct gtccacgggc atctccatat ggccgccgta ctcgtcgatg cccagggcgt    2760
cggtgaacat ctgctcgaac tcgaagtcgg ccatgtccag ggcgccgtag ggggcgctgt    2820
cgtggggggt gaagccgggg ccggggctgt cgccgtcgcc cagcatgtcc aggtcgaagt    2880
cgtccagggc gtcggcgtgg gccatggcca cgtcctcgcc gtccaggtgc agctcgtcgc    2940
ccaggctcac gtcggtgggg ggggccacct tccttttctt cttggggccc atcaattggc    3000
cacccccccc ccccccccg catgcccggc gggtcaggga cgcgggcgcg cggtgcgctg     3060
ggggcggcac gtccgggcgg aggaggcgtc atcccgtggc cccaggagcg gcaatcagcc    3120
gagactgagc cagcgcccgg ccgcaggcag acccaagcgc caggaggcgg agccagcgct    3180
gaccccaccc cgcccctccc cccgcccctc gcagccttt tctcacctcac tggctttcct    3240 gagcgagagc ggaactgctg ggggaacctt cgccaccctc tcccggacaa ctctacgggg    3300
aaagcccagc tgcggacaag ccagacttgt ggtcttctgc caggggcggc aggccctatc    3360
ccctctctgg gcctcagttc cactcccgc accccgtaaa aagattggcg tagaagtcgt     3420
ggaggacctc tctccaaggg cgcagaggag tccaacaccc aacaaccttg ctatggccag    3480
ctaagtggtt cgcaccctga ggactatggt cctcggagga tgcgttcgcc taagtggaca    3540
cggctccctg ccgagcctac cagcaggcac aacgatgata tgtggggagc actcagggac    3600
ccgctgttgc tttgcctggg agaacactgg aaattttca tcttggcctg gctccttccc     3660
ctccctctcc tttctcctcc ctttcccagc cagcagcttt ctgggctgcc tcccccaag     3720 ccagctggtg tacgctcaga aaatccaaac tcatttccat gtgagtggag ggggatataa    3780
ttaggaaggc cccttcccca agtagagagg ggagcatccc ccgtgcccca ctcactgtgg    3840
gggagggagg gtcaaagcag cttaaggga tctctgcccg caaagtgcct agggctcaac     3900
tatctcaggc aacctgacca ttcagtgggg actcccttgg ggggtccagg cccagaccct    3960
ctgcagttac ctgagcagtc cagccagctc tgccatcagc tcctcctctc agaactacgt    4020
gcctgccctt tgtaaaaggg tctcctctct ctaaaccaga cagggcccag acctaccact    4080
tccacttgtg ccccagggaa ccatgaatgg aaaatccacc cagctcagta agtacttatc    4140
tagtgtttac tggatgtcta gctgcactga gaggagacag gccgaggaag gagtagaggt    4200
gaacatccaa ccttcagaac tcacagacct agacacgatt cacgcactgc agacaccagc    4260
aaaggcggtg ggctggctgc cctctgccct ctgccctgct ccatggggcc aggaccattt    4320
ggttgttgtt tttacctcct ggaaccagga aagttttgct accaagaagt ttggctttac    4380
cattctacat tttgcttcca gttgtcccct ccttcttccc tcagagtcct gaggcacccc    4440
agcaggccag gaaggtaaac tcaaggcacc tccagagaca gtgcagagtg aggttcctgg    4500
cccactggga gaagccaaca gccctcgagt aggcgagacc aatgggtgcg ccatgggctc    4560
ttccaaaaat ttaggtgaca ctatagggca ccgctcgcac ctgcgcacag gcccgcggct    4620
acaaactacg aacgatcatt ctagatacca catttgtaga ggttttactt gctttaaaaa    4680
```

```
acctcccaca tctcccccctg aacctgaaac ataaaatgaa tgcaaatgtt ttattaactt    4740
gtttattgca gcttataatg gttacaaatt aagcaatagc atcacaaatt tcacaaatta    4800 agcattttt  tcactgcatt ctagttgtgg tttgtccaaa ctcatcaatg tatcttatca    4860
tgtctaatcg attcacaggt tggtggggct ctccaggatg ggggggggct gggtgtggct    4920
catgtcggcc acgtcccaaa tctcctccag gaaggggggc agcttcctgt tcttcagctt    4980
caggctgata cacatattgc tgttctgcat tcccagggtc ctcagctcgc tcaggatgct    5040
caggatcttg ccgtagatca cgctgctcct ggcgctgccg ctcagctggt tcaggatgta    5100
gatcctcagg gtgttcaggt agtacctctg gatctcctcc accagctggg gctgctccag    5160
gccgggcctg tcgctgaaga tcaccacggc ggtcagcagg gcgtagtgga tgttgtccag    5220
ggccatgctg tacatacatc tgcagaagtg caggaggtcc tcgatcacct cggccatgcc    5280
agccttcctg tagttgtccc tggtgtaagc ctggttgttg gcgaacagga tgctgtcgct    5340
ggcggcgtcg tacctcctgg ccaccctcag catcatcacc tcgctgctgc aagccttcag    5400
cagggtgatc tggtcgggct ggctgatctt ggcgaatccg ggcaggccct tggcgaactc    5460
cacgatcagc tgcacggtca ggatggtcat ctcggtgatc tgcctgaagg gggtgtcgct    5520
ctcctcgttc tcgtcgtcgg cctgctgcca ggtctgggtg atccttttca ggtcctcgtc    5580
gctgggctgc tcgtagccgt cctgatacca gatcagcctg gcgatcagga actgctggtt    5640
ggcggtcagc tgggggatgt tcttctgcct gttggtcacc agcagcttgt cgctcaggaa    5700
cctgggcacg acctcgtgaa tcctggcggc ctcgggggg  ggggctcgc  actgcatgat    5760 ggggggcatg tggtcatcga cggtggtggt gctcacgggc agcttgtcct tctccttctg    5820
ggccttcttc tccttccttt tcatggcgca ctgggtctcg gcaccacgc  actcgggcct    5880 cccgagtttc ccgggatcgc tcacggtcag ctgcctctgg cccttgttgc tgctctcctc    5940
gctgctgctg gtggcgctga tcctgtgctg cctcagggtc aggggcatgt cggtctccac    6000
gctggccagc ctgtcggtca cggcgtcctt gttcacgttg tcctgcacga acaggccggt    6060
cagcagggcc ttgatgtctt gcaggctgtc catcttcagg atcatgtcca ggtcctccct    6120
ggggaagatc agcaggaaca gctgctccag cctctccagc ctgctctcca cctcggtcag    6180
gtgggccctg gtcagggggc tcctcttggt cttgggctg  tatctgcact cccagttgtt    6240
cttcaggcac ttgcgcact  tgggcttctc cttgctgcac ttcagcttct tcagcctgca    6300
gatgtcgcaa gcctgctcga tgctgctcag cagcttcatg gtggccaatt gcccccccc     6360 cccccgcat  gccttgcact ccaatcagaa ccagcaagat gatgcccaag aggaaaagaa    6420
caccactttt cttcatagtg atagaatgga gttccaagtc actcctgtat tggattttga    6480
gcctgagaaa ttcttagag  aacacatttt ggggatcata tttatttagg atattcattt    6540
ctctcctaaa ctctgattgg ctagtatctt tagccgagct aactaaattg accacaaact    6600
tgattgtgct gggggaaacc ctagtctcag atccaaggga atttctgcat gttttattt     6660 ccatttcaca taaatgggtg gtttatagta agggatgtga aactagcaac actgatagcc    6720
tttggcacat tcacagttgc tcacctgtgt gaagaatagg ttatataatg aatatactaa    6780
tgttatacaa caaaggttgg agatgtggtt tccagatggg aaatattaaa gtccagataa    6840
ataatatact tttcaaattc ccttactatt tatggcatat tcttctgtat aatagatggc    6900
tacattgata tttcttata  ttgcccactt aacaacttaa agcaccttaa ttcctctgg     6960 gaccaggtca tttctacta  gtggtaagct cattctgtat cattcctgct acagtattat    7020
```

```
tttttaaact aataaattgg ttagaataag gggtcagttg catgtaagag acccaaatta   7080
acagtggcta agaaatgcaa taaaaatgaa gataaatagc tgggacctaa ttaaagagct   7140
tttgcacagc aaaaggaaca gtcagcagag taaacagaca acccacagag cgggagaaaa   7200
tcttcacaat ctatatacct gacaaaggac taatatccag aatccagaat gaattcaaac   7260
aaatcattaa gtaaaaaaca aacaatccca ttaaaaagtg ggctaaggac atcaatatac   7320
aattctcaaa agaagataca cgaatagcca acaaacatat gaaaaaatgc tcatcactaa   7380
tgatcaggga aatgcaaatc aaaaccacgg tgcgatacca ccttacaccc gcaagaatgg   7440
ccataatcaa aaaatcaaaa aacagcagat gttggtgtgg actcgagtgg taatacaatg   7500
gccggttccc atggacctgc atcgtggtgt aactataacg gtcctaaggt agcgaccgcg   7560
gagactaggt gtatttatct aagcgatcgc ttaattaagg ccggccgccg caataaaata   7620
tctttatttt cattacatct gtgtgttggt tttttgtgtg aatccatagt actaacatac   7680
gctctccatc aaaacaaaac gaaacaaaac aaactagcaa aataggctgt ccccagtgca   7740
agtccaggtg ccagaacatt tctctatcca taatgcaggg gtaccgggtg atgacggtga   7800
aaacctccaa ttgcggagta ctgtcctccg agcggagtac tgtcctccga gcggagtact   7860
gtcctccgag cggagtactg tcctccgagc ggagtactgt cctccgagcg gagtactgtc   7920
ctccgagcgg agagtccccg gggacctaga gggtatataa tgggtgcctt agctggtgtg   7980
tgacctcatc ttcctgtacg cccctgcagg ggcgcgccac gcgtcgaaga aggtgagtaa   8040
tcttaacatg ctcttttttt tttttttttgc taatcccttt tgtgtgctga tgttaggatg   8100
acatttacaa caaatgtttg ttcctgacag gaaaaacctt gctgggtacc ttcgttgccg   8160
gacacttctt gtcctctact ttggaaaaaa ggaattgaga gccgctagcg ccaccatgat   8220
tagcccttc ctcgtgctcg ccattggcac atgcctcacc aatagcctcg tgcctggcgg   8280
aggcggaagc ggaggcggag gctccggcgg aggcggaagc tgtcagcctg tgacacagga   8340
ggacggaaag gaaagcagga tctccgtgca agagaggcag cctgccccta cccctagcaa   8400
tggctccccc aaagacggac ccgaaatccc tcccacaggc ggaaaggcta aggccaagcc   8460
cgtgacaaga ggagccggag ccaggagcgg aaccctccc caaaccggac tggaaaagcc   8520
taccggaacc ggatgaatcg attgcgcaaa gctttcgcga taggcgagac caatgggtgt   8580
gtacgtagcg gccgcgtcga cgatagcttg atgggtggca tccctgtgac ccctccccag   8640
tgcctctcct ggccctggaa gttgccactc cagtgcccac cagccttgtc ctaataaaat   8700
taagttgcat cattttgtct gactaggtgt ccttctataa tattatgggg tggaggggggg   8760
tggtatggag caaggggcaa gttgggaaga caacctgtag ggcctgcggg gtctattggg   8820
aaccaagctg gagtgcagtg gcacaatctt ggctcactgc aatctccgcc tcctgggttc   8880
aagcgattct cctgcctcag cctcccgagt tgttgggatt ccaggcatgc atgaccaggc   8940
tcagctaatt tttgtttttt tggtagagac ggggtttcac catattggcc aggctggtct   9000
ccaactccta atctcaggtg atctacccac cttggcctcc caaattgctg ggattacagg   9060
cgtgaaccac tgctcccttc cctgtccttc tgattttaaa ataactatac cagcaggagg   9120
acgtccagac acagcatagg ctacctggcc atgcccaacc ggtgggacat ttgagttgct   9180
tgcttggcac tgtcctctca tgcgttgggt ccactcagta gatgcctgtt gaattctgat   9240
ttaaatcggt ccgcgtacgg cgtggtaggt ccgaacgaat ccatggatta ccctgttatc   9300
cctactcaag gacatcatcc ctttagtgag ggttaattca cgcagtgggt acggaactaa   9360
aggcagcaca catcgtgtaa tcatggtcat agctgttttcc tgtgtgaaat tgttatccgc   9420
```

```
tacgtctctc ccccgcagta agggctagat taactcgtct cgtgaatatc cggaactccc   9480
tttagtgagg gttaattgcg ttgcgctcac tgcccgcttt ccagtcggga aacctgtcgt   9540
gccagcttaa tcatggtcat agctgtttcc tgtgtgaaat tgttatccgc taccggaaac   9600
gcttccttca tgtgagcaaa aggccagcaa aaggccagga accgtaaaaa ggccgcgttg   9660
ctggcgtttt tccataggct ccgcccccct gacgagcatc acaaaaatcg acgctcaagt   9720
cagaggtggc gaaacccgac aggactataa agataccagg cgtttccccc tggaagctcc   9780
ctcgtgcgct ctcctgttcc gaccctgccg cttaccggat acctgtccgc ctttctccct   9840
tcgggaagcg tggcgctttc tcatagctca cgctgtaggt atctcagttc ggtgtaggtc   9900
gttcgctcca agctgggctg tgtgcacgaa ccccccgttc agcccgaccg ctgcgcctta   9960
tccggtaact atcgtcttga gtccaacccg gtaagacacg acttatcgcc actggcagca  10020
gccactggta acaggattag cagagcgagg tatgtaggcg gtgctacaga gttcttgaag  10080
tggtggccta actacggcta cactagaaga acagtatttg gtatctgcgc tctgctgaag  10140
ccagttacct tcggaaaaag agttggtagc tcttgatccg gcaaacaaac caccgctggt  10200
agcggtggtt ttttgtttg caagcagcag attacgcgca gaaaaaaagg atctcaagaa  10260
gatcctttga tcttttctac ggggtctgac gctcagtgga acgaaaactc acgttaaggg  10320
attttggtca tgatctatgt cgggtgcgga gaaagaggta atgaaatggc atacgagtaa  10380
acttggtctg acaccgctgc atgagattat caaaaaggat cttcacctag atccttttaa  10440
attaaaaatg aagttttaaa tcaatctaaa gtatatatga gtaaacttgg tctgacagtt  10500
accaatgctt aatcagtgag gcacctatct cagcgatctg tctatttcgt tcatccatag  10560
ttgcctgact ccccgtcgtg tagataacta cgatacggga gggcttacca tctggcccca  10620
gtgctgcaat gataccgcga gacccacgct caccggctcc agatttatca gcaataaacc  10680
agccagccgg aagcgccgag cgcagaagtg gtcctgcaac tttatccgcc tccatccagt  10740
ctattaactg ttgccgggaa gctagagtaa gtagttcgcc agttaatagt ttgcggagcg  10800
ttgttgccat tgctacaggc atcgtggtgt cacgctcgtc gtttggtatg gcttcattca  10860
gctccggttc ccaacgatca aggcgagtta catgatcccc catgttgtgc aaaaaagcgg  10920
ttagctcctt cggtcctccg atggttgtca gaagtaagtt ggccgcagtg ttatcactca  10980
tggttatggc agcactgcat aattctctta ctgtcatgcc atccgtaaga tgcttttctg  11040
tgactggtga gtattcaacc aagtcattct gagaatagtg tatgcggcga ccgagttgct  11100
cttgcccggc gtcaatacgg gataataccg cgccacatag cagaacttta aaagtgctca  11160
tcattgggaa gcgttcttcg ggcgaaaac tctcaaggat cttaccgctg ttgagatcca  11220
gttcgatgta acccacacga gcacccaact gatcttcagc atcttttact ttcaccagcg  11280
tttctgggtg agcaaaaaca ggaaggcaaa atgccgcaaa aagggaata agggcgacac  11340
ggaaatgttg aatactcata cgcttccttt tcaatagta ttgaagcatt tatcagggtt  11400
attgtctcgg gagcgaatac atatttgaat gtatttagaa aaa                    11443

<210> SEQ ID NO 9
<211> LENGTH: 12844
<212> TYPE: DNA
<213> ORGANISM: Artificial Sequence
<220> FEATURE:
<223> OTHER INFORMATION: Synthetic promoter

<400> SEQUENCE: 9
```

```
taaacaaata ggggttccgc gcacatttcc ccgaaaagtg ccacctgacg tctaagaaac      60
cattattatc atgacattaa cctataaaaa taggcgtatc acgaggccct ttcgtcttca     120
agaaaattaa tcgcaccggt atctatgtcg ggtgcggaga aagaggtaat gaaatggcag     180
ctagcatcat caataatata ccttattttg gattgaagcc aatatgataa tgaggggggtg     240 gagtttgtga cgtggcgcgg ggcgtgggaa cggggcgggt gacgtagtag tgtggcggaa     300
gtgtgatgtt gcaagtgtgg cggaacacat gtaagcgacg gatgtggcaa aagtgacgtt     360
tttggtgtgc gccggtgtac acaggaagtg acaattttcg cgcggtttta ggcggatgtt     420
gtagtaaatt tgggcgtaac cgagtaagat ttggccattt tcgcgggaaa actgaataag     480
aggaagtgaa atctgaataa ttttgtgtta ctcatagcgc gtaatagtgc gccggtgtac     540
acaggaagtg acaattttcg cgcggtttta ggcggatgtt gtagtaaatt tgggcgtaac     600
cgagtaagat ttggccattt tcgcgggaaa actgaataag aggaagtgaa atctgaataa     660
ttttgtgtta ctcattttgt ctagggagat ccggtaccga tatcctagac aacgatgctg     720
agctaactat aacggtccta aggtagcgac cgcgagact aggtgtattt atctaagcga     780
tcgcttaatt aaggccggcc gccgcaataa aatatcttta ttttcattac atctgtgtgt     840
tggttttttg tgtgaatcca tagtactaac atacgctctc catcaaaaca aaacgaaaca     900
aaacaaacta gcaaaatagg ctgtccccag tgcaagtcca ggtgccagaa catttctcta     960
tccataatgc aggggtaccg ggtgatgacg gtgaaaacct ccaattgcgg agtactgtcc    1020
tccgagcgga gtactgtcct ccgagcggag tactgtcctc cgagcggagt actgtcctcc    1080
gagcggagta ctgtcctccg agcggagtac tgtcctccga gcggagagtc cccggggacc    1140
tagagggtat ataatgggtg ccttagctgg tgtgtgacct catcttcctg tacgcccctg    1200
caggggcgcg ccacgcgtcg aagaaggtga gtaatcttaa catgctcttt tttttttttt    1260
ttgctaatcc cttttgtgtg ctgatgttag gatgacattt acaacaaatg tttgttcctg    1320
acaggaaaaa ccttgctggg taccttcgtt gccggacact tcttgtcctc tactttggaa    1380
aaaaggaatt gagagccgct agcgccacca tgattagccc tttcctcgtg ctcgccattg    1440
gcacatgcct caccaatagc ctcgtgcctg agaaagagaa agaccctaag tattggaggg    1500
accaagccca agagacactg aaatacgctc tggaactgca aaagctcaac acaaacgtcg    1560
ccaaaaacgt catcatgttc ctcggcgatg gcatgggcgt cagcacagtg acagccgcta    1620
gaatcctgaa aggccaactg catcacaatc ccggagagga accaggctg gaaatggata    1680 agtttccctt tgtggctctg tccaagacat acaataccaa tgcccaagtg cctgactccg    1740
ccggaaccgc taccgcctac ctgtgcggag tgaaagccaa tgagggaacc gtcggcgtca    1800
gcgctgccac agagaggagc agatgcaata ccacacaggg aaacgaagtg acaagcattc    1860
tgaggtgggc taaggatgcc ggaaagtccg tgggaatcgt caccacaacc agggtgaatc    1920
acgctacccc tagcgctgcc tatgcccata gcgctgacag ggactggtac tccgacaatg    1980
agatgccccc tgaggctctg tcccagggat gcaaagacat tgcctatcag ctcatgcaca    2040
acattagaga catcgacgtg attatgggag gcggaagaaa atatatgtac cctaagaata    2100
agacagacgt ggagtatgag tccgacgaaa aggctagagg aaccaggctg gatggcctcg    2160
acctcgtgga tacctggaag tccttcaaac ccaggtacaa acactcccac tttatctgga    2220
acaggaccga actgctgacc ctggaccctc acaacgtcga ttacctcctg ggactgtttg    2280
agcctggcga tatgcaatac gaactgaata gaaataacgt caccgatccc tccctgtccg    2340
agatggtggt cgtggctatc caaatcctca gaaaaaaccc taagggattc tttctgctcg    2400
```

```
tggaaggcgg aagaattgac cacggccatc acgaaggcaa agccaagcaa gctctccacg   2460
aggctgtgga aatggataga gctatcggac aggctggctc cctgacaagc tccgaggata   2520
ccctcaccgt cgtgacagcc gatcactccc acgtttttac attcggaggc tataccccta   2580
gaggaaactc catctttggc ctcgcccta tgctgtccga taccgataag aaacccttta   2640
ccgctatcct ctacggaaac ggacccggat acaaagtggt cggcggagag agggagaatg   2700
tgagcatggt ggactatgcc cataacaatt accaagccca aagcgctgtg cccctgagac   2760
acgaaaccca cggcggagag gatgtggctg tgtttagcaa aggccctatg gcccacctgt   2820
tgcatggcgt ccacgaacag aattacgtcc cccatgtgat ggcctatgcc gcttgcattg   2880
gcgctaacct cggccattgc gctcccgcca gctccgccgg aagcctcgcc gctggccctc   2940
tgctcctggc tctggctctg tatcccctga gcgtcctgtt tggcggaggc ggaagcggag   3000
gcggaggctc cggcggaggc ggaagctgtc agcctgtgac acaggaggac ggaaaggaaa   3060
gcaggatctc cgtgcaagag taaatcgatt gcgcaaagct ttcgcgatag gcgagaccaa   3120
tgggtgtgta cgtagcggcc gcgtcgacga tagcttgatg ggtggcatcc ctgtgacccc   3180
tccccagtgc ctctcctggc cctggaagtt gccactccag tgcccaccag ccttgtccta   3240
ataaaattaa gttgcatcat tttgtctgac taggtgtcct tctataatat tatggggtgg   3300 agggggggtgg tatggagcaa ggggcaagtt gggaagacaa cctgtagggc ctgcggggtc   3360
tattgggaac caagctggag tgcagtggca caatcttggc tcactgcaat ctccgcctcc   3420
tgggttcaag cgattctcct gcctcagcct cccgagttgt tgggattcca ggcatgcatg   3480
accaggctca gctaattttt gtttttttgg tagagacggg gtttcaccat attggccagg   3540
ctggtctcca actcctaatc tcaggtgatc tacccacctt ggcctcccaa attgctggga   3600
ttacaggcgt gaaccactgc tcccttccct gtccttctga ttttaaaata actataccag   3660
caggaggacg tccagacaca gcataggcta cctggccatg cccaaccggt gggacatttg   3720
agttgcttgc ttggcactgt cctctcatgc gttgggtcca ctcagtagat gcctgttgaa   3780
ttctgattta aatcggtccg cgtacggcgt ggtaggtccg aacgaatcca tggattaccc   3840
tgttatccct atccggagtt aacctcgagg acttcggaac ttctagaacc agaccgttca   3900
gtttaaacgc tcttctcccc ctcgagtatg tcctactttt ataaactttg gttgaactaa   3960
ataaaacagc aacatgtacc caacgttttt agactgtttt attcagtacc ataaacattc   4020
actaaactat acagagctaa aatcatgcaa aagattgcaa aacaaactgc cttgggaaat   4080
ttccagtcta agctaaatgg accaagtata ggattgaatt ttaagaagtt ggtgggaaga   4140
ttccagctct tgtactcaca ggtaaggtcc taggattcta tttgttgaag tgtctgcaga   4200
ccctctccct acagcagggg cgtggagcaa atgtgcattc aggaagtgct tattagtccc   4260
cccaaaacct ttttcgtgac gacagacgga tggaggcctc agacgactcc ggcagtagga   4320
ccctgaacca aatgcctgag ctgcgctcga aaggctcgtc ttgcaggagc tggcgagtgg   4380
cacgggcttc ggtggccggg ctcggggctc ggggctcggg gccggagcc ggggggggcg   4440 gggggtccgt gccagggcg ctctgtggct cgattcatgt cccgccctc ccacctgagc   4500 acactgggca gagagcctgc ggcatcgggc cagtcgcgcc tcctcgtccg ccctgggcgg   4560
gtcgctgggc cccaggccgc tttctacagc tcctttaata aaatggacag caggggtcct   4620
aaccagacgt gggcatcaag acaaaggagg cggccagacg cgcttgaggg cctgctcgct   4680
agctcccgcc cccccattcc gcggtcatcc ggggacagag gccaggccgg actgggtgga   4740
```

```
gttgggactc atacgtctgc gtccaggaag gcgccgggcg agccccagct agacgtgacg    4800
ggcggggccg aacacggcag cggaccagag gcccgcggcg caccggcgtg gggcggggca    4860
agcggagcct tccgggatgc cgcgcggcag ccggcttccg gctgtgggtg gtgcggggga    4920
cagcggcggc cggaagctga ctgagccggc ctttggtaac gccgcctgca cttctggggg    4980
cgtcgagcct ggcggtagaa tcttcccagt aggcggcgcg ggagggaaaa gaggattgag    5040
ggcatgcggg gggggggggg ggcaattggc caccatgggc cccaagaaga aaaggaaggt    5100 ggccccccccc accgacgtga gcctgggcga cgagctgcac ctggacggcg aggacgtggc    5160
catggcccac gccgacgccc tggacgactt cgacctggac atgctgggcg acggcgacag    5220
ccccggcccc ggcttcaccc cccacgacag cgccccctac ggcgccctgg acatggccga    5280
cttcgagttc gagcagatgt tcaccgacgc cctgggcatc gacgagtacg gcggccatat    5340
ggagatgccc gtggacagga ttctggaggc cgaactcgcc gtggagcaga aaagcgacca    5400
gggcgtggag ggccccggcg gaaccggcgg cagcggcagc agcccaacg accccgtgac    5460 caacatctgc caggccgccg acaagcagct gttcaccctg gtggagtggg ccaagaggat    5520
tccccacttc agcagcctgc cctggacga ccaggtgatc ctgctgaggg ccggatggaa    5580
cgagctgctg atcgccagct tcagccacag gagcatcgac gtgagggacg gcatcctgct    5640
ggccaccggc ctgcacgtcc ataggaacag cgcccacagc gccggagtgg gcgccatctt    5700
cgacagggtg ctgaccgagc tggtgagcaa gatgagggac atgaggatgg acaagaccga    5760
gctgggctgc ctgagggcca tcatcctgtt caacccgag gtgaggggcc tgaaaagcgc    5820
ccaggaggtg gagctgctga gggagaaggt gtacgccgcc ctggaggagt acaccaggac    5880
cacccacccc gacgagcccg gcagattcgc caagctgctg ctgaggctgc ccagcctgag    5940
gagcatcggc ctgaagtgcc tggagcacct gttcttcttc aggctgatcg gcgacgtgcc    6000
catcgacacc ttcctgatgg agatgctgga gagcccagc gacagctgag ccggcaactc    6060
gctgtagtaa ttccagcgag aggcagaggg agcgagcggg cggcgggcta gggtggagga    6120
gcccggcgag cagagctgcg ctgcgggcgt cctgggaagg gagatccgga gcgaataggg    6180
ggcttcgcct ctggcccagc cctcccgctg atccccagc cagcggtgcg caaccctagc    6240
cgcatccacg aaactttgcc catagcagcg ggcgggcact ttgcactgga acttacaaca    6300
cccgagcaag gacgcgactc tccgacgcg gggaggctat tctgcccatt tggggacact    6360
tccccgccgc tgccaggacc cgcttctctg aaaggctctc cttgcagctg cttagacgct    6420 ggatttttt cgggtagtgg aaaaccagca gcctcccgcg accagatctg ccaccatgaa    6480
gctgctgagc agcatcgagc aggcttgcga catctgcagg ctgaagaagc tgaagtgcag    6540
caaggagaag cccaagtgcg ccaagtgcct gaagaacaac tgggagtgca gatcagccc    6600 caagaccaag aggagccccc tgaccagggc ccacctgacc gaggtggaga gcaggctgga    6660
gaggctggag cagctgttcc tgctgatctt cccagggag gacctggaca tgatcctgaa    6720
gatggacagc ctgcaagaca tcaaggccct gctgaccggc ctgttcgtgc aggacaacgt    6780
gaacaaggac gccgtgaccg acaggctggc cagcgtggag accgacatgc ccctgaccct    6840
gaggcagcac aggatcagcg ccaccagcag cagcgaggag agcagcaaca agggccagag    6900
gcagctgacc gtgagccccg agtttccgg gatcaggccc gagtgcgtgg tgcccgagac    6960
ccagtgcgcc atgaaaagga aggagaagaa ggcccagaag gagaaggaca gctgcccgt    7020 gagcaccacc accgtcgatg accacatgcc ccccatcatg cagtgcgagc cccccccccc    7080
cgaggccgcc aggattcacg aggtcgtgcc caggttcctg agcgacaagc tgctggtgac    7140
```

```
caacaggcag aagaacatcc cccagctgac cgccaaccag cagttcctga tcgccaggct    7200
gatctggtat caggacggct acgagcagcc cagcgacgag gacctgaaaa ggatcaccca    7260
gacctggcag caggccgacg acgagaacga ggagagcgac acccccttca ggcagatcac    7320
cgagatgacc atcctgaccg tgcagctgat cgtggagttc gccaagggcc tgcccggatt    7380
cgccaagatc agccagcccg accagatcac cctgctgaag gcttgcagca gcgaggtgat    7440
gatgctgagg gtggccagga ggtacgacgc cgccagcgac agcatcctgt tcgccaacaa    7500
ccaggcttac accagggaca actacaggaa ggctggcatg gccgaggtga tcgaggacct    7560
cctgcacttc tgcagatgta tgtacagcat ggccctggac aacatccact acgccctgct    7620
gaccgccgtg gtgatcttca gcgacaggcc cggcctggag cagccccagc tggtggagga    7680
gatccagagg tactacctga acaccctgag gatctacatc ctgaaccagc tgagcggcag    7740
cgccaggagc agcgtgatct acggcaagat cctgagcatc ctgagcgagc tgaggaccct    7800
gggaatgcag aacagcaata tgtgtatcag cctgaagctg aagaacagga agctgccccc    7860
cttcctggag gagatttggg acgtggccga catgagccac acccagcccc cccccatcct    7920
ggagagcccc accaacctgt gaatcgatta gacatgataa gatacattga tgagtttgga    7980
caaaccacaa ctagaatgca gtgaaaaaaa tgcttaattt gtgaaatttg tgatgctatt    8040
gctttaattg taaccattat aagctgcaat aaacaagtta ataaacatt tgcattcatt    8100 ttatgtttca ggttcagggg gagatgtggg aggttttta aagcaagtaa aacctctaca    8160
aatgtggtat ctagagctct tccaaataga tctggaaggt gctgaggtac gatgagaccc    8220
gcaccaggtg cagaccctgc gagtgtggcg gtaaacatat taggaaccag cctgtgatgc    8280
tggatgtgac cgaggagctg aggcccgatc acttggtgct ggcctgcacc cgcgctgagt    8340
ttggctctag cgatgaagat acagattgag gtactgaaat gtgtgggcgt ggcttaaggg    8400
tgggaaagaa tatataaggt gggggtctta tgtagttttg tatctgtttt gcagcagccg    8460
ccgccgccat gagcaccaac tcgtttgatg gaagcattgt gagctcatat ttgacaacgc    8520
gcatgccccc atgggccggg gtgcgtcaga atgtgatggg ctccagcatt gatggtcgcc    8580
ccgtcctgcc cgcaaactct actaccttga cctacgagac cgtgtctgga acgccgttgg    8640
agactgcagc ctccgccgcc gcttcagccg ctgcagccac cgcccgcggg attgtgactg    8700
actttgcttt cctgagcccg cttgcaagca gtgcagcttc cgttcatcc gcccgcgatg    8760 acaagttgac ggctcttttg gcacaattgg attctttgac ccgggaactt aatgtcgttt    8820
ctcagcagct gttggatctg cgccagcagg tttctgccct gaaggcttcc tcccctccca    8880
atgcggttta aaacataaat aaaaaaccag actctgtttg gatttggatc aagcaagtgt    8940
cttgctgtct ttatttaggg gttttgcgcg cgcggtaggc ccgggaccag cggtctcggt    9000
cgttgagggt cctgtgtatt ttttccagga cgtggtaaag gtgactctgg atgttcagat    9060
acatgggcat aagcccgtct ctggggtgga ggtagcacca ctgcagagct tcatgctgcg    9120
gggtggtgtt gtagatgatc cagtcgtagc aggagcgctg ggcgtggtgc ctaaaaatgt    9180 cttcagtag caagctgatt gccaggggca ggcccttggt gtaagtgttt acaaagcggt    9240
taagctggga tgggtgcata cgtggggata tgagatgcat cttggactgt attttaggt    9300 tggctatgtt cccagccata tccctccggg gattcatgtt gtgcagaacc accagcacag    9360
tgtatccggt gcacttggga aatttgtcat gtagcttaga aggaaatgcg tggaagaact    9420
tggagacgcc cttgtgacct ccaagatttt ccatgcattc gtccataatg atggcaatgg    9480
```

```
gcccacgggc ggcggcctgg gcgaagatat ttctgggatc actaacgtca tagttgtgtt    9540
ccaggatgag atcgtcatag gccatttta caaagcgcgg gcggagggtg ccagactgcg     9600
gtataatggt tccatccggc ccaggggcgt agttaccctc acagatttgc atttcccacg    9660
ctttgagttc agatgggggg atcatgtcta cctgcgggc gatgaagaaa acggtttccg     9720
gggtagggga gatcagctgg gaagaaagca ggttcctgag cagctgcgac ttaccgcagc    9780
cggtgggccc gtaaatcaca cctattaccg ggtgcaactg gtagttaaga gagctgcagc    9840
tgccgtcatc cctgagcagg ggggccactt cgttaagcat gtccctgact cgcatgtttt    9900
ccctgaccaa atccgccaga aggcgctcgc cgcccagcga tagcagttct tgcaaggaag    9960
caaagttttt caacggtttg agaccgtccg ccgtaggcat gcttttgagc gtttgaccaa    10020
gcagttccag gcggtcccac agctcggtca cctgctctac ggcatctcga tccagcatat    10080
ctcctcgttt cgcgggttgg ggcggctttc gctgtacggc agtagtcggt gctcgtccag    10140
acgggccagg gtcatgtctt tccacgggcg cagggtcctc gtcagcgtag tctgggtcac    10200
ggtgaagggg tgcgctccgg gctgcgcgct ggccagggtg cgcttgaggc tggtcctgct    10260
ggtgctgaag cgctgccggt cttcgccctg cgcgtcggcc aggtagcatt tgaccatggt    10320
gtcatagtcc agccctccg cggcgtggcc cttggcgcgc agcttgccct tggaggaggc     10380
gccgcacgag gggcagtgca gacttttgag ggcgtagagc ttgggcgcga gaaataccga    10440
ttccggggag taggcatccg cgccgcaggc cccgcagacg gtctcgcatt ccacgagcca    10500
ggtgagctct ggccgttcgg ggtcaaaaac caggtttccc ccatgctttt tgatgcgttt    10560
cttacctctg gtttccatga gccggtgtcc acgctcggtg acgaaaaggc tgtccgtgtc    10620
cccgtataca gacttgagag gcctgtcctc gaccgatgcc cttgagagcc ttcaacccag    10680
tcagctcctt ccggtgggcg cggggcatga ctatcgtcgc cgcacttatg actgtcttct    10740
ttatcatgca actcgtagga caggtgccgg cagcgctctg ggtcattttc ggcgaggacc    10800
gctttcgctg gagcgcgacg atgatcggcc tgtcgcttgc ggtattcgga atcttgcacg    10860
ccctcgctca agccttcgtc actggtcccg ccaccaaacg tttcggcgag aagcaggcca    10920
ttatcgccgg catggcggcc gacgcgctgg gctacgtctt gctggcgttc gcgacgcgag    10980
gctggatggc cttccccatt atgattcttc tcgcttccgg cggcatcggg atgcccgcgt    11040
tgcaggccat gctgtccagg caggtagatg acgaccatca gggacagctt caaggccagc    11100
aaaaggccag gaaccgtaaa aaggccgcgt tgctggcgtt tttccatagg ctccgccccc    11160
ctgacgagca tcacaaaaat cgacgctcaa gtcagaggtg gcgaaacccg acaggactat    11220
aaagatacca ggcgtttccc cctggaagct ccctcgtgcg ctctcctgtt ccgaccctgc    11280
cgcttaccgg atacctgtcc gcctttctcc cttcgggaag cgtggcgctt tctcatagct    11340
cacgctgtag gtatctcagt tcggtgtagg tcgttcgctc caagctgggc tgtgtgcacg    11400
aaccccccgt tcagcccgac cgctgcgcct tatccggtaa ctatcgtctt gagtccaacc    11460
cggtaagaca cgacttatcg ccactggcag cagccactgg taacaggatt agcagagcga    11520
ggtatgtagg cggtgctaca gagttcttga agtggtggcc taactacggc tacactagaa    11580
ggacagtatt tggtatctgc gctctgctga agccagttac cttcggaaaa agagttggta    11640
gctcttgatc cggcaaacaa accaccgctg gtagcggtgg tttttttgtt tgcaagcagc    11700
agattacgcg cagaaaaaaa ggatctcaag aagatccttt gatcttttct acggggtctg    11760
acgctcagtg gaacgaaaac tcacgttaag ggatttggt catgagatta tcaaaaagga    11820
tcttcaccta gatccttta aattaaaaat gaagttttaa atcaatctaa agtatatatg    11880
```

```
agtaaacttg gtctgacagt taccaatgct taatcagtga ggcacctatc tcagcgatct    11940
gtctatttcg ttcatccata gttgcctgac tccccgtcgt gtagataact acgatacggg    12000
agggcttacc atctggcccc agtgctgcaa tgataccgcg agacccacgc tcaccggctc    12060
cagatttatc agcaataaac cagccagccg aagggccga gcgcagaagt ggtcctgcaa     12120
ctttatccgc ctccatccag tctattaatt gttgccggga agctagagta agtagttcgc    12180
cagttaatag tttgcgcaac gttgttgcca ttgctgcagg catcgtggtg tcacgctcgt    12240
cgtttggtat ggcttcattc agctccggtt cccaacgatc aaggcgagtt acatgatccc    12300
ccatgttgtg caaaaaagcg gttagctcct tcggtcctcc gatcgttgtc agaagtaagt    12360
tggccgcagt gttatcactc atggttatgg cagcactgca taattctctt actgtcatgc    12420
catccgtaag atgcttttct gtgactggtg agtactcaac caagtcattc tgagaatagt    12480
gtatgcggcg accgagttgc tcttgcccgg cgtcaacacg ggataatacc gcgccacata    12540
gcagaacttt aaaagtgctc atcattggaa aacgttcttc ggggcgaaaa ctctcaagga    12600
tcttaccgct gttgagatcc agttcgatgt aacccactcg tgcacccaac tgatcttcag    12660
catcttttac tttcaccagc gtttctgggt gagcaaaaac aggaaggcaa aatgccgcaa    12720
aaaagggaat aagggcgaca cggaaatgtt gaatactcat actcttcctt tttcaatatt    12780
attgaagcat ttatcagggt tattgtctca tgagcggata catatttgaa tgtatttaga    12840
aaaa                                                                 12844

<210> SEQ ID NO 10
<211> LENGTH: 300
<212> TYPE: DNA
<213> ORGANISM: Artificial Sequence
<220> FEATURE:
<223> OTHER INFORMATION: Synthetic CD95-ADAM8 reporter

<400> SEQUENCE: 10
gctagcgcca ccatgattag ccctttcctc gtgctcgcca ttggcacatg cctcaccaat      60
agcctcgtgc ctgagaaaga gaaagacgga ggcggaggct ccggcggagg cggaagcgga     120
ggcggaggct ccgagtccct gaaactgagg agaagggtgc atgagacaga caaaaactgt     180
agatccggca cccccctca gaccggcctg gagaaaccca caggcacagg ccaagaaaaa      240
cagggagccg gagcccctac cgctcccgga cccggaggct cccccggagg ctaaatcgat     300

<210> SEQ ID NO 11
<211> LENGTH: 93
<212> TYPE: PRT
<213> ORGANISM: Artificial Sequence
<220> FEATURE:
<223> OTHER INFORMATION: Synthetic CD95-ADAM8 reporter

<400> SEQUENCE: 11

Met Ile Ser Pro Phe Leu Val Leu Ala Ile Gly Thr Cys Leu Thr Asn
1               5                   10                  15

Ser Leu Val Pro Glu Lys Glu Lys Asp Gly Gly Gly Ser Gly Gly
            20                  25                  30

Gly Gly Ser Gly Gly Gly Gly Ser Glu Ser Leu Lys Leu Arg Arg Arg
        35                  40                  45

Val His Glu Thr Asp Lys Asn Cys Arg Ser Gly Thr Pro Pro Gln Thr
    50                  55                  60

Gly Leu Glu Lys Pro Thr Gly Thr Gly Gln Arg Lys Gln Gly Ala Gly
65                  70                  75                  80
```

```
Ala Pro Thr Ala Pro Gly Pro Gly Gly Ser Pro Gly Gly
            85                  90

<210> SEQ ID NO 12
<211> LENGTH: 339
<212> TYPE: DNA
<213> ORGANISM: Artificial Sequence
<220> FEATURE:
<223> OTHER INFORMATION: Synthetic CD40-CD3 reporter

<400> SEQUENCE: 12
gctagcgcca ccatgattag ccctttcctc gtgctcgcca ttggcacatg cctcaccaat      60
agcctcgtgc ctggcggagg cggaagcgga ggcggaggct ccggcggagg cggaagctgt     120
cagcctgtga cacaggagga cggaaaggaa agcaggatct ccgtgcaaga gaggcagcct     180
gcccctaccc ctagcaatgg ctcccccaaa gacggacccg aaatccctcc cacaggcgga     240
aaggctaagg ccaagcccgt gacaagagga gccggagcca ggagcggaac ccctccccaa     300
accggactgg aaaagcctac cggaaccgga tgaatcgat                            339

<210> SEQ ID NO 13
<211> LENGTH: 106
<212> TYPE: PRT
<213> ORGANISM: Artificial Sequence
<220> FEATURE:
<223> OTHER INFORMATION: Synthetic CD40-CD3 reporter

<400> SEQUENCE: 13

Met Ile Ser Pro Phe Leu Val Leu Ala Ile Gly Thr Cys Leu Thr Asn
1               5                   10                  15

Ser Leu Val Pro Gly Gly Gly Gly Ser Gly Gly Gly Gly Ser Gly Gly
            20                  25                  30

Gly Gly Ser Cys Gln Pro Val Thr Gln Glu Asp Gly Lys Glu Ser Arg
        35                  40                  45

Ile Ser Val Gln Glu Arg Gln Pro Ala Pro Thr Pro Ser Asn Gly Ser
    50                  55                  60

Pro Lys Asp Gly Pro Glu Ile Pro Pro Thr Gly Gly Lys Ala Lys Ala
65                  70                  75                  80

Lys Pro Val Thr Arg Gly Ala Gly Ala Arg Ser Gly Thr Pro Pro Gln
            85                  90                  95

Thr Gly Leu Glu Lys Pro Thr Gly Thr Gly
            100                 105

<210> SEQ ID NO 14
<211> LENGTH: 1692
<212> TYPE: DNA
<213> ORGANISM: Artificial Sequence
<220> FEATURE:
<223> OTHER INFORMATION: Synthetic alkaline phosphatase - c terminal

<400> SEQUENCE: 14
gctagcgcca ccatgattag ccctttcctc gtgctcgcca ttggcacatg cctcaccaat      60
agcctcgtgc ctgagaaaga gaaagaccct aagtattgga gggaccaagc ccaagagaca     120
ctgaaatacg ctctggaact gcaaaagctc aacacaaacg tcgccaaaaa cgtcatcatg     180
ttcctcggcg atggcatggg cgtcagcaca gtgacagccg ctagaatcct gaaaggccaa     240
ctgcatcaca atcccggaga ggaaccagg ctggaaatgg ataagtttcc ctttgtggct     300
ctgtccaaga catacaatac caatgcccaa gtgcctgact ccgccggaac cgctaccgcc     360
```

```
tacctgtgcg gagtgaaagc caatgaggga accgtcggcg tcagcgctgc cacagagagg    420
agcagatgca ataccacaca gggaaacgaa gtgacaagca ttctgaggtg ggctaaggat    480
gccggaaagt ccgtgggaat cgtcaccaca accagggtga atcacgctac ccctagcgct    540
gcctatgccc atagcgctga cagggactgg tactccgaca atgagatgcc ccctgaggct    600
ctgtcccagg gatgcaaaga cattgcctat cagctcatgc acaacattag agacatcgac    660
gtgattatgg gaggcggaag aaaatatatg taccctaaga ataagacaga cgtggagtat    720
gagtccgacg aaaaggctag aggaaccagg ctggatggcc tcgacctcgt ggatacctgg    780
aagtccttca acccaggta caaacactcc cactttatct ggaacaggac cgaactgctg    840
accctggacc ctcacaacgt cgattacctc ctgggactgt ttgagcctgg cgatatgcaa    900
tacgaactga atagaaataa cgtcaccgat ccctccctgt ccgagatggt ggtcgtggct    960
atccaaatcc tcagaaaaaa ccctaaggga ttctttctgc tcgtggaagg cggaagaatt    1020
gaccacggcc atcacgaagg caaagccaag caagctctcc acgaggctgt ggaaatggat    1080
agagctatcg gacaggctgg ctccctgaca agctccgagg ataccctcac cgtcgtgaca    1140
gccgatcact cccacgtttt tacattcgga ggctataccc ctagaggaaa ctccatcttt    1200
ggcctcgccc ctatgctgtc cgataccgat aagaaacccc ttaccgctat cctctacgga    1260
aacggacccg gatacaaagt ggtcggcgga gagagggaga atgtgagcat ggtggactat    1320
gcccataaca attaccaagc ccaaagcgct gtgcccctga cacacgaaac ccacggcgga    1380
gaggatgtgg ctgtgtttag caaaggcccc atggcccacc tgttgcatgg cgtccacgaa    1440
cagaattacg tcccccatgt gatggcctat gccgcttgca ttggcgctaa cctcggccat    1500
tgcgctcccg ccagctccgc cggaagcctc gccgctggcc ctctgctcct ggctctggct    1560
ctgtatcccc tgagcgtcct gtttggcgga ggcggaagcg gaggcggagg ctccggcgga    1620
ggcggaagct gtcagcctgt gacacaggag gacggaaagg aaagcaggat ctccgtgcaa    1680
gagtaaatcg at                                                       1692
```

<210> SEQ ID NO 15
<211> LENGTH: 557
<212> TYPE: PRT
<213> ORGANISM: Artificial Sequence
<220> FEATURE:
<223> OTHER INFORMATION: Synthetic alkaline phosphatase - c terminal CD40

<400> SEQUENCE: 15

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val

-continued

```
            115                 120                 125
Gly Val Ser Ala Ala Thr Glu Arg Ser Arg Cys Asn Thr Thr Gln Gly
        130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
    450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe Gly Gly Gly Gly
        515                 520                 525

Ser Gly Gly Gly Gly Ser Gly Gly Gly Ser Cys Gln Pro Val Thr
    530                 535                 540
```

Gln Glu Asp Gly Lys Glu Ser Arg Ile Ser Val Gln Glu
545                 550                 555

<210> SEQ ID NO 16
<211> LENGTH: 354
<212> TYPE: DNA
<213> ORGANISM: Artificial Sequence
<220> FEATURE:
<223> OTHER INFORMATION: Synthetic CD28-CD3 reporter

<400> SEQUENCE: 16

```
gctagcgcca ccatgattag ccctttcctc gtgctcgcca ttggcacatg cctcaccaat      60
agcctcgtgc ctagatccga cgtgaactcc agaacaggcc ctagcggagc cacaccccct     120
agcggaaacc cttacacaat cacaggctcc cagcaactgc aagtgtatag caaaaccgga     180
ttcaatcccg ctcccacacc ctccaacgga agccctaagg atggccctga gattccccct     240
accggaggct ccggcggagg cggaagcgga ggcggaggct ccaaggctaa ggccaagccc     300
gtgacaagag agccggagc cggacccgga ggctcccccg aggctaaat cgat            354
```

<210> SEQ ID NO 17
<211> LENGTH: 111
<212> TYPE: PRT
<213> ORGANISM: Artificial Sequence
<220> FEATURE:
<223> OTHER INFORMATION: Synthetic CD28-CD3 reporter

<400> SEQUENCE: 17

Met Ile Ser Pro Phe Leu Val Leu Ala Ile Gly Thr Cys Leu Thr Asn
1               5                   10                  15

Ser Leu Val Pro Arg Ser Asp Val Asn Ser Arg Thr Gly Pro Ser Gly
                20                  25                  30

Ala Thr Pro Pro Ser Gly Asn Pro Tyr Thr Ile Thr Gly Ser Gln Gln
            35                  40                  45

Leu Gln Val Tyr Ser Lys Thr Gly Phe Asn Pro Ala Pro Thr Pro Ser
    50                  55                  60

Asn Gly Ser Pro Lys Asp Gly Pro Glu Ile Pro Pro Thr Gly Gly Ser
65                  70                  75                  80

Gly Gly Gly Gly Ser Gly Gly Gly Ser Lys Ala Lys Ala Lys Pro
                85                  90                  95

Val Thr Arg Gly Ala Gly Ala Gly Pro Gly Gly Ser Pro Gly Gly
            100                 105                 110

<210> SEQ ID NO 18
<211> LENGTH: 375
<212> TYPE: DNA
<213> ORGANISM: Artificial Sequence
<220> FEATURE:
<223> OTHER INFORMATION: Synthetic CD28-CD40 reporter

<400> SEQUENCE: 18

```
gctagcgcca ccatgattag ccctttcctc gtgctcgcca ttggcacatg cctcaccaat      60
agcctcgtgc ctagatccga cgtgaactcc agaacaggcc ctagcggagc cacaccccct     120
agcggaaacc cttacacaat cacaggctcc cagcaactgc aagtgtatag caaaaccgga     180
ttcaatcccg ctcccacacc ctccaacgga agccctaagg atggccctga gattccccct     240
accggaggct ccggcggagg cggaagcgga ggcggaggct cctgccaacc cgtcacccag     300
gaggacggca aagagtccag aattagcgtc caggaaagac aaggccctgg cggaagccct     360
```

```
ggcggatgaa tcgat                                                       375
```

<210> SEQ ID NO 19
<211> LENGTH: 118
<212> TYPE: PRT
<213> ORGANISM: Artificial Sequence
<220> FEATURE:
<223> OTHER INFORMATION: Synthetic CD28-CD40 reporter

<400> SEQUENCE: 19

```
Met Ile Ser Pro Phe Leu Val Leu Ala Ile Gly Thr Cys Leu Thr Asn
1               5                   10                  15

Ser Leu Val Pro Arg Ser Asp Val Asn Ser Arg Thr Gly Pro Ser Gly
            20                  25                  30

Ala Thr Pro Pro Ser Gly Asn Pro Tyr Thr Ile Thr Gly Ser Gln Gln
        35                  40                  45

Leu Gln Val Tyr Ser Lys Thr Gly Phe Asn Pro Ala Pro Thr Pro Ser
    50                  55                  60

Asn Gly Ser Pro Lys Asp Gly Pro Glu Ile Pro Pro Thr Gly Gly Ser
65                  70                  75                  80

Gly Gly Gly Gly Ser Gly Gly Gly Ser Cys Gln Pro Val Thr Gln
                85                  90                  95

Glu Asp Gly Lys Glu Ser Arg Ile Ser Val Gln Glu Arg Gln Gly Pro
            100                 105                 110

Gly Gly Ser Pro Gly Gly
        115
```

<210> SEQ ID NO 20
<211> LENGTH: 1737
<212> TYPE: DNA
<213> ORGANISM: Artificial Sequence
<220> FEATURE:
<223> OTHER INFORMATION: Synthetic alkaline phosphatase - amino terminal
      CD40

<400> SEQUENCE: 20

```
gctagcgcca ccatgattag ccctttcctc gtgctcgcca ttggcacatg cctcaccaat      60
agcctcgtgc cttgccaacc cgtcacccag gaggacggca agagtccag aattagcgtc      120 caggaaggcg aggcggaag cggaggcgga ggctccggcg gaggcggaag cgaaaaggaa      180
aaggacccca atactggag agatcaggct caggaaaccc tcaagtatgc cctggaactc      240
cagaaactga ataccaatgt ggctaagaat gtgattatgt ttctgggcga cggcatggga      300
gtgtccaccg tcaccgctgc cagaatcctg aagggacagc tccaccacaa ccccggcgag      360
gagacaagac tggagatgga caaattccct ttcgtcgccc tgtccaaaac ctataacaca      420
aacgctcagg tccccgatag cgctggcaca gccacagcct atctgtgtgg cgtcaaggct      480
aacgaaggca cagtgggagt gtccgccgct accgaaagat ccagatgtaa cacaacccaa      540
ggcaatgagg tcacctccat cctcagatgg gccaaagacg ctggcaaaag cgtcggcatt      600
gtgacaacca caagagtcaa ccatgccaca ccctcgccg cttacgctca ctccgccgat      660
agagattggt atagcgataa cgaaatgcct cccgaagccc tgagccaagg ctgtaaggac      720
atcgcttacc aactgatgca caatatcagg gacattgacg ttatcatggg cggaggcagg      780
aagtatatgt atcccaaaaa caaaaccgat gtggaatacg aaagcgatga aaagccagg      840 ggcacaagac tcgacggact ggatctggtg gatacatgga gtcccttcaa gcctagatat      900
aagcatagcc atttcatttg gaatagaaca gagcttctga cactggaccc ccataacgtg      960
```

```
gactatctgc tcggcctgtt cgagcccgga gacatgcagt atgagctgaa caggaacaat   1020
gtgacagacc ctagcctgag cgaaatggtc gtggtcgcca ttcagattct gaggaagaat   1080
cccaaaggct ttttcctcct ggtcgaggga ggcagaatcg accacggcca ccacgaggga   1140
aaggccaagc aagccctcca cgaagccgtc gagatggaca gggccattgg ccaagccgga   1200
agcctcacct ccagcgagga tacactgaca gtggtcaccg ctgaccatag ccatgtgttt   1260
acctttggcg atacacacc cagggcaat agcattttcg gactggctcc catgctgtcc   1320
gacacagaca aaaagccttt cacagccatt ctgtatggca atggccctgg ctataaggtc   1380
gtgggaggcg aaagagaaaa cgtcagcatg gtggattacg ctcacaataa ctatcaggct   1440
cagtccgccg tcccctcag acatgagaca cacggaggcg aggacgtggc cgtgttctcc   1500
aagggaccta tggcccatct gctccacggc gtccatgagc aaaactatgt gcctcacgtc   1560
atggcttacg ctgcctgtat cggagccaat ctgggacact gtgccctgc tccagcgct    1620 ggctccctgg ctgccggacc cctcctgctc gccctcgccc tctaccctct gtccgtgctg   1680
ttcggaggcg gaggctccgg cggaggcgga agcggaggcg aggctcctg aatcgat      1737
```

<210> SEQ ID NO 21
<211> LENGTH: 572
<212> TYPE: PRT
<213> ORGANISM: Artificial Sequence
<220> FEATURE:
<223> OTHER INFORMATION: Synthetic alkaline phosphatase - amino terminal CD40

<400> SEQUENCE: 21

```
Met Ile Ser Pro Phe Leu Val Leu Ala Ile Gly Thr Cys Leu Thr Asn
1               5                   10                  15

Ser Leu Val Pro Cys Gln Pro Val Thr Gln Glu Asp Gly Lys Glu Ser
            20                  25                  30

Arg Ile Ser Val Gln Glu Gly Gly Gly Ser Gly Gly Gly Gly Ser
        35                  40                  45

Gly Gly Gly Gly Ser Glu Lys Glu Lys Asp Pro Lys Tyr Trp Arg Asp
    50                  55                  60

Gln Ala Gln Glu Thr Leu Lys Tyr Ala Leu Glu Leu Gln Lys Leu Asn
65                  70                  75                  80

Thr Asn Val Ala Lys Asn Val Ile Met Phe Leu Gly Asp Gly Met Gly
                85                  90                  95

Val Ser Thr Val Thr Ala Ala Arg Ile Leu Lys Gly Gln Leu His His
            100                 105                 110

Asn Pro Gly Glu Glu Thr Arg Leu Glu Met Asp Lys Phe Pro Phe Val
        115                 120                 125

Ala Leu Ser Lys Thr Tyr Asn Thr Asn Ala Gln Val Pro Asp Ser Ala
    130                 135                 140

Gly Thr Ala Thr Ala Tyr Leu Cys Gly Val Lys Ala Asn Glu Gly Thr
145                 150                 155                 160

Val Gly Val Ser Ala Ala Thr Glu Arg Ser Arg Cys Asn Thr Thr Gln
                165                 170                 175

Gly Asn Glu Val Thr Ser Ile Leu Arg Trp Ala Lys Asp Ala Gly Lys
            180                 185                 190

Ser Val Gly Ile Val Thr Thr Thr Arg Val Asn His Ala Thr Pro Ser
        195                 200                 205

Ala Ala Tyr Ala His Ser Ala Asp Arg Asp Trp Tyr Ser Asp Asn Glu
    210                 215                 220
```

```
Met Pro Pro Glu Ala Leu Ser Gln Gly Cys Lys Asp Ile Ala Tyr Gln
225                 230                 235                 240

Leu Met His Asn Ile Arg Asp Ile Asp Val Ile Met Gly Gly Gly Arg
            245                 250                 255

Lys Tyr Met Tyr Pro Lys Asn Lys Thr Asp Val Glu Tyr Glu Ser Asp
        260                 265                 270

Glu Lys Ala Arg Gly Thr Arg Leu Asp Gly Leu Asp Leu Val Asp Thr
    275                 280                 285

Trp Lys Ser Phe Lys Pro Arg Tyr Lys His Ser His Phe Ile Trp Asn
290                 295                 300

Arg Thr Glu Leu Leu Thr Leu Asp Pro His Asn Val Asp Tyr Leu Leu
305                 310                 315                 320

Gly Leu Phe Glu Pro Gly Asp Met Gln Tyr Glu Leu Asn Arg Asn Asn
                325                 330                 335

Val Thr Asp Pro Ser Leu Ser Glu Met Val Val Ala Ile Gln Ile
                340                 345                 350

Leu Arg Lys Asn Pro Lys Gly Phe Phe Leu Leu Val Glu Gly Gly Arg
            355                 360                 365

Ile Asp His Gly His His Glu Gly Lys Ala Lys Gln Ala Leu His Glu
370                 375                 380

Ala Val Glu Met Asp Arg Ala Ile Gly Gln Ala Gly Ser Leu Thr Ser
385                 390                 395                 400

Ser Glu Asp Thr Leu Thr Val Val Thr Ala Asp His Ser His Val Phe
                405                 410                 415

Thr Phe Gly Gly Tyr Thr Pro Arg Gly Asn Ser Ile Phe Gly Leu Ala
                420                 425                 430

Pro Met Leu Ser Asp Thr Asp Lys Lys Pro Phe Thr Ala Ile Leu Tyr
            435                 440                 445

Gly Asn Gly Pro Gly Tyr Lys Val Val Gly Gly Glu Arg Glu Asn Val
        450                 455                 460

Ser Met Val Asp Tyr Ala His Asn Asn Tyr Gln Ala Gln Ser Ala Val
465                 470                 475                 480

Pro Leu Arg His Glu Thr His Gly Gly Glu Asp Val Ala Val Phe Ser
                485                 490                 495

Lys Gly Pro Met Ala His Leu Leu His Gly Val His Glu Gln Asn Tyr
            500                 505                 510

Val Pro His Val Met Ala Tyr Ala Ala Cys Ile Gly Ala Asn Leu Gly
        515                 520                 525

His Cys Ala Pro Ala Ser Ser Ala Gly Ser Leu Ala Gly Pro Leu
530                 535                 540

Leu Leu Ala Leu Ala Leu Tyr Pro Leu Ser Val Leu Phe Gly Gly Gly
545                 550                 555                 560

Gly Ser Gly Gly Gly Gly Ser Gly Gly Gly Ser
                565                 570

<210> SEQ ID NO 22
<211> LENGTH: 1677
<212> TYPE: DNA
<213> ORGANISM: Artificial Sequence
<220> FEATURE:
<223> OTHER INFORMATION: Synthetic alkaline phosphatase - c terminal
      CD28

<400> SEQUENCE: 22
gctagcgcca ccatgattag cccttttcctc gtgctcgcca ttggcacatg cctcaccaat      60
```

| | | |
|---|---|---|
| agcctcgtgc ctgagaaaga gaaagaccct aagtattgga gggaccaagc ccaagagaca | 120 | |
| ctgaaatacg ctctggaact gcaaaagctc aacacaaacg tcgccaaaaa cgtcatcatg | 180 | |
| ttcctcggcg atggcatggg cgtcagcaca gtgacagccg ctagaatcct gaaaggccaa | 240 | |
| ctgcatcaca atcccggaga ggaaccaggc tggaaatgga taagtttcc ctttgtggct | 300 | |
| ctgtccaaga catacaatac caatgcccaa gtgcctgact ccgccggaac cgctaccgcc | 360 | |
| tacctgtgcg gagtgaaagc caatgaggga accgtcggcg tcagcgctgc cacagagagg | 420 | |
| agcagatgca ataccacaca gggaaacgaa gtgacaagca ttctgaggtg ggctaaggat | 480 | |
| gccggaaagt ccgtgggaat cgtcaccaca accagggtga atcacgctac ccctagcgct | 540 | |
| gcctatgccc atagcgctga cagggactgg tactccgaca atgagatgcc ccctgaggct | 600 | |
| ctgtcccagg gatgcaaaga cattgcctat cagctcatgc acaacattag agacatcgac | 660 | |
| gtgattatgg gaggcggaag aaaatatatg taccctaaga taagacaga cgtggagtat | 720 | |
| gagtccgacg aaaaggctag aggaaccagg ctggatggcc tcgacctcgt ggatacctgg | 780 | |
| aagtccttca acccaggta caaacactcc cactttatct ggaacaggac cgaactgctg | 840 | |
| accctggacc ctcacaacgt cgattacctc ctgggactgt ttgagcctgg cgatatgcaa | 900 | |
| tacgaactga atagaaataa cgtcaccgat ccctccctgt ccgagatggt ggtcgtggct | 960 | |
| atccaaatcc tcagaaaaaa ccctaaggga ttctttctgc tcgtggaagg cggaagaatt | 1020 | |
| gaccacggcc atcacgaagg caaagccaag caagctctcc acgaggctgt ggaaatggat | 1080 | |
| agagctatcg acaggctggc tccctgaca agctccgagg ataccctcac cgtcgtgaca | 1140 | |
| gccgatcact cccacgtttt tacattcgga ggctataccc ctagaggaaa ctccatcttt | 1200 | |
| ggcctcgccc ctatgctgtc cgataccgat aagaaaccct ttaccgctat cctctacgga | 1260 | |
| aacgacccg gatacaaagt ggtcggcgga gagagggaga atgtgagcat ggtggactat | 1320 | |
| gcccataaca attaccaagc ccaaagcgct gtgccctga cacgaaac ccacggcgga | 1380 | |
| gaggatgtgg ctgtgtttag caaaggcct atggcccacc tgttgcatgg cgtccacgaa | 1440 | |
| cagaattacg tcccccatgt gatggcctat gccgcttgca ttggcgctaa cctcggccat | 1500 | |
| tgcgctcccg ccagctccgc cggaagcctc gccgctggcc ctctgctcct ggctctggct | 1560 | |
| ctgtatcccc tgagcgtcct gtttggcgga ggcggaagcg gaggcggagg ctccggcgga | 1620 | |
| ggcggaagct cccagcaact gcaagtgtat agcaaaaccg gattcaactg aatcgat | 1677 | |

<210> SEQ ID NO 23
<211> LENGTH: 552
<212> TYPE: PRT
<213> ORGANISM: Artificial Sequence
<220> FEATURE:
<223> OTHER INFORMATION: Synthetic alkaline phosphatase - c terminal
      CD28

<400> SEQUENCE: 23

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
                20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

```
Pro Gly Glu Glu Thr Arg Leu Glu Met Asp Lys Phe Pro Phe Val Ala
                85                  90                  95
Leu Ser Lys Thr Tyr Asn Thr Asn Ala Gln Val Pro Asp Ser Ala Gly
            100                 105                 110
Thr Ala Thr Ala Tyr Leu Cys Gly Val Lys Ala Asn Glu Gly Thr Val
        115                 120                 125
Gly Val Ser Ala Ala Thr Glu Arg Ser Arg Cys Asn Thr Thr Gln Gly
    130                 135                 140
Asn Glu Val Thr Ser Ile Leu Arg Trp Ala Lys Asp Ala Gly Lys Ser
145                 150                 155                 160
Val Gly Ile Val Thr Thr Thr Arg Val Asn His Ala Thr Pro Ser Ala
                165                 170                 175
Ala Tyr Ala His Ser Ala Asp Arg Asp Trp Tyr Ser Asp Asn Glu Met
            180                 185                 190
Pro Pro Glu Ala Leu Ser Gln Gly Cys Lys Asp Ile Ala Tyr Gln Leu
        195                 200                 205
Met His Asn Ile Arg Asp Ile Asp Val Ile Met Gly Gly Gly Arg Lys
    210                 215                 220
Tyr Met Tyr Pro Lys Asn Lys Thr Asp Val Glu Tyr Glu Ser Asp Glu
225                 230                 235                 240
Lys Ala Arg Gly Thr Arg Leu Asp Gly Leu Asp Leu Val Asp Thr Trp
                245                 250                 255
Lys Ser Phe Lys Pro Arg Tyr Lys His Ser His Phe Ile Trp Asn Arg
            260                 265                 270
Thr Glu Leu Leu Thr Leu Asp Pro His Asn Val Asp Tyr Leu Leu Gly
        275                 280                 285
Leu Phe Glu Pro Gly Asp Met Gln Tyr Glu Leu Asn Arg Asn Asn Val
    290                 295                 300
Thr Asp Pro Ser Leu Ser Glu Met Val Val Ala Ile Gln Ile Leu
305                 310                 315                 320
Arg Lys Asn Pro Lys Gly Phe Phe Leu Leu Val Glu Gly Gly Arg Ile
                325                 330                 335
Asp His Gly His His Glu Gly Lys Ala Lys Gln Ala Leu His Glu Ala
            340                 345                 350
Val Glu Met Asp Arg Ala Ile Gly Gln Ala Gly Ser Leu Thr Ser Ser
        355                 360                 365
Glu Asp Thr Leu Thr Val Val Thr Ala Asp His Ser His Val Phe Thr
    370                 375                 380
Phe Gly Gly Tyr Thr Pro Arg Gly Asn Ser Ile Phe Gly Leu Ala Pro
385                 390                 395                 400
Met Leu Ser Asp Thr Asp Lys Lys Pro Phe Thr Ala Ile Leu Tyr Gly
                405                 410                 415
Asn Gly Pro Gly Tyr Lys Val Val Gly Gly Glu Arg Glu Asn Val Ser
            420                 425                 430
Met Val Asp Tyr Ala His Asn Asn Tyr Gln Ala Gln Ser Ala Val Pro
        435                 440                 445
Leu Arg His Glu Thr His Gly Gly Glu Asp Val Ala Val Phe Ser Lys
    450                 455                 460
Gly Pro Met Ala His Leu Leu His Gly Val His Glu Gln Asn Tyr Val
465                 470                 475                 480
Pro His Val Met Ala Tyr Ala Ala Cys Ile Gly Ala Asn Leu Gly His
                485                 490                 495
```

-continued

```
Cys Ala Pro Ala Ser Ser Ala Gly Ser Leu Ala Ala Gly Pro Leu Leu
            500             505             510

Leu Ala Leu Ala Leu Tyr Pro Leu Ser Val Leu Phe Gly Gly Gly Gly
        515             520             525

Ser Gly Gly Gly Gly Ser Gly Gly Gly Gly Ser Ser Gln Gln Leu Gln
        530             535             540

Val Tyr Ser Lys Thr Gly Phe Asn
545                 550
```